(12) United States Patent
Gygi et al.

(10) Patent No.: US 10,407,712 B2
(45) Date of Patent: Sep. 10, 2019

(54) METHODS, COMPOSITIONS AND KITS FOR HIGH THROUGHPUT KINASE ACTIVITY SCREENING USING MASS SPECTROMETRY AND STABLE ISOTOPES

(71) Applicant: President and Fellows of Harvard College, Cambridge, MA (US)

(72) Inventors: Steven P. Gygi, Foxboro, MA (US); Kazuishi Kubota, Tokyo (JP); Judit Villen, Seattle, WA (US); Yonghao Yu, Roxbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/784,734

(22) Filed: Oct. 16, 2017

(65) Prior Publication Data

US 2018/0119198 A1 May 3, 2018

Related U.S. Application Data

(63) Continuation of application No. 13/078,203, filed on Apr. 1, 2011, now abandoned, which is a continuation of application No. PCT/US2009/059329, filed on Oct. 2, 2009.

(60) Provisional application No. 61/195,096, filed on Oct. 3, 2008.

(51) Int. Cl.
*C12Q 1/48* (2006.01)
*G01N 33/68* (2006.01)

(52) U.S. Cl.
CPC ......... *C12Q 1/485* (2013.01); *G01N 33/6842* (2013.01); *G01N 33/6848* (2013.01)

(58) Field of Classification Search
CPC .................. C12Q 1/485; G01N 33/6842; G01N 33/6848
See application file for complete search history.

*Primary Examiner* — Sheridan Swope
(74) *Attorney, Agent, or Firm* — Sonia K. Guterman; Preeti T. Arun; Lawson & Weitzen LLP

(57) ABSTRACT

A mass-spectrometry-based method and substrates are provided herein for large scale kinome activity profiling directly from crude lysates using 90 chemically synthesized peptide substrates with amino acid sequences derived from known phosphoproteins. Quantification of peptide phosphorylation rates was achieved via the use of stable isotope labeled synthetic peptides. A method and substrates for obtaining 90 simultaneous activity measurements in a single-reaction format were developed and validated. The kinome activity profiling strategy was successfully applied with lysates of: cells manipulated by combination of mitogen stimulation, pharmacological perturbation and siRNA-directed kinase knockdown; seven different breast cancer cell lines treated with gefitinib; and each of normal and cancerous tissue samples from renal cell carcinoma patients. This method concurrently measures multiple peptide phosphorylation rates to provide a diagnostic fingerprint pattern for activated kinases, protein phosphatases, modulators of these enzymes, and pathways (kinome) from as little starting material as a few cells.

6 Claims, 52 Drawing Sheets

Specification includes a Sequence Listing.

PREDICTED FRAGMENTATION PATTERN

| +1 | | | | | +2 | | | | |
|---|---|---|---|---|---|---|---|---|---|
| Seq | # | b | y | +1 | Seq | # | b | y | +1 |
| E | 1 | 130.05 | ... | 13 | E | 1 | 65.53 | ... | 13 |
| Y | 2 | 293.11 | 1731.75 | 12 | Y | 2 | 147.06 | 866.38 | 12 |
| D | 3 | 408.14 | 1568.68 | 11 | D | 3 | 204.57 | 784.85 | 11 |
| R | 4 | 564.24 | 1453.66 | 10 | R | 4 | 282.62 | 727.33 | 10 |
| L | 5 | 677.33 | 1297.56 | 9 | L | 5 | 339.17 | 649.28 | 9 |
| Y* | 6 | 920.36 | 1184.47 | 8 | Y* | 6 | 460.68 | 592.74 | 8 |
| E | 7 | 1049.40 | 941.44 | 7 | E | 7 | 525.20 | 471.22 | 7 |
| E | 8 | 1178.44 | 812.40 | 6 | E | 8 | 589.72 | 406.70 | 6 |
| Y | 9 | 1341.50 | 683.36 | 5 | Y | 9 | 671.26 | 342.18 | 5 |
| T | 10 | 1442.55 | 520.29 | 4 | T | 10 | 721.78 | 260.65 | 4 |
| P | 11 | 1539.60 | 419.25 | 3 | P | 11 | 770.31 | 210.13 | 3 |
| F | 12 | 1686.67 | 322.19 | 2 | F | 12 | 843.84 | 161.60 | 2 |
| R | 13 | ... | 175.12 | 1 | R | 13 | ... | 88.07 | 1 |

RT=20.47 min

| SEQUENCE | Xcorr |
|---|---|
| EYDRLyEEYTPFR | (2.65) Ascore = 19.2 P = 0.01 |
| EyDRLYEEYTPFR | (2.48) |
| EYDRLYEEyTPFR | (1.28) |
| EYDRLYEEYtPFR | (0.60) |

| | | | |
|---|---|---|---|
| P55G_HUMAN | SKEYDRLYEEYTRTS | P85A_HUMAN | SREYDRLYEEYTRTS |
| P55G_BOVINE | SKEYDRLYEEYTRTS | P85A_BOVINE | SREYDRLYEDYTRTS |
| P55G_MOUSE | SKEYDRLYEEYTRTS | P85A_MOUSE | SREYDRLYEEYTRTS |
| P55G_RAT | SKEYDRLYEEYTRTS | P85A_RAT | SREYDRLYEEYTRTS |
| | | P85AA_XENLA | NQEYDRLYEDYTRTS |
Figure 12A
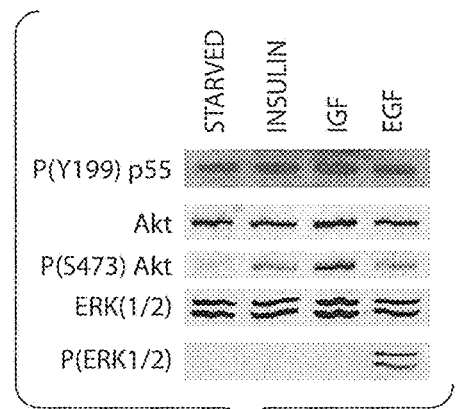
Figure 12B
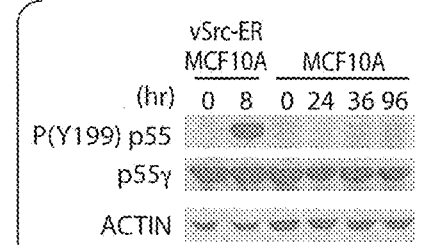
Figure 12C
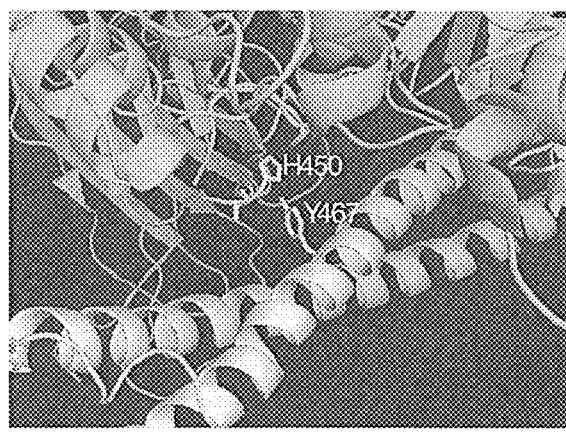
Figure 12D

| | NUMBER |
|---|---|
| LC-MS/MS RUN | 37 |
| TOTAL INSTRUMENT TIME (hr) | 46.25 |
| MS/MS SPECTRUM | 351,907 |
| TOTAL IDENTIFIED MS/MS | 138,917 |
| UNIQUE PEPTIDE | 29,028 |
| PROTEIN | 3,928 |
| KINASE | 116 |

US 10,407,712 B2

METHODS, COMPOSITIONS AND KITS FOR HIGH THROUGHPUT KINASE ACTIVITY SCREENING USING MASS SPECTROMETRY AND STABLE ISOTOPES

RELATED APPLICATIONS

This application is a continuation of and claims the benefit of U.S. utility application Ser. No. 13/078,203 filed Apr. 1, 2011 which is a continuation of and claims the benefit of PCT application number PCT/US2009/059329 filed Oct. 2, 2009, which claims the benefit of U.S. provisional application 61/195,096 filed Oct. 3, 2008 in the U.S. Patent and Trademark Office, both of which are hereby incorporated herein by reference in their entireties.

GOVERNMENT SUPPORT

This work was supported in part by grant from the National Institutes of Health (HG3456). The government has certain rights in the invention.

TECHNICAL FIELD

The invention relates to compositions, kits and methods for diagnosis, research and prognosis of cancer and other conditions, by analyzing the entire kinome of cells and tissues.

BACKGROUND

Most cellular signaling pathways are regulated by post-translational modification of proteins, particularly phosphorylation. Reversible protein phosphorylation is found throughout eukaryotes (Hanahan et al. 2000 Cell 100: 57-70). The hallmark of many cancers is the constitutive activation of one or more of a small number of core signaling cascades including the phosphatidylinositol 3-kinase (PI3K) and mitogen-activated protein (MAP) kinase pathways.

Hyperactivation of signalling pathways occurs during tumor pathogenesis as a result of over-expression of signal activators, structural alteration of kinases, or loss of negative mediators (growth factor receptor, Ras, PI3K, Src, BCR-Abl, PTEN, LKB1 and SHP2; Hanahan et al. 2000 Cell 100: 57-70; McLendon et al. 2008 Nature 455: 1061-1068; Ren et al. 2005 Nat Rev Cancer 5: 172-183; Yeatman 2004 Nat Rev Cancer 4: 470-480). As a consequence, the network is rewired and a new equilibrium is established that can involve retuning sensitivity to upstream signals, bypassing routes and creation of additional nodes and connections. Cells at a later time acquire self-sufficiency in growth signals and limitless replicative potential and become insensitive to antigrowth and apoptosis signals (Hanahan et al. 2000 Cell 100: 57-70; Irish et al. 2004 Cell 118: 217-228).

For example, overexpression of epidermal growth factor receptor (EGFR) is observed in many cancers. In the case of human breast cancer, EGFR is amplified in 20-30% of the patients, and is often associated with inappropriate activation of the anti-apoptotic Ras-Raf-MEK-MAPK cascade, eventually resulting in uncontrolled cell proliferation. Ras per se is present as structurally altered forms in about 25% of human tumors, leading to constitutive activation and disengagement of this protein from the upstream mitogenic signals (Medema et al. 1993 Crit Rev Oncog 4: 615-661). One of the Ras-Raf-MAPK pathway controlled kinases, RSK, is upregulated in about 30% of all cancers and 9% of breast cancers (Barlund et al. 2000 J Natl Cancer Inst 92: 1252-1259).

Overexpression or constitutive activation of a receptor tyrosine kinase (RTK) is often a transformative event in oncogenesis (Krause et al. 2005 N Engl J Med 353: 172-187; Sebolt-Leopold et al. 2006 Nature 441: 457-462). In addition, RTK-independent activation of the phosphatidylinositol 3-kinase (PI3K) and mitogen-activated protein (MAP) kinase pathways are two of the most frequent epidemiological observations in human malignancy (i.e. phosphatase and tensin homolog (PTEN) loss of function and K-Ras gain of function, respectively). Several kinase inhibitors have been approved as drugs and more than 200 others are in development. Therefore knowledge of the genetic insult and the activation state of oncogenic kinase pathways will be crucial to proper therapy decisions.

Signaling networks in cancer cells are heterogeneous. Individual tumors derived from the same types of precursor cells may have distinct substructures within the network. In order to gain understanding of the scope of kinase signaling pathways, there is a need for a fast and convenient method to characterize not only the basal phosphorylation activities but also the manner in which protein kinases and protein phosphatases and their downstream targets perform in the pathway.

SUMMARY OF THE EMBODIMENTS

An embodiment of the invention provided herein is a composition having an optimized oligopeptide substrate having an amino acid sequence, such that a site in the amino acid sequence is recognized and phosphorylated by a protein kinase, or is recognized and dephosphotylated by a protein phosphatase, and further having at least one modification for purification and analysis by mass spectrometry (MS). In alternative embodiments, the modification for purification has at least one hydrophobic amino acid at a terminus of the amino acid sequence, or the modification for purification includes at least one hydrophobic amino acid at an interior position within the amino acid sequence.

In general in the composition, the at least one hydrophobic amino acid is selected from the group including phenylalanine, leucine, tryphtophan, valine, and isoleucine.

Further, in general, the modification for analysis by MS includes a charged amino acid. For example, the charged amino acid is selected from the group of arginine, lysine and histidine, more particularly, arginine and lysine. In general, the modification includes amino acids arginine-phenylalanine located at the carboxy terminus of the amino acid sequence of the oligopeptide.

Also provided herein is the oligopeptide composition including an amino acid sequence of a protein kinase substrate chemically bound to a tri-peptide sequence proline-phenylalanine-arginine (PFR). For example, the PFR tripeptide is located at the carboxy terminal end. In general, the kinase substrate includes at least one amino acid for phosphorylation selected from the group serine, threonine, and tyrosine (S, T or Y), i.e., the oligopeptide that is a kinase substrate contains at least one amino acid residue capable of being phosphorylated and thus having a hydroxy group. The oligopeptide sequences are shown in Tables 1 and 2.

Also provided is an oligopeptide composition for prognosing and diagnosing a cancer, and the oligopeptide is any of the peptides according to any of the above described compositions. An embodiment of the oligopeptide includes at least one phosphorylated amino acid. Alternatively, the amino acids of the sequence are not phosphorylated.

In another embodiment of the oligopeptide composition above, at least one amino acid in the sequence is a labeled amino acid having at least one atom which is enriched in stable isotopes of increased molecular mass compared to common isotopes. For example, the stable isotope is at least one selected from the group of $^2$H, $^{13}$C and $^{15}$N. Further, the labeled amino acid is a proline located at or near the carboxy terminus.

An embodiment of the composition includes a plurality of the above described optimized kinase substrates, such that the substrates have amino acid sequences selected for kinases associated with a class of diseases selected from the group of cancers, cardiac conditions, and inflammatory conditions. Alternatively, the plurality of sequences are associated with a plurality of classes of diseases, such that the compositions can be used in analyzing an overall profile of the health of a subject.

Accordingly, an embodiment of the invention provides a method for simultaneously measuring a plurality of kinase-related enzyme activities in at least one biological sample, the method including: contacting an aliquot of the at least one sample with a plurality of optimized peptide substrates under reaction conditions suitable for the plurality of kinase-related enzyme activities, each optimized substrate including an amino acid sequence including a phosphorylation site, and amino acid modifications for enrichment and for mass spectrometry (MS); terminating the reaction and adding a plurality of internal standards, wherein the internal standards include amino acid sequences corresponding to amino acid sequences of the peptide substrates, wherein at least one end terminal amino acid of each internal standard further includes label with a heavy stable isotope; enriching phosphopeptide reaction products by immobilized metal ion affinity chromatography or titanium dioxide interaction chromatography, wherein prior to enriching the sample is passaged through a C18 solid phase extraction cartridge; and, analyzing reaction products by ultra-high resolution MS, wherein a plurality of reaction products and internal standards are detected and measured.

An embodiment of the method above involves a single incubation measuring the plurality of kinase-related enzyme activities performed in a single container. The method further reduces a cross-phosphorylation of the peptide substrates. For example, the method reduces the cross-phosphorylation wherein an optimized substrate concentration is less than about 5 µM or less than about 1 µM.

An embodiment of the method above includes the plurality having at least 10 enzyme activities; at least 50 enzyme activities; or the plurality is at least 100 enzyme activities.

An embodiment of the method above includes at least one aliquot that is a mixture of at least five samples or at least 10 samples, i.e., the method can multiplex the assays so that mixtures of biological samples can be made and assayed in the same tube.

At least one biological sample in general is selected from the group of biological fluids comprising: a cell lysate, a tissue homogenate, urine, saliva, tears, sweat, blood, lymph, serum, spinal fluid, vaginal fluid, semen, and milk, and these fluids are exemplary so that any fluid can be assayed. Further exemplary biological fluid is obtained from a subject that is mammalian or avian, although any biological material is suitable, including plant materials, bacterial cultures, and environmental samples. Because the kinome can be used as a profile of health, in general the subject is a mammal selected from the group of human, rodent, canine, feline, equine, agricultural animal, and high value zoo animal.

In general, the kinase-related enzyme activities includes a profile of at least one enzyme type selected from the group of protein kinases, protein phosphatases, and inhibitors and modulators of activities thereof. For example, the enzyme activities are protein kinases. Alternatively, the activities are protein phosphotases. The method in further embodiment associates at least one protein kinase with at least one specific substrate in the kinase-related enzyme profile.

Accordingly in the embodiment in which the enzyme activities are protein kinases, the substrates are unphosphorylated and the internal standards are phosphorylated. For example, after terminating the reaction, enriching further involves depleting the sample of unphosphorylated substrates by performing the immobilized metal affinity ion chromatography.

Alternatively, the enzyme activities are protein phosphatases, in which embodiment the substrates are phosphorylated and the internal standards are unphosphorylated. For example, after terminating the reaction, enriching further involves depleting the sample of phosphorylated substrates by immobilized metal ion affinity chromatography.

Thus an embodiment of the invention provides a method for determining a kinase activation pattern for a cancer or tumor, the method including: contacting an aliquot of a first biological sample with a plurality of optimized peptide substrates under conditions suitable for reaction of the plurality of kinase activities, wherein each optimized substrate includes an amino acid sequence including a kinase phosphorylation site and an end terminal amino acid sequence modification for enhanced enrichment and mass spectrometry; adding a plurality of internal standards to the reaction, each having at least one phosphorylated amino acid, and corresponding in sequence to the peptide substrates and further including an end terminal amino acid labeled with a heavy stable isotope; enriching phosphopeptide reaction products and internal standards by immobilized metal ion affinity chromatography of the reaction, titanium dioxide affinity chromatography or the like; and, analyzing reaction products by ultra-high resolution mass spectrometry, wherein a plurality of reaction products and internal standards are detected and measured, thereby generating a first kinase activation pattern for the sample, and comparing the first kinase activation pattern to second kinase activation pattern for a second biological sample, wherein the second biological sample is selected from the group consisting of an early stage dystrophic tissue, a polyp, a potential tumor or an advanced stage cancer tissue, and the first biological sample is obtained from tissue that is normal.

In general in the above method, the second biological sample is selected from the group of: a biopsy, an autopsy, an archival sample, a cell culture, and a tissue culture. In this embodiment, the first sample may be a normal tissue, or a tissue from a different subject that is normal. Alternatively, the first sample and the second sample are from different members of a family. Alternatively, the first and second samples are from cell cultures grown under different conditions. For example, the different conditions are presence and absence, respectively, of at least one agent selected from the group of: chemotherapeutic agent; mitogen; tumor promoter; kinase inhibitor; phosphatase inhibitor; protease inhibitor; modulator of kinase expression; and modulator of phosphatase expression.

Alternatively, the first and second samples are from cell cultures and are obtained at different time points.

Alternatively, the first and second samples are taken from the same subject at different time points in the course of treatment, and the method further comprises prognosis of success of the treatment.

In general, analyzing reaction products is analyzing at least about five, ten, 50, 90 or more enzyme activities. For example, the at least about five enzyme activities are kinases associated with a condition selected from the group of: cancer, cardiac disease, and inflammation. Alternatively, the activities are phosphotases.

In an embodiment of the method above, a prognosis of success of the treatment further includes altering a course of chemotherapy. Alternatively, a prognosis of success further includes maintaining the subject on the same course of chemotherapy.

Also provided herein is a kit for kinome activity assay for measuring a plurality of enzymes involved in kinase pathways (KAYAK), the kit including a plurality of optimized oligopeptide kinase substrates for the plurality of enzymes, each oligopeptide having an amino acid sequence including a protein kinase substrate and an end terminal modification for enrichment of a reaction product and enhanced mass spectrometry, the kit further including a plurality of internal standards, each of the internal standards having an amino acid sequence corresponding to the respective substrate, such that the respective internal standard is phosphorylated and further includes an end terminal amino acid labeled with a heavy isotope.

The kit in one embodiment includes that the end terminal modification includes at least one hydrophobic amino acid located at the carboxy terminal end. Exemplary amino acid sequences are selected from the group shown in Tables 1 and 2. Embodiments of the kit further include a container and instructions for use.

An exemplary embodiment of the kit includes the plurality of optimized kinase substrates and corresponding internal standards which are selected as prognostic and diagnostic of a course of a cancer, a cardiac condition, or an inflammatory condition, wherein the plurality of kinases are assayed simultaneously and provide a profile of the kinome of a sample.

BRIEF DESCRIPTION OF DRAWINGS

FIG. 1A is a drawing showing an overview of the procedure in which 90 synthetic peptides are used as substrates for in vitro kinase assays.

FIG. 1B is an example of a high resolution mass spectrum (MS) and elution chromatogram observed for a light and heavy pair of phosphopeptides. Asterisk indicates presence of a proline residue containing heavy isotopes.

FIG. 1C is a heat map representation of average activity of triplicate measurements observed from starved HEK293 cell lysates toward each of the 90 peptides. Activities are represented in $Log_2$ space. Dark gray cells represent those with an activity of lower than 1 fmol/µg/min (considered not detected, ND).

FIG. 1D is a photograph of an immunoblotting analysis (Western) of insulin and EGF stimulated HEK293 cells for each of proteins P(S473)Akt, Akt, P(ERK1/2), and ERK1/2.

FIG. 1E is a bar graph with examples of observed phosphorylation rates (performed in triplicate) for peptides A3 (RPRAAtFPFR; SEQ ID NO: 1) and B6 (PKRKVsSAEGPFR; SEQ ID NO: 16) using the HEK293 cell lysates from cells as in FIG. 1D.

FIG. 1F is a line graph showing a time course of substrate A3 phosphorylation using the cell lysates from cells treated as in FIG. 1D.

The material in computer readable form ASCII text file (24 kilobytes) created May 19, 2011 entitled "36373-044_SeQListing", containing sequence listings numbers 1-96 has been electronically filed herewith and is incorporated by reference herein in its entirety.

Figure 2A:
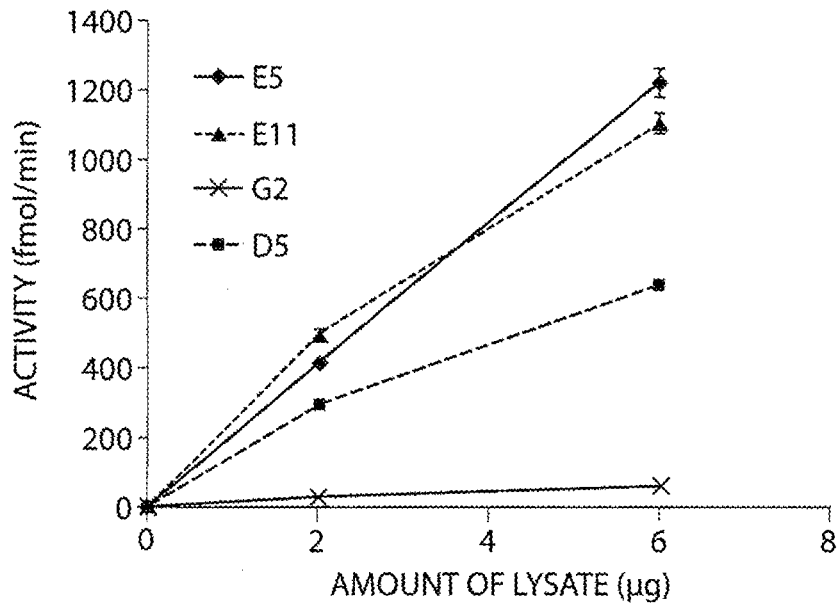
Figure 2B:
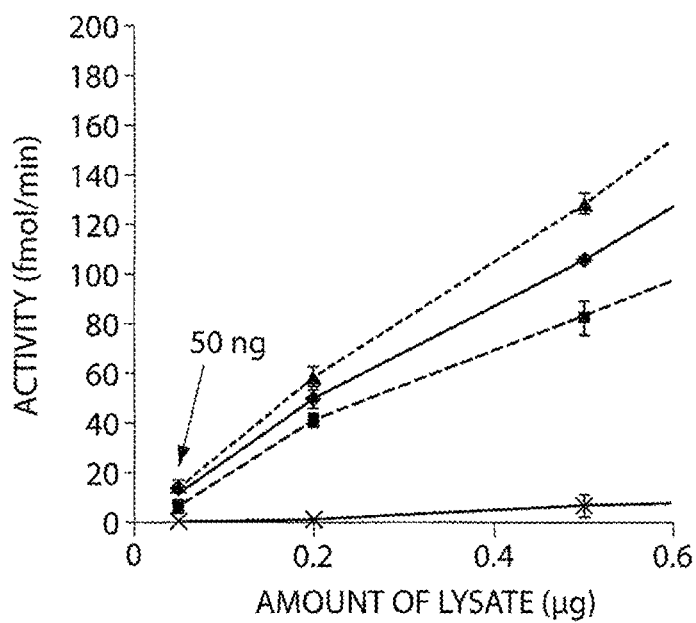
Figure 2C:
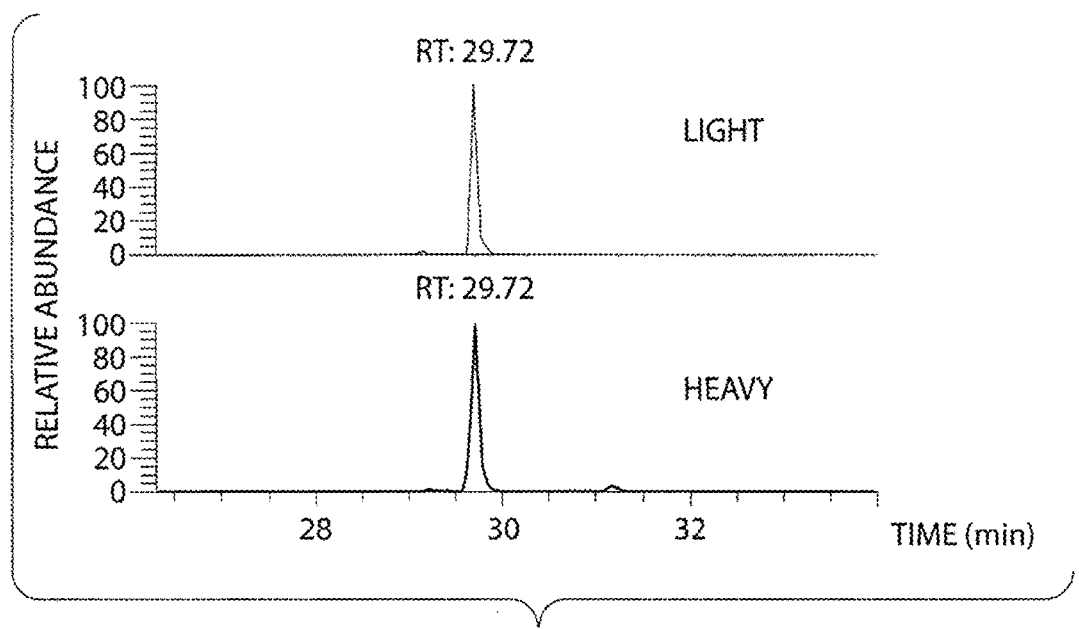

FIGS. 2A-2C are a set of line graphs and an extracted ion chromatogram showing sensitivity of the KAYAK method.

FIG. 2A is a line graph showing that activity of a lysate using several peptides as substartes was measured using as little as 50 ng of the crude lysate of insulin-stimulated HEK293 cells. The KAYAK assay was performed as a function of amount of cell lysate. Substrate peptide responses were observed to be linear from 50 ng to 6 micrograms.

FIG. 2B is an expanded view of the data using low amount of lysate shown in FIG. 2A.

FIG. 2C is an extracted ion chromatogram of the light and heavy phospho-E11 peptide using 50 ng of the lysate.

Figure 3A:
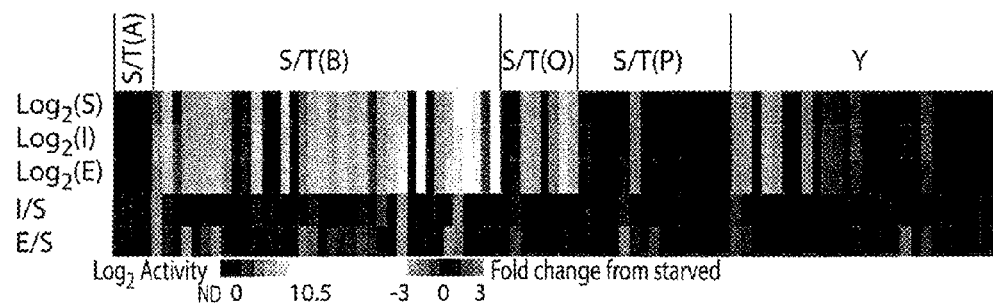
Figure 3B:
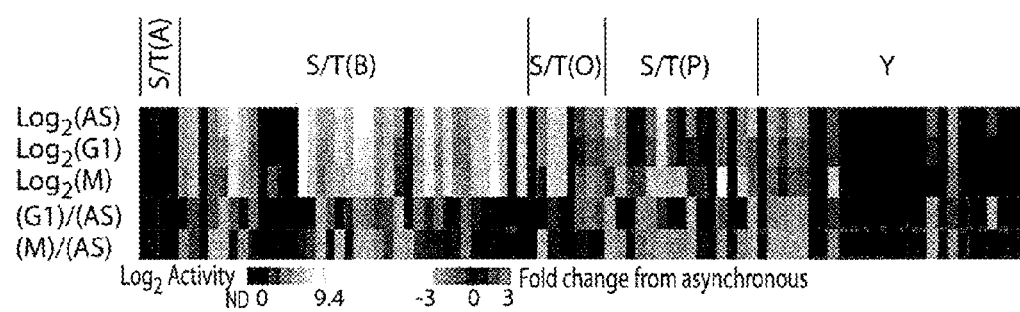

FIGS. 3A and 3B are a set of heat maps of kinase activities profiled by KAYAK method.

FIG. 3A shows kinase activities of starved (S), insulin-stimulated (I) and EGF-stimulated (E) HEK293 cells. Activities (expressed in fmol/µg lysate/minute) were highly dynamic and are displayed on a $Log_2$ scale. Lines (I/S) and (E/S) represent the ratio of activities for (insulin-stimulated)/(starved) and (EGF-stimulated)/(starved) (fold-change compared to starved state), respectively.

FIG. 3B shows $Log_2$-converted kinase activities of asynchronously growing (AS) HeLa cells, and cells arrested in either G1/S or G2/M phase using double thymidine block and nocodazole, respectively. Lines (G1)/(AS) and (M)/(AS) represent the ratio of activities for G1/S and G2/M compared with asynchronous (fold-change compared to asynchronous), respectively. Peptides were categorized into different groups based on the flanking sequences of the phosphorylated Ser/Thr and Tyr. S/T(A), S/T(B), S/T(P), S/T(O) and Y indicate the acidic peptides, basic, proline-directed, other Ser/Thr and Tyr peptides, respectively (see Table 1). Dark gray cells represent those with signal below the arbitrary quantification threshold (activity<1 fmol/µg/min). Medium gray and lighter medium gray cells represent the ones with increased and decreased activities compared with the control group, respectively.

TABLE 1

Sequences of the peptides used in the KAYAK assay

| Lab Code | Substrate * | Internal standard ** | Category *** | Swiss-Prot ID | Protein name (Kinase) | SEQ ID NO |
|---|---|---|---|---|---|---|
| A3 | RPRAATFPFR | RPRAAtFpFR | S/T(B) | AKTIDE | Aktide (Akt) | 1 |
| A4 | GPLAGSPVIAPFR | GPLAGsPVIApFR | S/T(P) | SWISS; P19138; P20426; KC21_HUMAN | csnk2a1 protein (CDK) | 2 |
| A5 | LPGGSTPVSSPFR | LPGGStPVSSpFR | S/T(P) | SWISS; P19138; P20426; KC21_HUMAN | csnk2a1 protein (CDK) | 3 |
| A6 | RPGPQSPGSPPFR | RPGPQsPGSPpFR | S/T(P) | SWISS; P14598; NCF1_HUMAN | neutrophil cytosol factor 1 | 4 |
| A7 | VGGAGYKPQLPFR | VGGAGyKPQLpFR | Y | SWISS; P42702; LIFR_HUMAN | leukemia inhibitory factor receptor precursor | 5 |
| A8 | GPGVNYSGLQPFR | GPGVNYsGLQpFR | S/T(O) | SWISS; P40763; STAT3_HUMAN | signal transducer and activator of transcription 3 | 6 |
| A9 | EPLTPSGEAPPFR | EPLtPSGEAPpFR | S/T(P) | SWISS; P00533; P06268; EGFR_HUMAN | epidermal growth factor receptor precursor | 7 |
| A10 | TPPSAYGSVKPFR | TPPSAyGSVKpFR | Y | SWISS; P07355; ANX2_HUMAN | annexin a2 (Src) | 8 |
| A11 | APKKGSKKAVPFR | APKKGsKKAVpFR | S/T(B) | SWISS; P02278; H2B_HUMAN | histone h2b (PKA) | 9 |
| A12 | PSTNSSPVLKPFR | PSTNSsPVLKpFR | S/T(P) | SWISS; ESPL1; ESPL1_HUMAN | Separin (CDK) | 10 |
| B1 | GSAAPYLKTKPFR | GSAAPyLKTKpFR | Y | SWISS; P40763; STAT3_HUMAN | signal transducer and activator of transcription 3 | 11 |
| B2 | KKASFKAKKPFR | KKAsFKAKKpFR | S/T(B) | Peptide KKASFKAKK | peptide KKASFKAKK (PKC) | 12 |
| B3 | AKTRSSRAGLPFR | AKTRSsRAGLpFR | S/T(B) | SWISS; P02261; H2A1_HUMAN | histone h2a (PKA) | 13 |
| B4 | IPINGSPRTPPFR | IPINGsPRTPpFR | S/T(P) | SWISS; P06400; RB_HUMAN | retinoblastoma-associated protein (CDK) | 14 |
| B5 | NQDPVSPSLVPFR | NQDPVsPSLVpFR | S/T(P) | SWISS; P08172; ACM2_HUMAN | muscarinic acetylcholine receptor m2 (MAPK) | 15 |
| B6 | PKRKVSSAEGPFR | PKRKVsSAEGpFR | S/T(B) | SWISS; P05114; HMGN1_HUMAN | nonhistone chromosomal protein hmg-14 (RSK) | 16 |
| B7 | VKRQSSTPSAPFR | VKRQSsTPSApFR | S/T(B) | SWISS; Q93100; KPBB_HUMAN | phosphorylase b kinase regulatory subunit beta (CDK) | 17 |
| B8 | TPSLPTPPTRPFR | TPSLPtPPTRpFR | S/T(P) | SWISS; P10636; UPSP: TAU_HUMAN | microtubule-associated protein tau | 18 |
| B9 | RTPKDSPGIPPFR | RTPKDsPGIPpFR | S/T(P) | SWISS; KS6A1; RSK_HUMAN | ribosomal protein s6 kinase alpha-1 (ERK) | 19 |
| B10 | TKRNSSPPPSPFR | TKRNSsPPPSpFR | S/T(P) | SWISS; P20020; ATCP_HUMAN | plasma membrane calcium transporting atpase 1 (PKA) | 20 |
| B11 | LKLSPSPSSRPFR | LKLSPsPSSRpFR | S/T(P) | SWISS; P20700; LAM1_HUMAN | lamin-b1 (CDK) | 21 |
| B12 | VPPSPSLSRHPFR | VPPSPsLSRHpFR | S/T(O) | SWISS; P13807; GYS1_HUMAN | glycogen [starch] synthase (CKI) | 22 |

TABLE 1-continued

Sequences of the peptides used in the KAYAK assay

| Lab Code | Substrate * | Internal standard ** | Category *** | Swiss-Prot ID | Protein name (Kinase) | SEQ ID NO |
|---|---|---|---|---|---|---|
| C1 | PKGTGYIKTEPFR | PKGTGyIKTEpFR | Y | SWISS; P42224; STA1_HUMAN | signal transducer and activator of transcription 1-alpha/beta | 23 |
| C2 | IPTGTTPQRKPFR | IPTGTtPQRKpFR | S/T(P) | SWISS; P52732; EG5_HUMAN | kinesin-like protein kif11 (kinesin-related motor protein eg5) (CDK) | 24 |
| C3 | GLPKSYLPQTPFR | GLPKSyLPQTpFR | Y | SWISS; P40189; IL6RB_HUMAN | interleukin-6 receptor beta chain precursor | 25 |
| C4 | DSARVYENVGPFR | DSARVyENVGpFR | Y | SWISS; Q06124; PTNB_HUMAN | tyrosine-protein phosphatase non-receptor type 11 | 26 |
| C5 | LLKLASPELEPFR | LLKLAsPELEpFR | S/T(P) | SWISS; P05412; AP1_HUMAN | transcription factor jun-d (CDK) | 27 |
| C6 | TKRSGSVYEPPFR | TKRSGsVYEPpFR | S/T(B) | SWISS; Q93100; KPBB_HUMAN | phosphorylase b kinase regulatory subunit beta (RSK) | 28 |
| C7 | LKKLGSKKPQPFR | LKKLGsKKPQpFR | S/T(B) | SWISS; Q9y5y9; SC10A_HUMAN | sodium channel protein type 10 subunit alpha (PKC) | 29 |
| C8 | GKAKVTGRWKPR | GKAKVtGRWKpFR | S/T(B) | SWISS; P45379; TNNT2_HUMAN | troponin t (PKC) | 30 |
| C9 | KKSKISASRKPFR | KKSKIsASRKpFR | S/T(B) | SWISS; P19429; TNNI3_HUMAN | troponin I (PKC) | 31 |
| C10 | AENAEYLRVAPFR | AENAEyLRVApFR | Y | SWISS; P00533; EGFR_HUMAN | epidermal growth factor receptor precursor | 32 |
| C11 | NKRRGSVPILPFR | NKRRGsVPILpFR | S/T(B) | SWISS; P16452; 42_HUMAN | erythrocyte membrane protein band 4.2 (RSK) | 33 |
| C12 | HLLAPSEEDHPFR | HLLAPsEEDHpFR | S/T(A) | SWISS; P08833; IBP1_HUMAN | insulin-like growth factor-binding protein 1 precursor | 34 |
| D1 | RKTTASTRKVPFR | RKTTAsTRKVpFR | S/T(B) | SWISS; P13569; CFTR_HUMAN | cystic fibrosis transmembrane conductance regulator (PKC) | 35 |
| D2 | APPRRSSIRNPFR | APPRRsSIRNpFR | S/T(B) | SWISS; P14598; NCF1_HUMAN | neutrophil cytosol factor 1 | 36 |
| D3 | KLSGFSFKKNPFR | KLSGFsFKKNpFR | S/T(O) | SWISS; P29966; MACS_HUMAN | myristoylated alanine-rich c-kinase substrate (PKC) | 37 |
| D4 | LKIQASFRGHPFR | LKIQAsFRGHpFR | S/T(O) | SWISS; Q92686; NEUG_HUMAN | neurogranin (PKC) | 38 |
| D5 | IKRFGSKAHLPFR | IKRFGsKAHLpFR | S/T(B) | SWISS; P29475; NOS1_HUMAN | nitric-oxide synthase, brain (PKA) | 39 |
| D6 | SPQPEYVNQPPFR | SPQPEyVNQPpFR | Y | SWISS; P04626; ERB2_HUMAN | receptor tyrosine-protein kinase erbb-2 | 40 |
| D7 | NLLPLSPEEFPFR | NLLPLsPEEFpFR | S/T(P) | SWISS; P42224; STA1_HUMAN | signal transducer and activator of transcription 1-alpha/beta (MAPK) | 41 |
| D8 | LPVPEYINQSPFR | LPVPEyINQSpFR | Y | SWISS; P00533; P06268; EGFR_HUMAN | epidermal growth factor receptor precursor (EGFR) | 42 |

TABLE 1-continued

Sequences of the peptides used in the KAYAK assay

| Lab Code | Substrate * | Internal standard ** | Category *** | Swiss-Prot ID | Protein name (Kinase) | SEQ ID NO |
|---|---|---|---|---|---|---|
| D9 | VKSRWSGSQQPFR | VKSRWsGSQQpFR | S/T(B) | SWISS; P04049; KRAF_HUMAN | raf proto-oncogene serine/threonine-protein kinase (PKC) | 43 |
| D10 | FKNIVTPRTPPFR | FKNIVtPRTPpFR | S/T(P) | SWISS; P02686; MBP_HUMAN | myelin basic protein (CDK) | 44 |
| D11 | REVGDYGQLHPFR | REVGDyGQLHpFR | Y | SWISS; O60674; JAK2_HUMAN | tyrosine-protein kinase jak2 | 45 |
| D12 | RPQRATSNVFPFR | RPQRAtSNVFpFR | S/T(B) | SWISS; P24844; MLRN_HUMAN | myosin regulatory light chain 2 | 46 |
| E1 | EPEGDYEEVLPFR | EPEGDyEEVLpFR | Y | SWISS; P14317; HS1_HUMAN | hematopoietic lineage cell-specific protein | 47 |
| E2 | FDDPSYVNVQPFR | FDDPSyVNVQpFR | Y | SWISS; P29353; SHC1_HUMAN | shc-transforming protein 1 | 48 |
| E3 | KRKQISVRGLPFR | KRKQIsVRGLpFR | S/T(B) | SWISS; P11217; PHS2_HUMAN | glycogen phosphorylase | 49 |
| E4 | LLRGPSWDPFPFR | LLRGPsWDPFpFR | S/T(B) | SWISS; P04792; HS27_HUMAN | heat-shock protein beta-1 (MAPKAPK2) | 50 |
| E5 | LKRSLSELEIPFR | LKRSLsELEIpFR | S/T(B) | SWISS; P11831; SRF_HUMAN | serum response factor | 51 |
| E6 | PQEGLYNELQPFR | PQEGLyNELQpFR | Y | SWISS; P20963; CD3Z_HUMAN | t-cell surface glycoprotein cd3 zeta chain precursor (Lck/Fyn) | 52 |
| E7 | LLRLFSFKAPPFR | LLRLFsFKAPpFR | S/T(B) | SWISS; Q6PCC3_HUMAN | gamma-aminobutyric acid a receptor, gamma 2, isoform 1 (PKC) | 53 |
| E8 | VQNPVYHNQPPFR | VQNPVyHNQPpFR | Y | SWISS; P00533; EGFR_HUMAN | epidermal growth factor receptor precursor | 54 |
| E9 | EKRKNSILNPPFR | EKRKNsILNPpFR | S/T(B) | SWISS; P13569; CFTR_HUMAN | cystic fibrosis transmembrane conductance regulator (PKA) | 55 |
| E10 | AKKRLSVERIPFR | AKKRLsVERIpFR | S/T(B) | SWISS; P11388; TOPA_HUMAN | dna topoisomerase 2-alpha (PKC) | 56 |
| E11 | RKRLISSVEDPFR | RKRLIsSVEDpFR | S/T(B) | SWISS; P49815; Tuberin_HUMAN | tuberin (RSK, Akt) | 57 |
| E12 | LFPRNYVTPVPFR | LFPRNyVTPVpFR | Y | SWISS; P62993; GRB2_HUMAN | growth factor receptor-bound protein 2 | 58 |
| F1 | VRRFNTANDDPFR | VRRFNtANDDpFR | S/T(B) | SWISS; P29474; NOS3_HUMAN | nitric-oxide synthase, | 59 |
| F2 | KKGQESFKKQPFR | KKGQEsFKKQpFR | S/T(B) | SWISS; P06748; NPM_HUMAN | nucleophosmin (PKC) | 60 |
| F3 | FLQRYSSDPTPFR | FLQRYsSDPTpFR | S/T(A) | SWISS; P00533; P06268; EGFR_HUMAN | epidermal growth factor receptor precursor | 61 |
| F4 | RKLKDTDSEEPFR | RKLKDtDSEEpFR | S/T(A) | SWISS; P02593; CALM_HUMAN | calm1 protein (CKII) | 62 |
| F5 | RTYSLGSALRPPFR | RTYSLGsALRPpFR | S/T(O) | SWISS; P08670; VIME_HUMAN | vimentin | 63 |
| F6 | RIRTQSFSLQPFR | RIRTQsFSLQpFR | S/T(B) | SWISS; P29474; NOS3_HUMAN | nitric-oxide synthase (RSK, Akt) | 64 |
| F7 | EPENDYEDVEPFR | EPENDyEDVEpFR | Y | SWISS; P14317; HS1_HUMAN | hematopoietic lineage cell-specific protein | 65 |

TABLE 1-continued

Sequences of the peptides used in the KAYAK assay

| Lab Code | Substrate * | Internal standard ** | Category *** | Swiss-Prot ID | Protein name (Kinase) | SEQ ID NO |
|---|---|---|---|---|---|---|
| F8 | KPKDASQRRRPFR | KPKDAsQRRRpFR | S/T(B) | SWISS; P12931; SRC_HUMAN | proto-oncogene tyrosine-protein kinase src (PKC) | 66 |
| F9 | LLSELSRRRIPFR | LLSELsRRRIpFR | S/T(O) | SWISS; P05198; IF2A_HUMAN | eukaryotic translation initiation factor 2 subunit 1 | 67 |
| F10 | KLRKVSKQEEPFR | KLRKVsKQEEpFR | S/T(B) | SWISS; P50552; VASP_HUMAN | vasodilator-stimulated phosphoprotein (PKA) | 68 |
| F11 | RKGHEYTNIKPFR | RKGHEyTNIKpFR | Y | SWISS; Q06124; PTNB_HUMAN | tyrosine-protein phosphatase non-receptor type 11 | 69 |
| F12 | VKRRDYLDLAPFR | VKRRDyLDLApFR | Y | SWISS; P07949; RET_HUMAN | proto-oncogene tyrosine-protein kinase receptor ret precursor | 70 |
| G1 | VLLRPSRRVRPFR | VLLRPsRRVRpFR | S/T(O) | SWISS; P32745; SSR3_HUMAN | somatostatin receptor type 3 | 71 |
| G2 | ELQDDYEDLLPFR | ELQDDyEDLLpFR | Y | SWISS; P02730; B3AT_HUMAN | band 3 anion transport protein | 72 |
| G3 | LDNPDYQQDFPFR | LDNPDyQQDFpFR | Y | SWISS; P00533; EGFR_HUMAN | epidermal growth factor receptor precursor | 73 |
| G4 | TDKEYYTVKDPFR | TDKEyYTVKDpFR | Y | SWISS; P23458; JAK1_HUMAN | tyrosine-protein kinase jak1 | 74 |
| G5 | SKRRNSEFEIPFR | SKRRNsEFEIpFR | S/T(B) | SWISS; P17752; TPH1_HUMAN | tryptophan 5-hydroxylase 1 (RSK) | 75 |
| G6 | KKKKFSFKKPPFR | KKKKFsFKKPpFR | S/T(B) | SWISS; P49006; MRP_HUMAN | marcks-related protein (PKC) | 76 |
| G7 | RKRRSSSYHVPFR | RKRRSsSYHVpFR | S/T(B) | SWISS; Q99250; SCN2A_HUMAN | sodium channel protein type 2 subunit alpha (PKA) | 77 |
| G8 | FKRRRSSKDTPFR | FKRRRsSKDTpFR | S/T(B) | SWISS; Q05586; P35437; NMZ1_HUMAN | glutamate [nmda] receptor subunit zeta 1 precursor (PKC) | 78 |
| G9 | FKNDKSKTWQPFR | FKNDKsKTWQpFR | S/T(B) | SWISS; P06730; IF4E_HUMAN | eukaryotic translation initiation factor 4e (PKA) | 79 |
| G10 | KKKRFSFKKSPFR | KKKRFsFKKSpFR | S/T(B) | SWISS; P29966; MARCS_HUMAN | myristoylated alanine-rich c-kinase substrate (PKA) | 80 |
| G11 | KKRKRSRKESPFR | KKRKRsRKESpFR | S/T(B) | SWISS; P02278; H2B_HUMAN | histone h2b (PKC) | 81 |
| G12 | IKKSWSRWTLPFR | IKKSWsRWTLpFR | S/T(B) | SWISS; Q03431; PTHR1_HUMAN | parathyroid hormone/parathyroid hormone-related peptide receptor | 82 |
| H1 | HHIDYYKKTTPFR | HHIDYyKKTTpFR | Y | SWISS; P11362; FGFR1_HUMAN | basic fibroblast growth factor receptor 1 precursor | 83 |
| H2 | WPWQVSLRTRPFR | WPWQVsLRTRpFR | S/T(O) | SWISS; P00747; PLMN_HUMAN | apolipoprotein | 84 |
| H3 | HLEKKYVRRDPFR | HLEKKyVRRDpFR | Y | SWISS; P07333; CSF1R_HUMAN | macrophage colony-stimulating factor 1 receptor precursor (c-Fms) | 85 |

TABLE 1-continued

Sequences of the peptides used in the KAYAK assay

| Lab Code | Substrate * | Internal standard ** | Category *** | Swiss-Prot ID | Protein name (Kinase) | SEQ ID NO |
|---|---|---|---|---|---|---|
| H4 | RLRRLSTKYRPFR | RLRRLsTKYRpFR | S/T(B) | SWISS; Q05209; PTNC_HUMAN | tyrosine-protein phosphatase non-receptor type 12 (PKA) | 86 |
| H5 | EYDRLYEEYTPFR | EYDRLyEEYTpFR | Y | SWISS; P27986; P85A_HUMAN | phosphatidylinositol 3-kinase regulatory subunit (Src) | 87 |
| H6 | HTGFLTEYVATRR | HTGFLtEyVATRpR | Y | SWISS; P28482; MK01_HUMAN | mitogen-activated protein kinase 1 (MEK) | 88 |
| H7 | TSFLLTPYVVTRPR | TSFLLtPyVVTRpFRY | Y | SWISS; P45983; MK08_HUMAN | mitogen-activated protein kinase 8 | 89 |
| H8 | IYKNDYYRKRPFR | IYKNDyYRKRpFR | Y | SWISS; P08922; ROS_HUMAN | proto-oncogene tyrosine-protein kinase ros precursor | 90 |

\* Cys and Met were substituted with Leu to avoid oxidation. Sub, substrate. IS, internal standard.
\*\* Low case p and s/t/y indicate the heavy Pro and phosphorylated Ser/Thr/Tyr residues, respectively.
\*\*\* The 90 peptides were categorized into Ser/Thr containing (S/T) or Tyr containing (Y) peptides with the S/T peptides were further classified into different motif groups based on the following binary decision tree, P at +1 (Pro-directed: P), 5 or more E/D at +1 to +6 (acidic: A), R/K at - 3 (basic: B), D/E at +1/+2 or +3 (A), 2 or more R/K at -6 to -1 (B), otherwise (others: O).
Additional information is found in Yu et al. 2009 Proc Natl Acad Sci USA 116: 11606-11611, hereby incorporated herein by reference in its entirety.

FIGS. 4A-4D are a set of bar graphs and photographs of gel electrophoretograms showing example peptides with altered phosphorylation during mitogen stimulation and cell cycle progression.

Figure 4A:
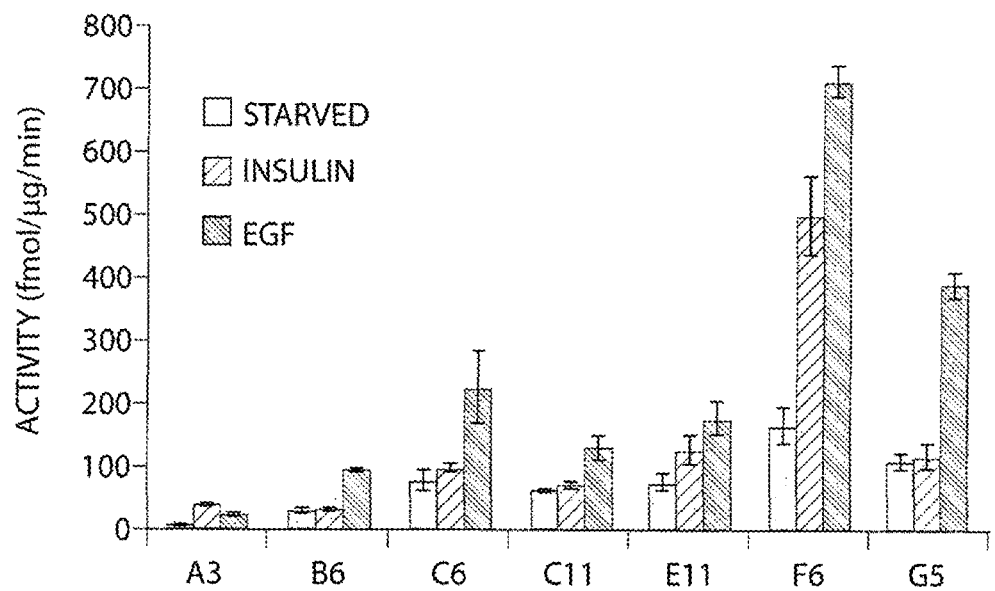

FIG. 4A is a bar graph showing peptides with altered phosphorylation after stimulation of cells with insulin or EGF.

Figure 4B:
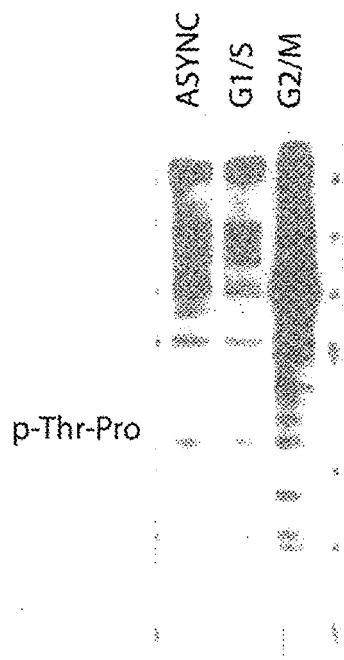

FIG. 4B is a photograph of an immunoblotting analyses of lysates of each of asynchronously growing HeLa cells and cells arrested in G1/S or G2/M phase using a general antibody directed against phospho-threonine-proline motif. Proline-directed phosphorylation was observed to have increased in G2/M phase.

Figure 4C:
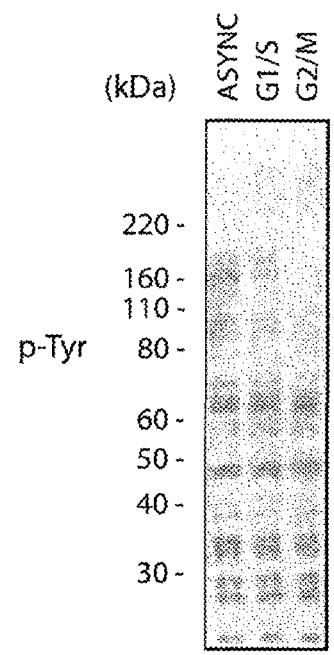

FIG. 4C is a photograph of an immunoblotting analysis of lysates of asynchronously growing HeLa cells and cells arrested in G1/S or in G2/M phase using a general antibody directed against phospho-tyrosine motif.

Figure 4D:
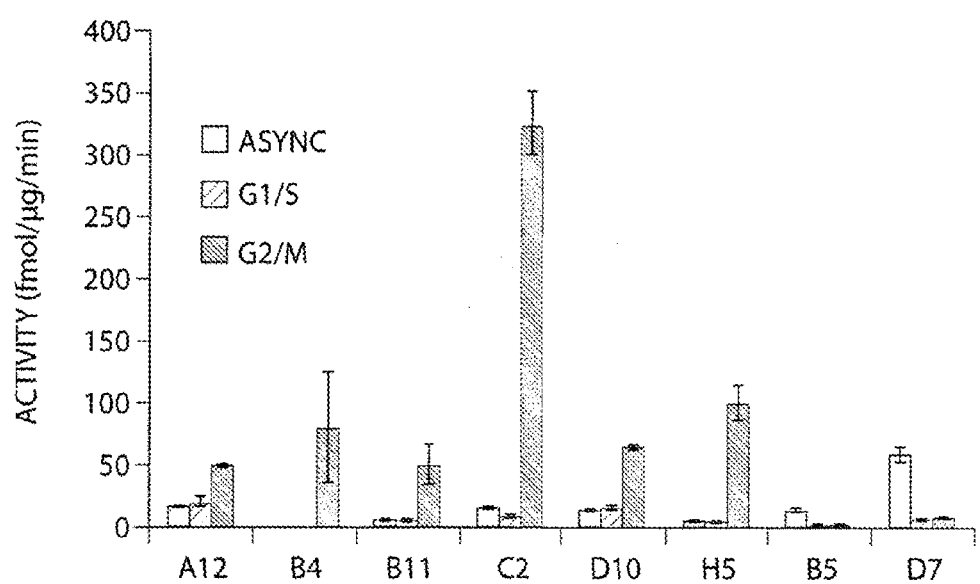

FIG. 4D is a bar graph showing data for these peptides that were observed to have altered phosphorylation activities in the cell lysates from cells treated as in FIGS. 4B and 4C.

FIGS. 5A-5D are a set of heat maps, a bar graph, and photographs of immunoblots showing peptide phosphorylation rates as reporters for pathway activation state.

Figure 5A:
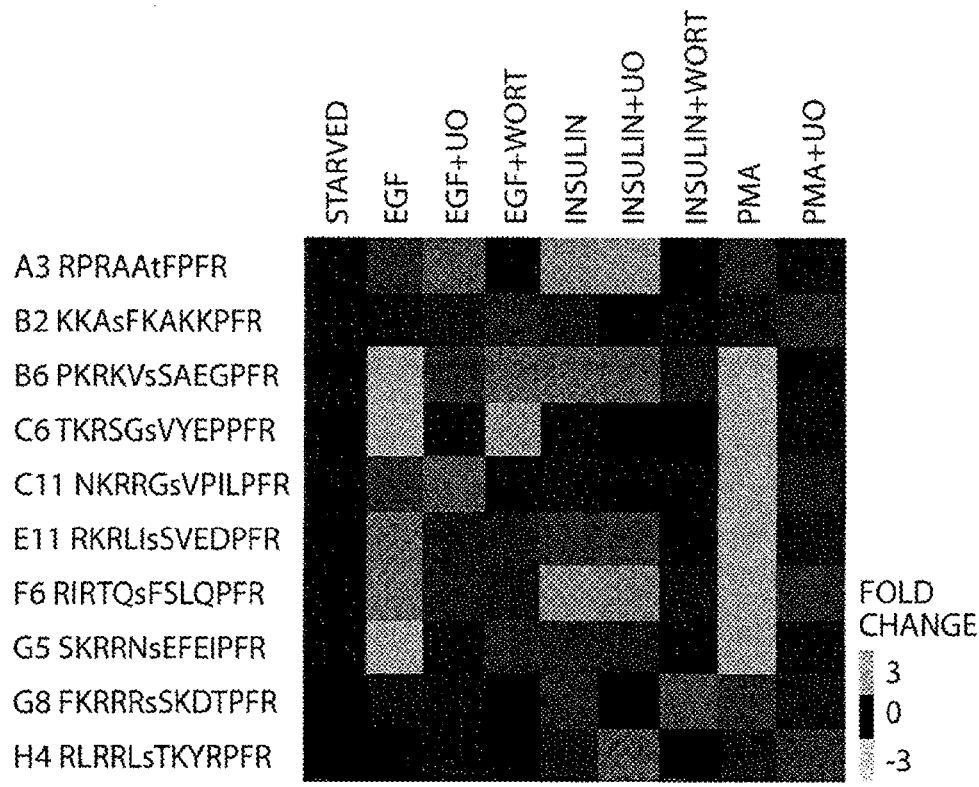

FIG. 5A is a heat map showing examples of peptide (from top as in the figure: SEQ ID NOs: 1, 12, 16, 28, 33.57. 64, 75. 78, 86, respectively) phosphorylation activities by different cell lysates. Activities (average of duplicate analyses) are shown as the fold increase (decrease) normalized to the starved HEK293 cell state. Phosphorylated SIT are represented by lower case letters.

Figure 5B:
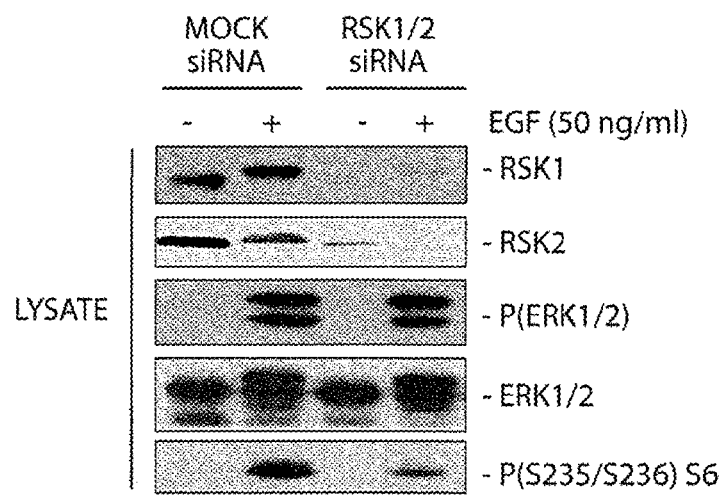

FIG. 5B is a photograph of an immunoblot analysis that depicts siRNA-mediated knockdown of RSK1/2 and activation pattern of the MAPK downstream targets ERK, RSK and S6.

Figure 5C:
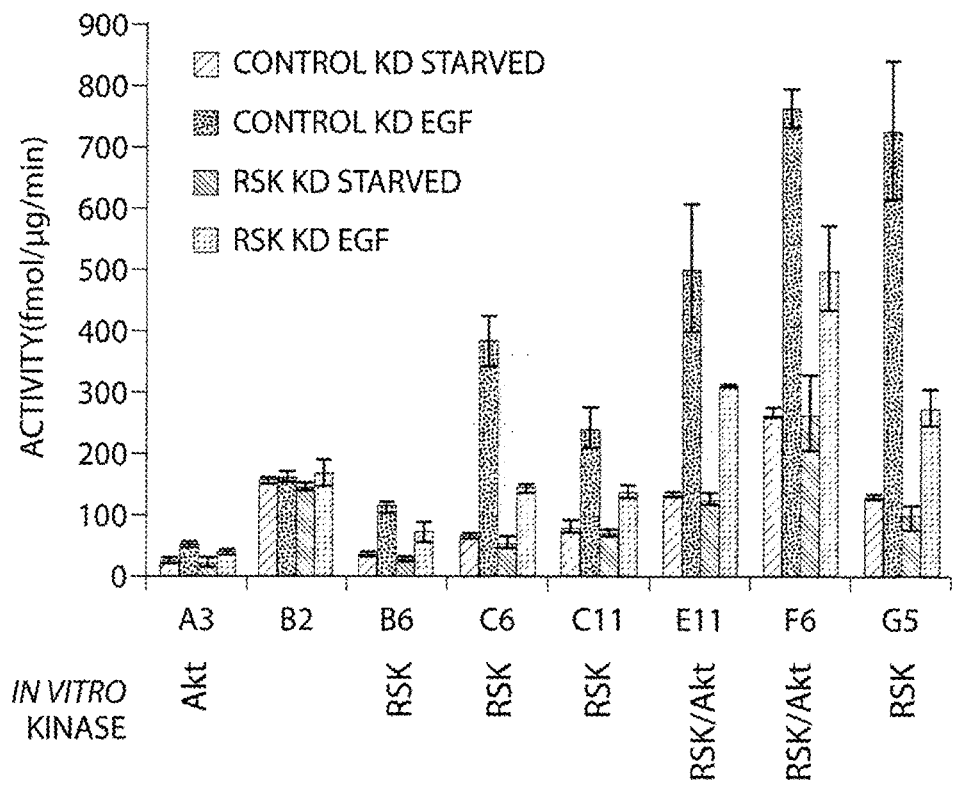

FIG. 5C is a bar graph showing selected KAYAK peptide phosphorylation rates using the lysates analyzed in FIG. 5B.

Figure 5D:
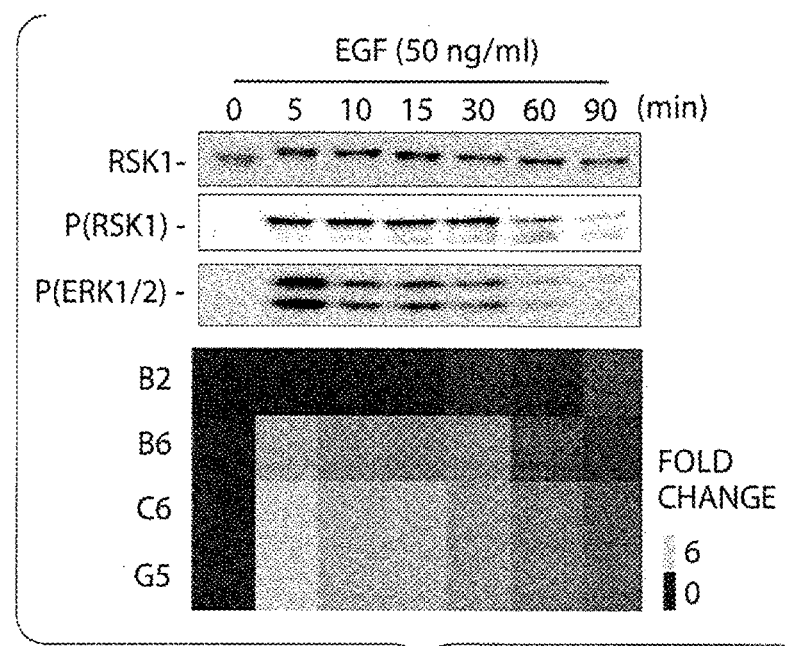

FIG. 5D shows MAP kinase pathway status as a function of time during EGF stimulation. Both immunoblot and selected KAYAK activities are shown. Activities were normalized to the serum-starved state (time 0). Peptide B2 (KKAsFKAKKPFR, SEQ ID NO: 12, derived from C. elegans putative serine/threonine-protein kinase C05D10.2, Ser-351) is included as an unchanging control.

Figure 6A:
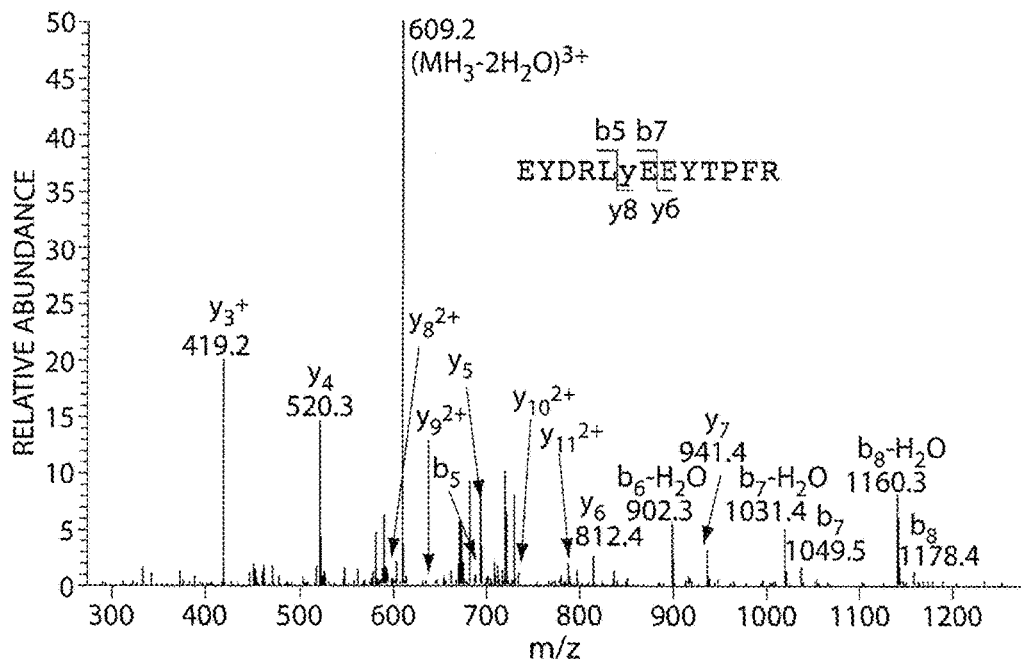
Figure 6B:
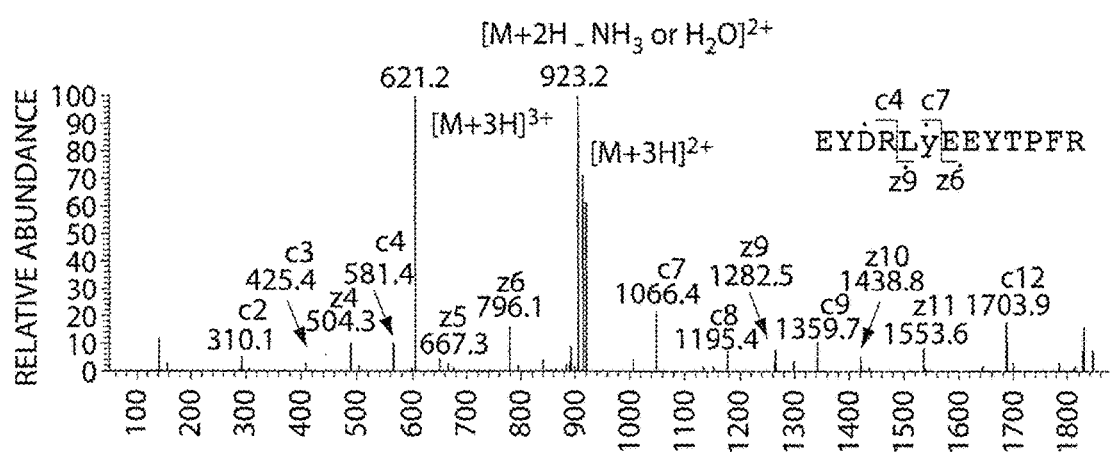

FIGS. 6A and 6B are a set of MS data showing phosphate localization within the H5peptide.

FIG. 6A shows H5peptide (SEQ ID NO: 87) that was phosphorylated by a nocodazole arrested HeLa cell lysate and the resulting phosphor-H5 was subjected to MS/MS analysis. The correct sequence was determined with an Ascore (Beausoleil et al. 2006Nat Biotech 24:1285-1292) of 19.2.

FIG. 6B is an ETD spectrum of the phospho-H5 peptide. Diagnostic ions for the designated sequence (EYDRLY*EEYTPFR; SEQ ID NO: 87) are highlighted by a gray box.

FIGS. 7A-7F are a bar graph, a set of photographs of immunoblots, and a line graph showing identification and validation of Sic kinase activity with respect to Tyr-199 of PI 3-kinase regulatory subunit p55.

Figure 7A:
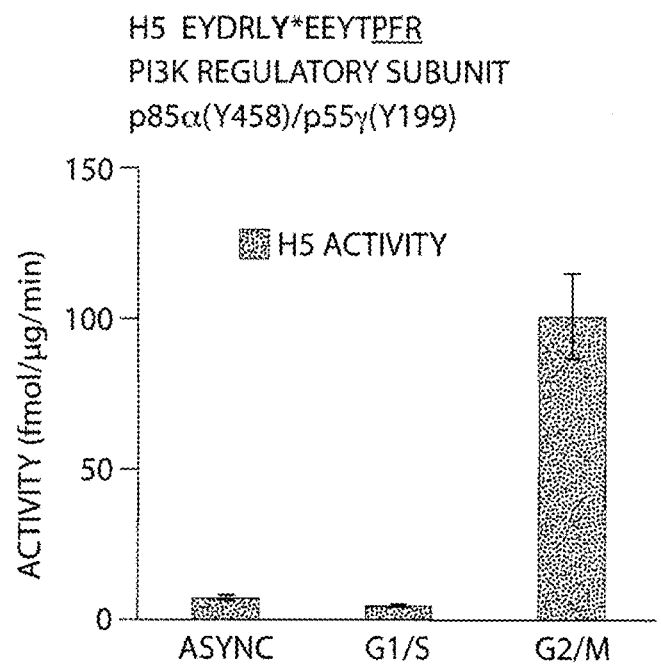

FIG. 7A is a bar graph showing that activity was observed with respect to substrate peptide H5 (SEQ ID NO: 87) in lysates of asynchronously growing HeLa cells and cells arrested in G1/S and G2/M phase.

Figure 7B:
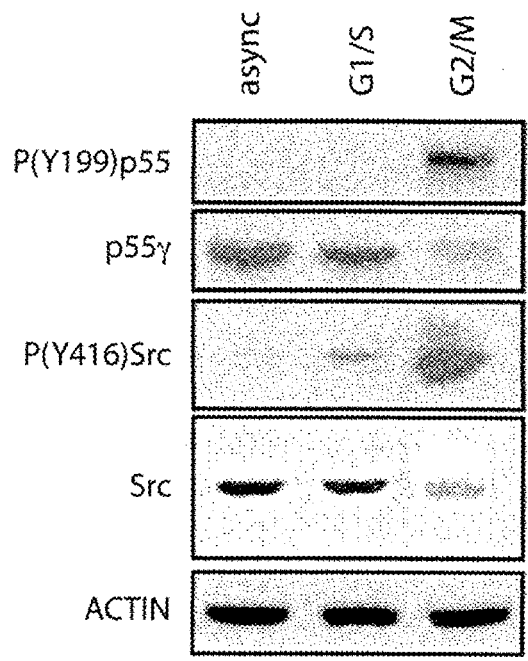

FIG. 7B is a photograph showing immunoblotting data obtained for each of the phospho-PI3K regulatory subunit p55 (Tyr-199) and other proteins in the same lysates.

Figure 7C:
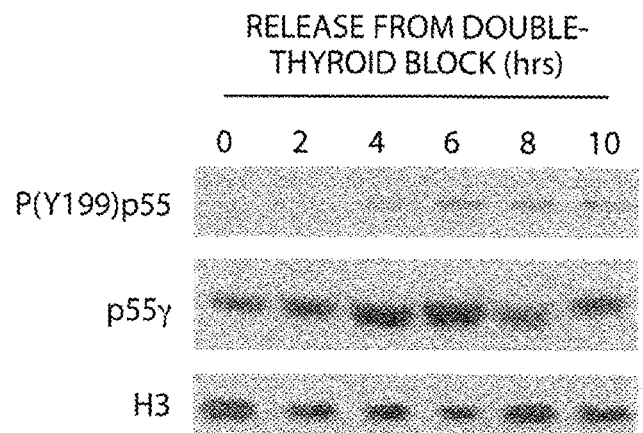

FIG. 7C is a photograph showing immunoblotting data obtained for each of phospho-PI3K regulatory subunit p55 (Tyr-199) and phospho-retinoblastoma protein (Ser-780) immunoreactivity in HeLa cells released from double-thymidine block.

Figure 7D:
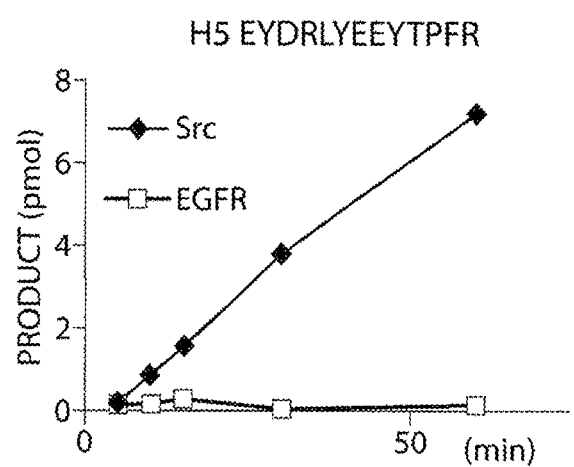

FIG. 7D is a line graph showing in vitro phosphorylation of peptide H5 (SEQ ID NO: 87) using each of purified Src and EGFR.

Figure 7E:
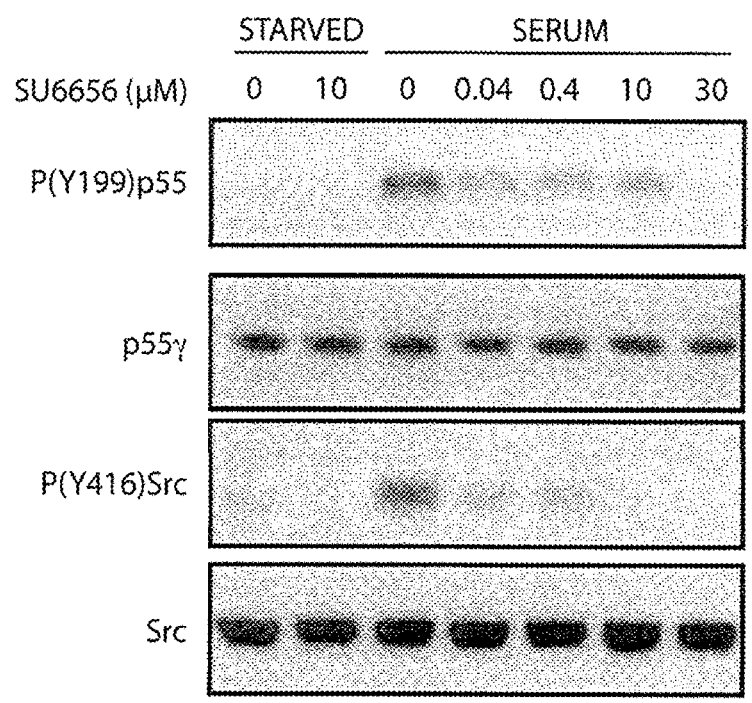

FIG. 7E is a photograph of immunoblot data of lysates following treatment of asynchronously growing HEK293 cells with Sic family kinase (SFK) specific inhibitor SU6656 in starved or serum-fed cells.

Figure 7F:
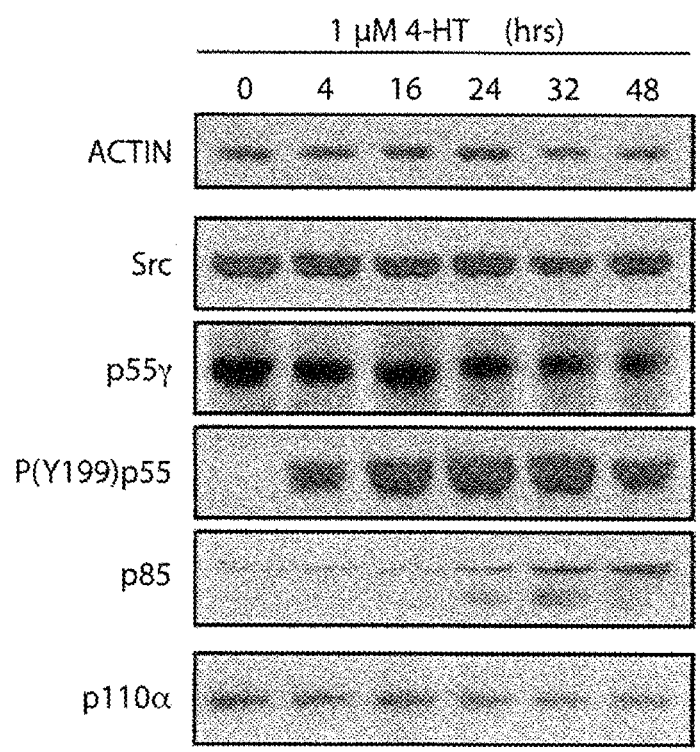

FIG. 7F is a photograph showing immunoblotting analysis of vSrc-ER expressing MCF10A cells treated with 4-HT as a function of time to activate Sic.

Figure 8:
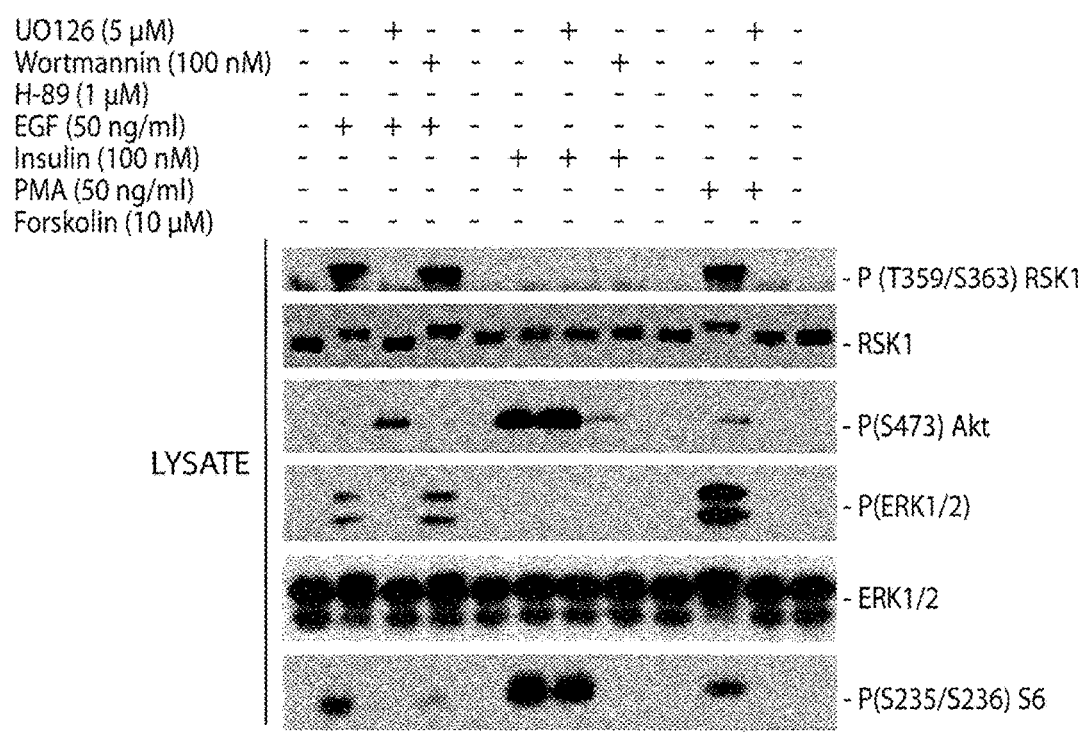

FIG. 8 is a photograph of an immunoblot analysis of the cell lysates used in FIG. 3A, and a table showing treatment of cells in lysate samples in each lane.

Figures 9A, 9B:
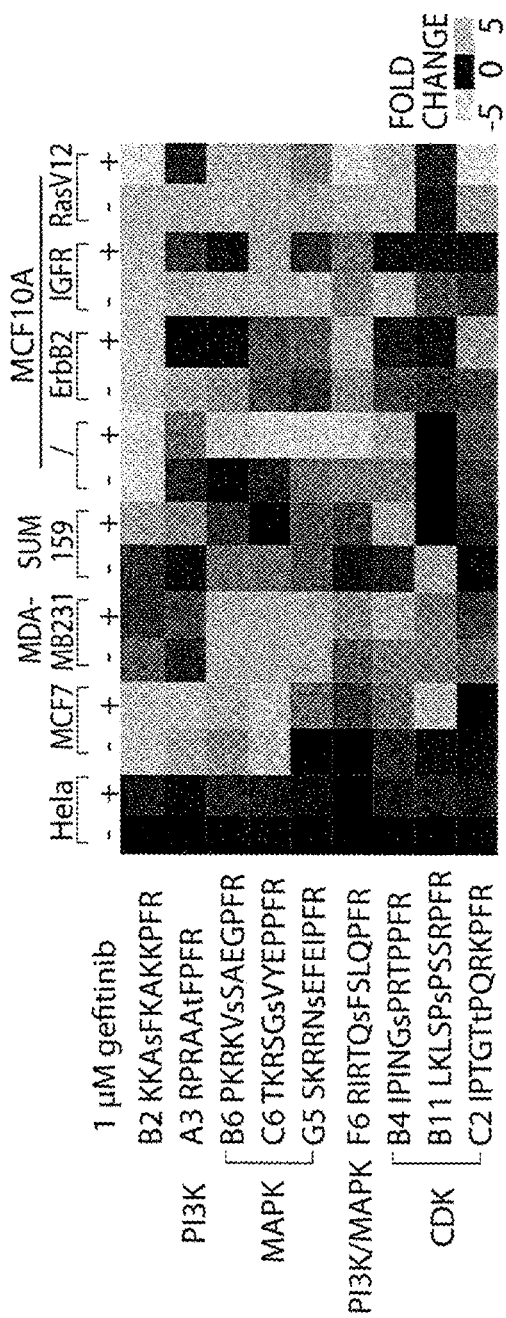
Figure 9C:
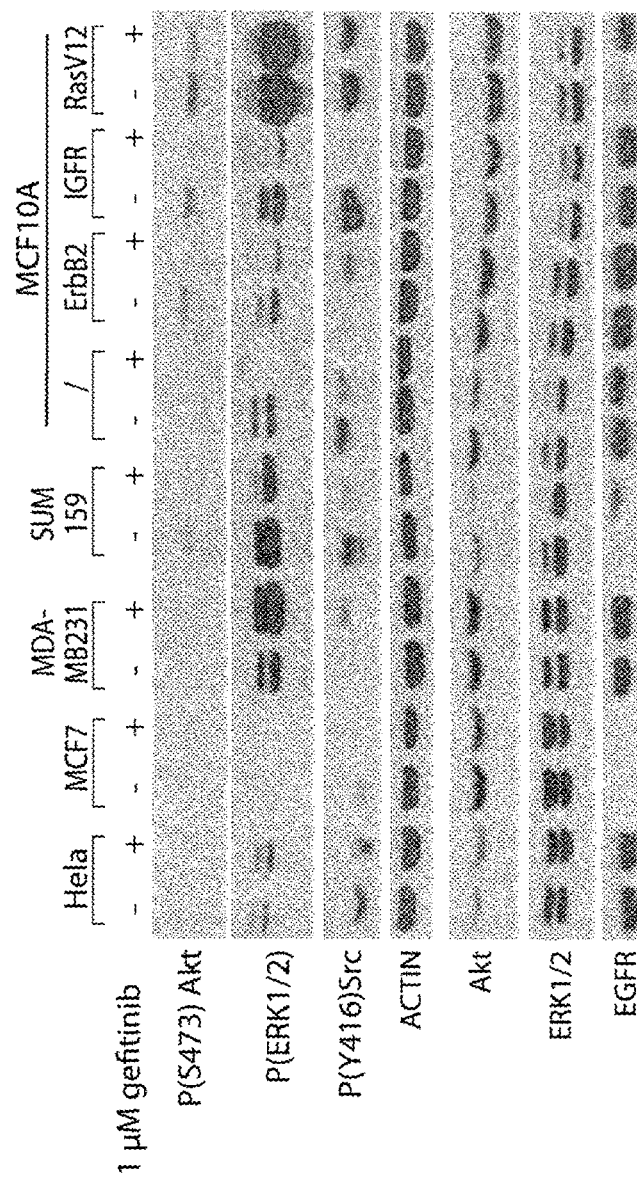

FIGS. 9A-9C are a table, a heat map, and a photograph of immunoblots showing kinase activity profiling in cancer cell lines.

FIG. 9A is a table showing activating mutations (residue number and amino acid substitution) of protein components the PI3K and MAPK pathways.

FIG. 9B is a heat map profiling specific kinase pathway activities in cancer cell lines using KAYAK. Eight different cell lines received either no treatment or were treated with 1 µM of specific EGFR inhibitor, gefitinib (Iressa) for 24 hrs, Peptide (from top: SEQ ID NOs: 12, 1, 16, 28, 75, 64 14, 21, 24, respectively) phosphorylation rates (average of duplicates) were acquired through the KAYAK assay, and were normalized to asynchronously growing HeLa cell values and plotted as a fold-difference heat map.

FIG. 9C is a photograph of Western blotting analysis of the lysates for cancer cell lines used in FIG. 9B.

Figure 10A:
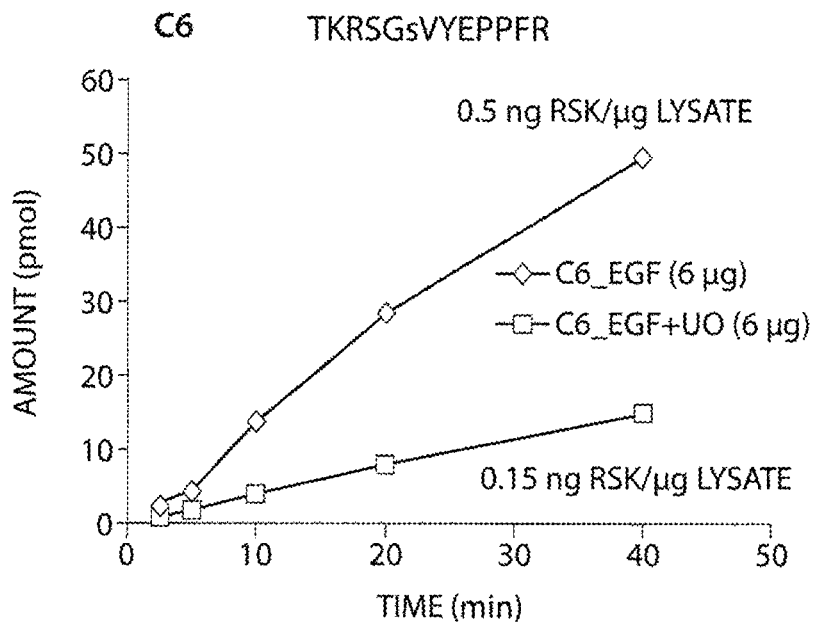

FIGS. 10A and 10 B are a set of line graphs showing phosphorylation of C6 peptide (SEQ ID NO: 18) by cell lysates and activated kinases.

FIG. 10A shows-that peptide C6 (SEQ ID NO: 28) was phosphorylated by lysates of EGF stimulated HEK293 cells (6 µg); lysates were prepared from HEK293 cells pretreated with MEK inhibitor U0126 and stimulated with EGF, or EGF alone. Reactions conditions were the same as shown in Examples herein.

Figure 10B:
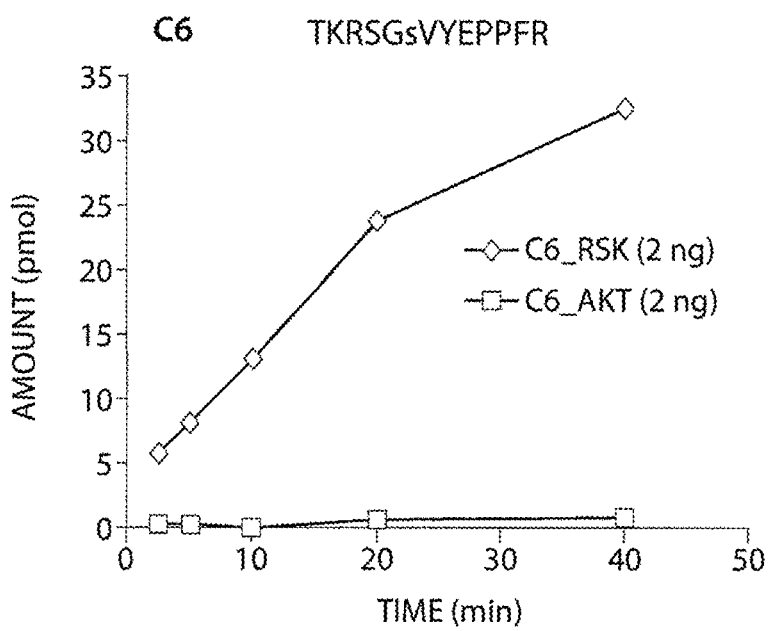

FIG. 10B shows that peptide C6 (SEQ ID NO: 28) was phosphorylated in vitro using 2 ng of activated, purified Akt or RSK. Reaction mixture was supplemented with 0.1% BSA. Other conditions were the same as in FIG. 10A.

Figure 11A:
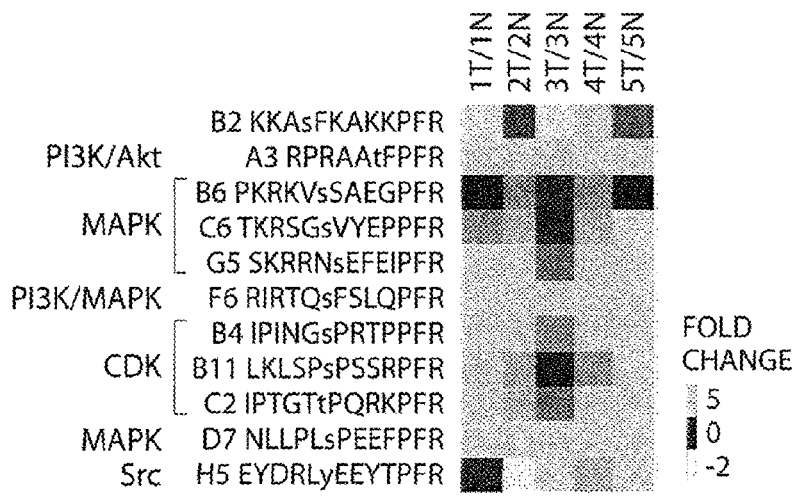
Figure 11B:
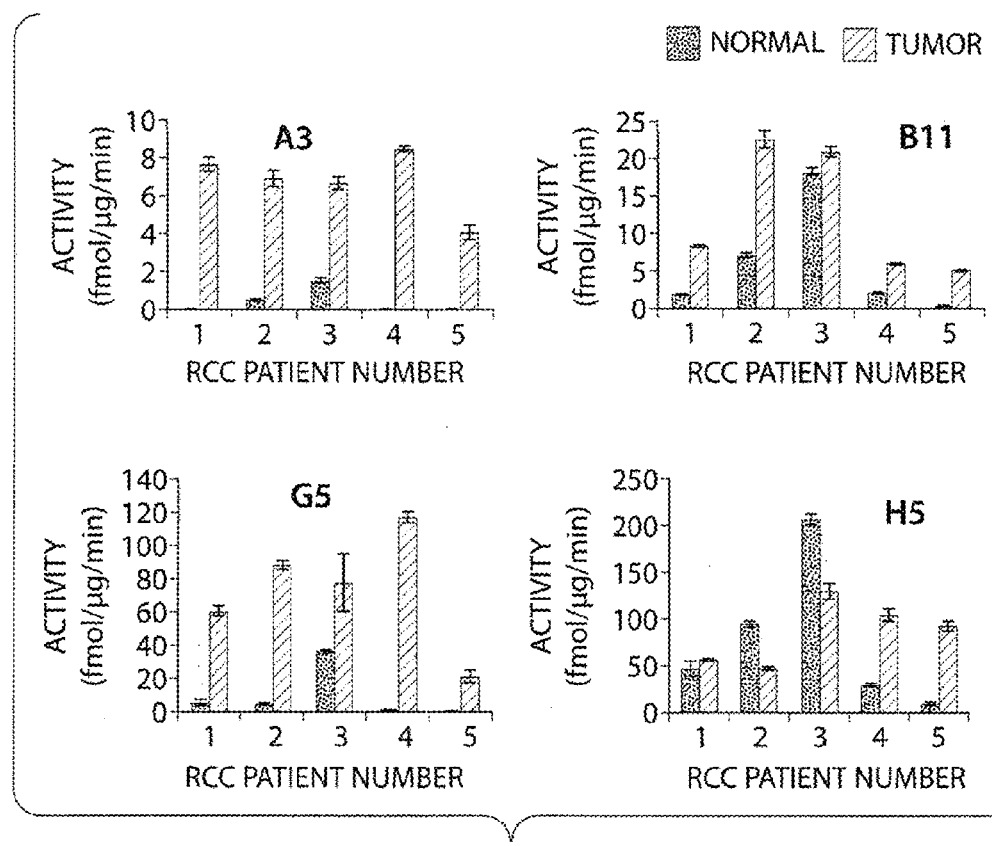
Figure 11C:
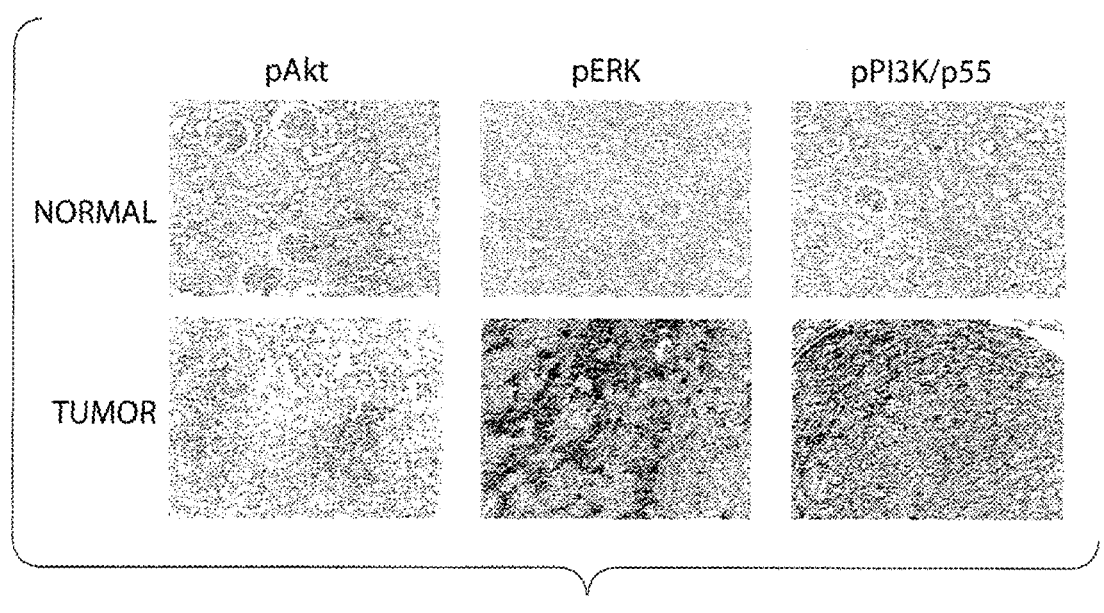

FIGS. 11A-11C are a heat map, a set of bar graphs, and a set of photomicrographs showing kinase activity profiling in renal cell carcinoma tissues.

FIG. 11A is a heat map showing KAYAK profiling of normal and cancerous tissues from five renal cell carcinoma patients (patient numbers are shown at the top of the heat map). The activities in cancerous (T, tumor) tissue were normalized to normal (N) tissue values from the same patient, assayed with petptides (from to SEQ ID NOs: 12, 1, 16. 28, 75, 64, 21, 24, 41, 87, respectively).

FIG. 11B is a set of bar graphs showing representative results for several peptides including Akt-selective peptide A3 (PI3K/Akt: SEQ ID NO: 1), CDK-selective peptide B11 (CDK; SEQ ID NO: 21), RSK-selective peptide G5 (MAPK/RSK; SEQ ID NO: 75) and Src-selective peptide H5 (Src: SEQ ID NO: 87). In each set of two adjacent bars, tumor tissue values are illustrated in the bar on the right, and normal tissue in the bar on the left. In general, higher activities were observed in tumor tissues than in normal FIG. 11C is a set of photographs showing three different immunohistochemical analyses of each normal and cancerous tissue samples from patient number 3.

FIGS. 12A-12D are a set of amino acid sequences, photographs of immunoblots, and a ribbon model showing regulation of phosphorylation of p55 at Tyr-199.

FIG. 12A shows sequence alignment of the regulatory subunit of PI3K. Sequences corresponding to peptide H5 (SEQ ID NO:, 87) is underlined with the phosphorylated Tyr indicated by a lighter shading. The sequences of the regulatory subunits of various species, such as human, bovine, mouse and rat (SEQ ID NOs: 93 and 94), show high homology. Exception is clawed toad (*Xenopus laevis*; abbreviated XENLA; SEQ ID,NO: 95) which does not show high homology for this sequence.

FIG. 12B is a photograph of a Western blot of HEK293 cells that were starved and were then stimulated with insulin, IGF and EGF. Phospho-p55 (Tyr-199) levels were monitored using Western blotting analysis.

FIG. 12C is a photograph of a Western blot showing that phospho-p55 (Tyr-199) in MCF10A cells did not change as a result of 4-HT treatment, MCF 10A cells expressing ER:vSrc and MCF10A cells were treated with 1 µM 4-HT for the indicated time.

FIG. 12D is a ribbon model showing Tyr-467/p85α (correspondent of Tyr-199/p55γ) is 2.7 Ångstroms distance from His-450p110α in the crystal structure of PI-3kinase, close to potential hydrogen-bond formation (Huang et al. 2007 *Science* 318: 1744-1748).

Figure 13:
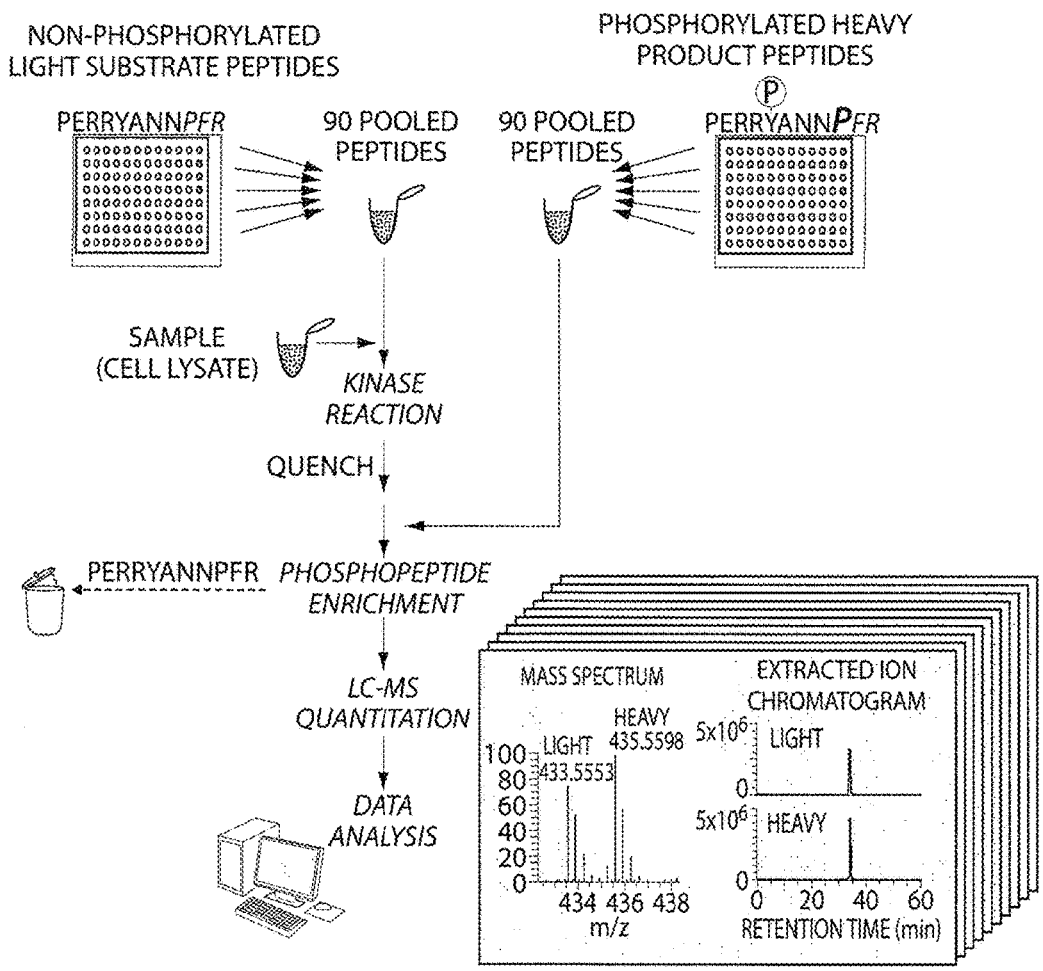

FIG. 13 is a set of drawings, photographs and an MS printout showing workflow for a single-reaction, 90-substrate in vitro kinase assay. Synthetic substrate peptides are pooled and incubated with cell lysate. After kinase reactions are quenched, stable isotope-labeled phosphopeptides (internal standards; heavy label on italicized proline) of identical sequence to substrate peptides are added at a known concentration. Phosphorylated substrate peptides and internal standard phosphopeptides are enriched using immobilized metal-ion affinity chromatography and are analyzed by LC-MS techniques. Pairs of light (product) and heavy (internal standard) peptides perfectly co-elute, yet differ in mass by 6 Da, and are quantified by direct ratio of light-to-heavy areas under the curve from high resolution data. Each assay produces 90 activity measurements of activities within core signaling pathways.

Figure 14A:
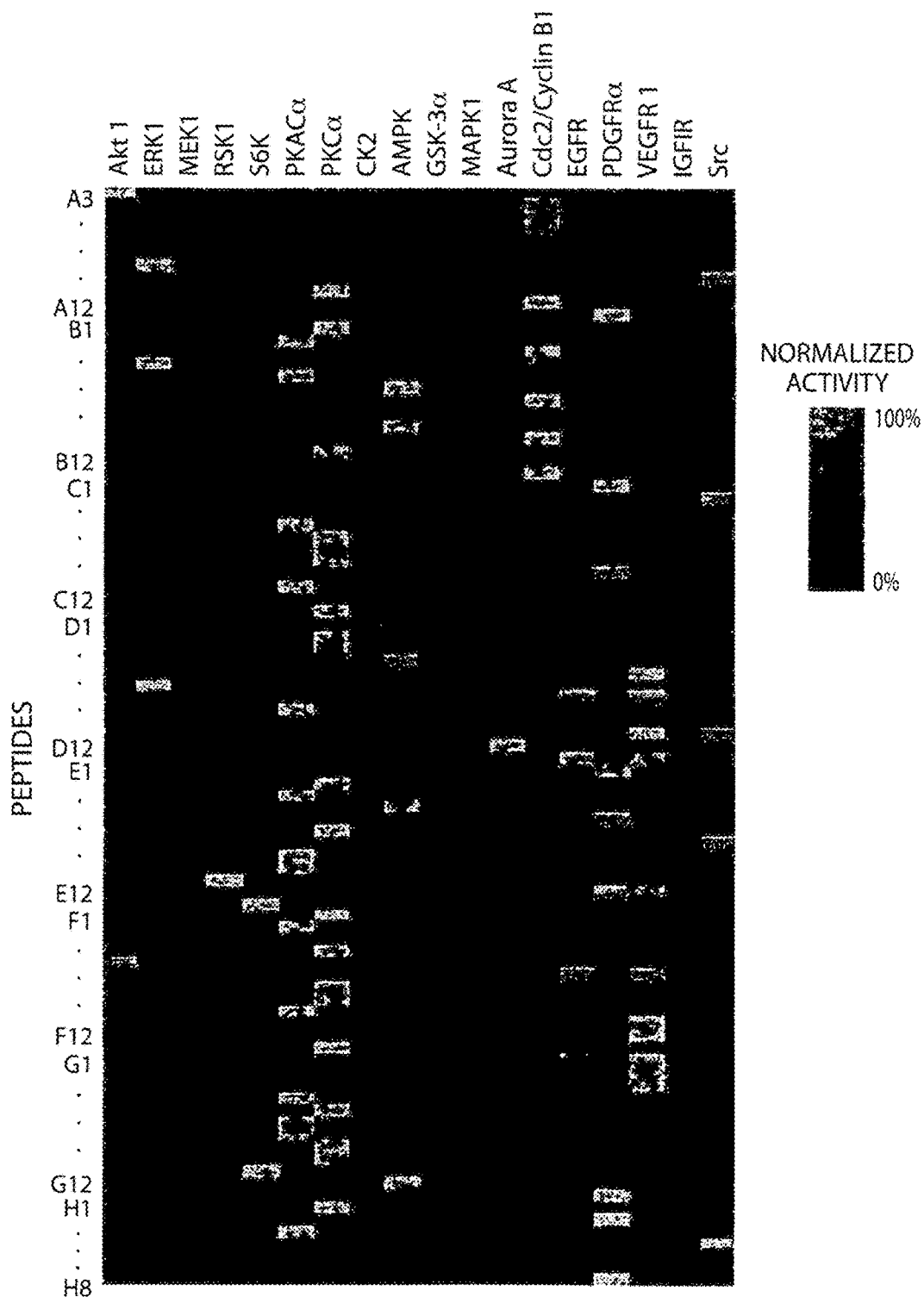
Figure 14B:
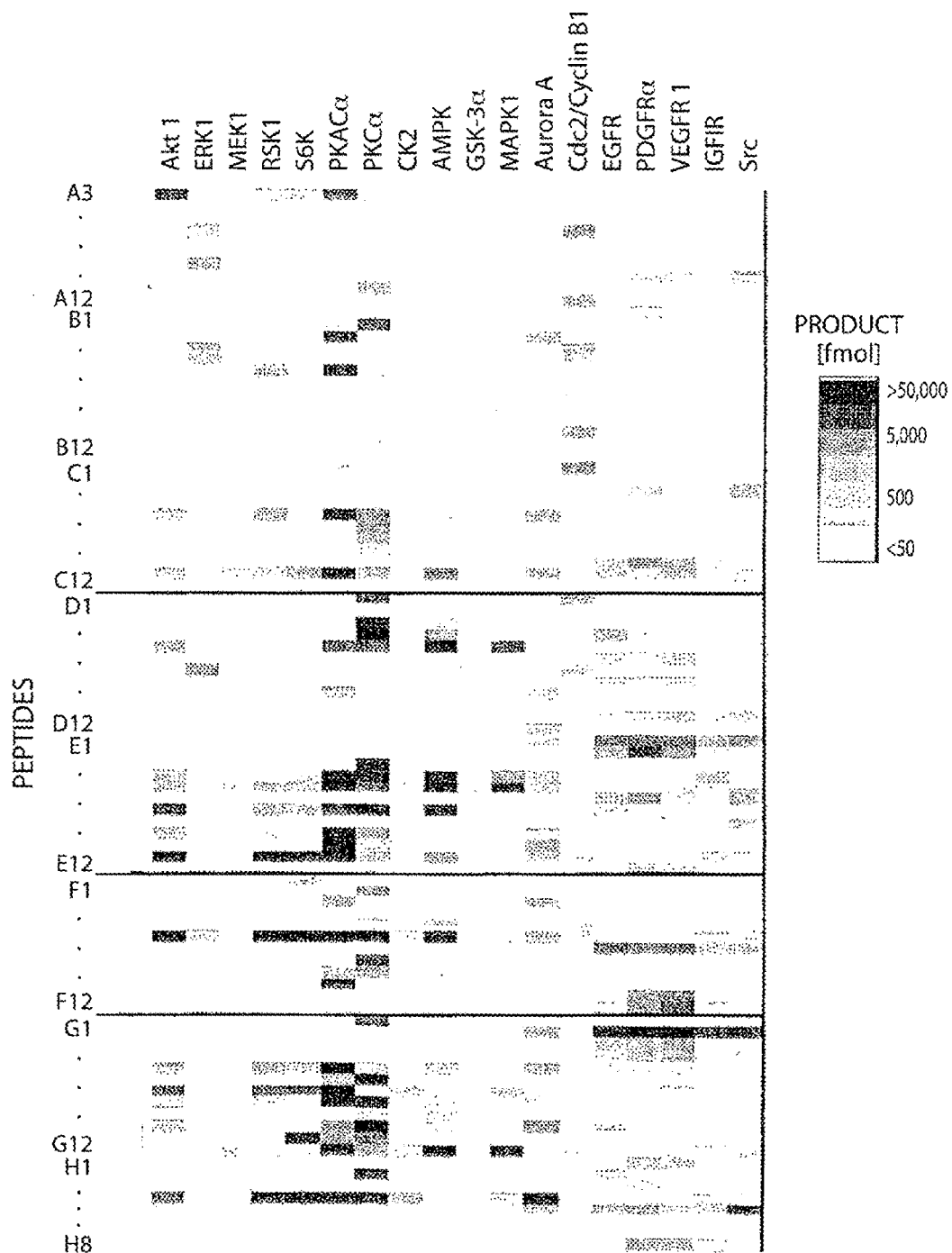

FIGS. 14A and 14B are a set of heat maps showing purified kinases assayed using 90 peptide substrates. Commercially available active kinases (50 ng) were analyzed by KAYAK profiling using the 90 peptides.

FIG. 14A shows phosphorylation rates normalized to the highest activity to show the specificity of the peptides.

FIG. 14B shows absolute amounts of products using an exponential color code (shown here as grading of gray).

Figure 15A:
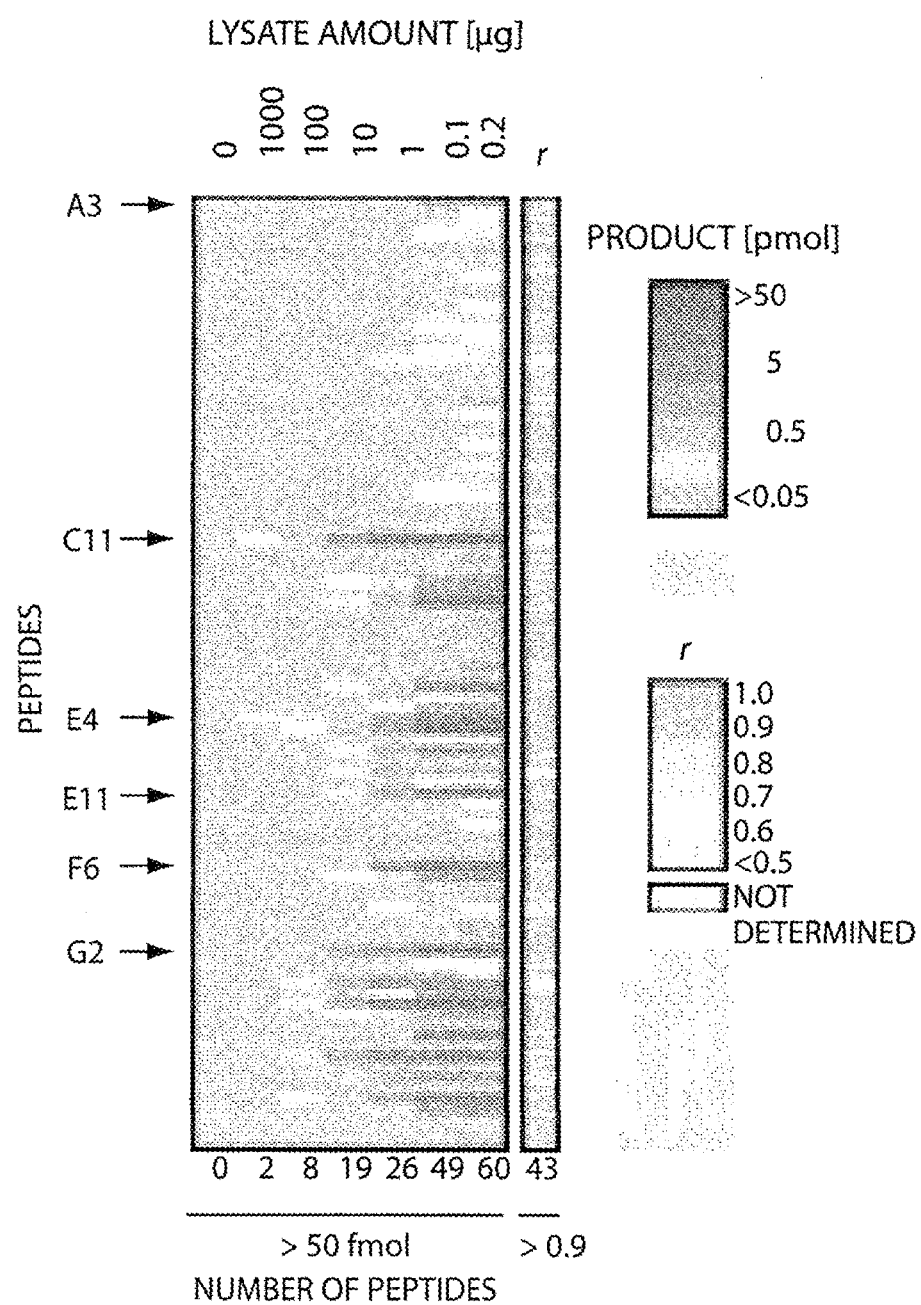
Figure 15B:
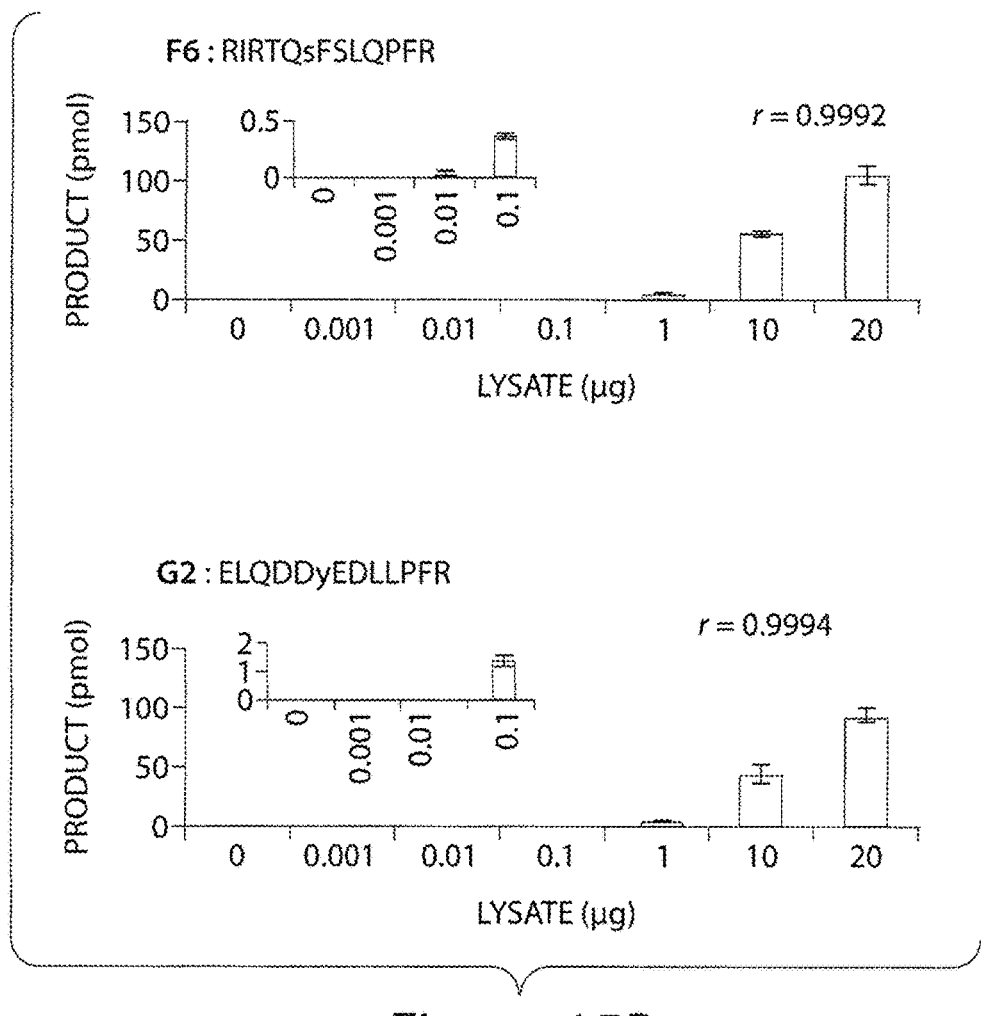
Figure 15C:
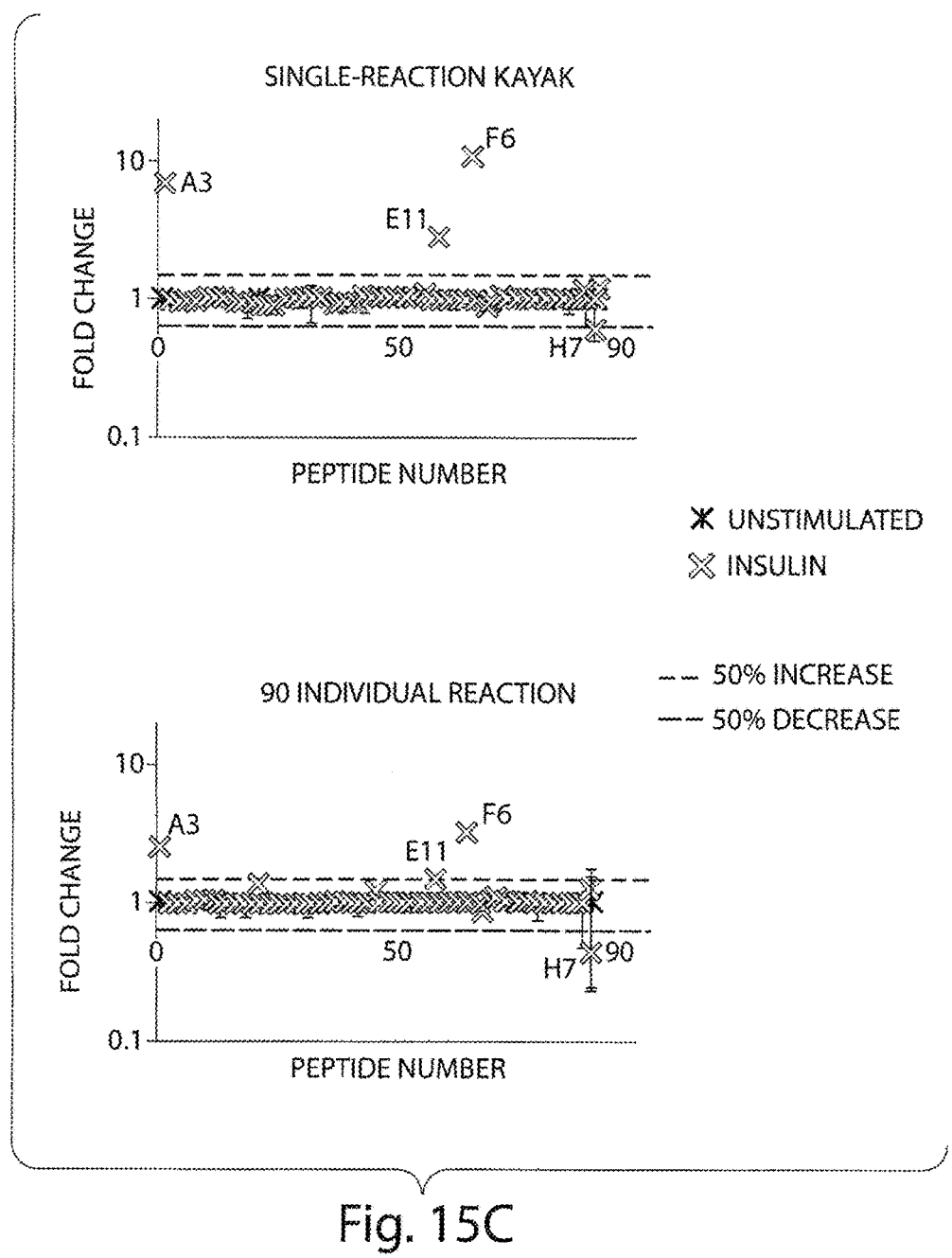

FIGS. 15A-15C are a heat map, a set of bar graphs and a set of fold-change plots showing sensitivity and reproducibility of the assay.

FIG. 15A is a heat map showing sensitivity and linearity of the 90-peptide KAYAK approach. Seven different amounts of lysate from HEK293 cells treated with insulin were used. Product amounts are shown as heat map of white to dark gray. Products of less than 50 fmol were empirically considered not observed (light gray). The Pearson product-moment correlation coefficients for lysate-to-product amounts for each peptide are shown as a separate right-side panel using gray intensity scaling.

FIG. 15B is a set of bar graphs showing activities obtained as a function of amount of lysate for exemplary peptides from FIG. 15A including a Ser-phosphorylated peptide (F6, SEQ ID NO: 64) and a Tyr-phosphorylated peptide (G2, SEQ ID NO: 72). The data are shown as means of duplicates with error bars to the minimum and maximum values.

FIG. 15C is a set of fold-change plots showing comparison between single-reaction (competing peptides) and 90 individual kinase assay (no competition). The fold change for each peptide's activity measurement for HEK293 cells with (X) and without insulin (vertically marked X) treatment is shown. Each reaction consumed 20 µg of lysate. Product amounts were normalized to untreated cell lysate and are displayed as means ±s.d. (n=3).

Figure 16A:
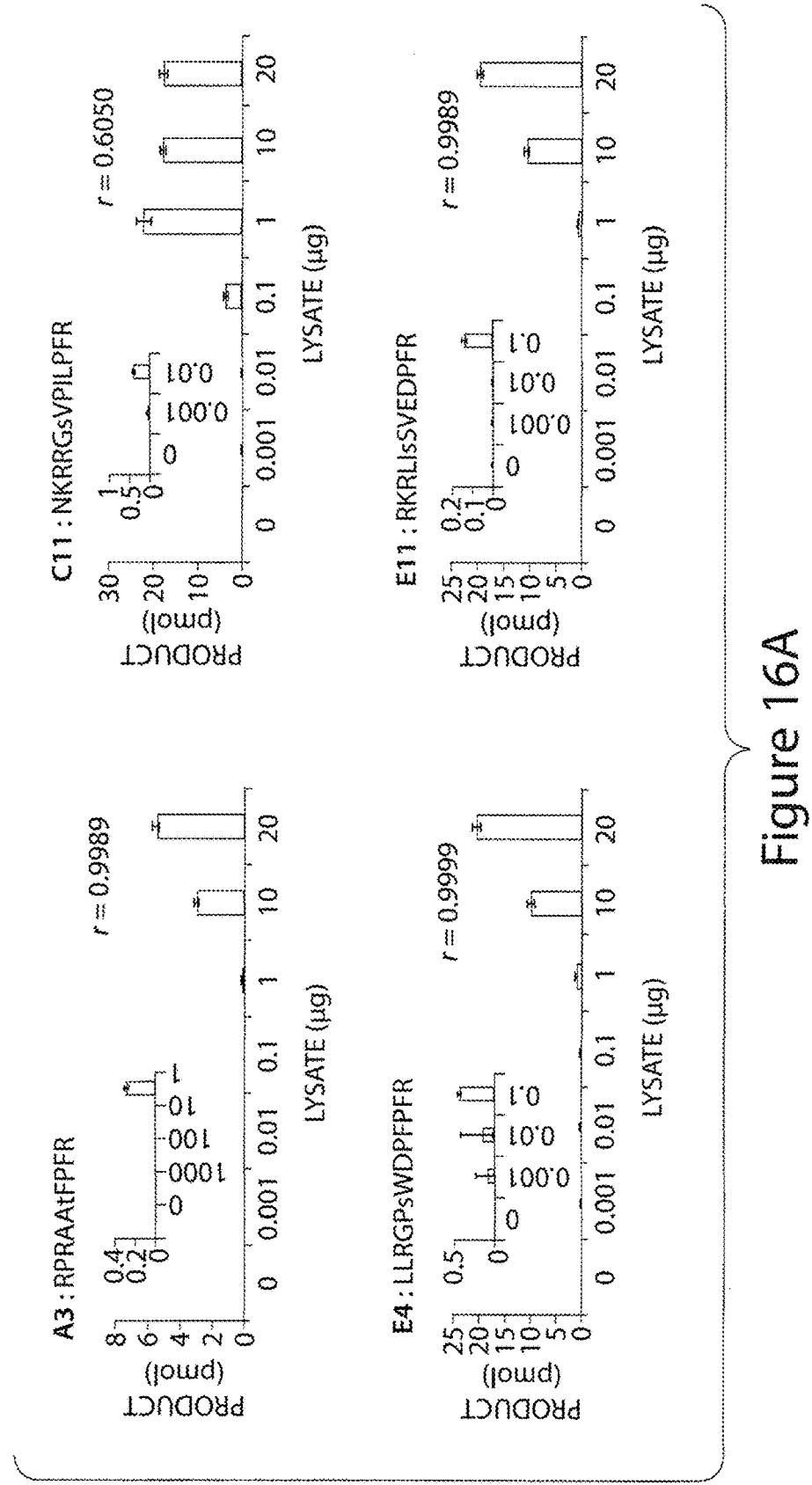
Figure 16B:
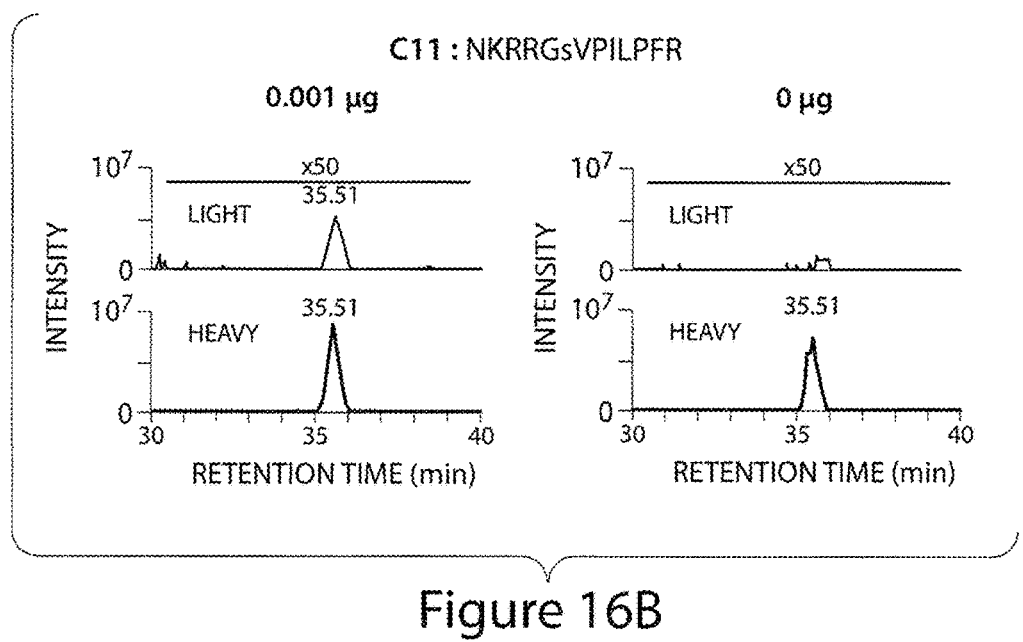

FIGS. 16A and 16B are a set of bar graphs and line graphs showing sensitivity of the KYAK assay (based on data in FIG. 15A).

FIG. 16A is a set of bar graphs showing additional substrate peptide (A3, SEQ ID NO: 1; C11, SEQ ID NO: 33: E4, SEQ ID NO: 50; E11, SEQ ID NO: 57) examples including one of only 3 peptides with an r value <0.7 (C11) based on data in FIG. 15A. The data are shown as means of duplicates with error bars to the minimum and maximum values.

FIG. 16B is a set of line graphs showing extracted ion chromatograms for the 1 ng and blank lysate amounts of peptide C11 (SEQ ID NO: 33). Mass chromatograms for light (m/z =540.6353) and heavy (m/z =542.6399) KAYAK phosphopeptides were extracted at a tolerance of 10 ppm. Phosphorylation was still quantifiable at the 1 ng lysate level using a 45 min reaction time.

Figure 17A:
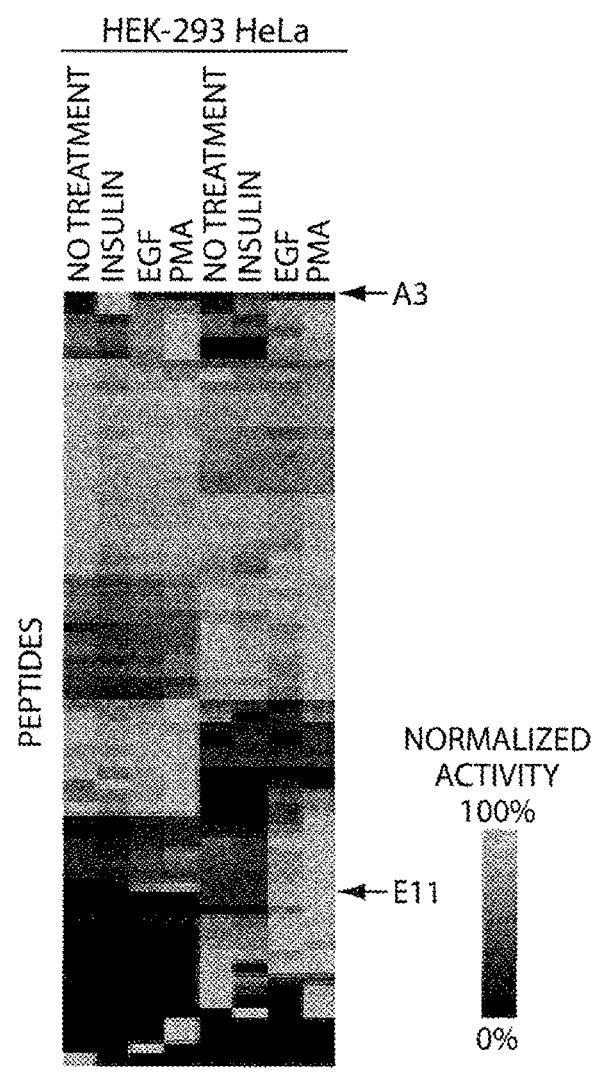
Figure 17B:
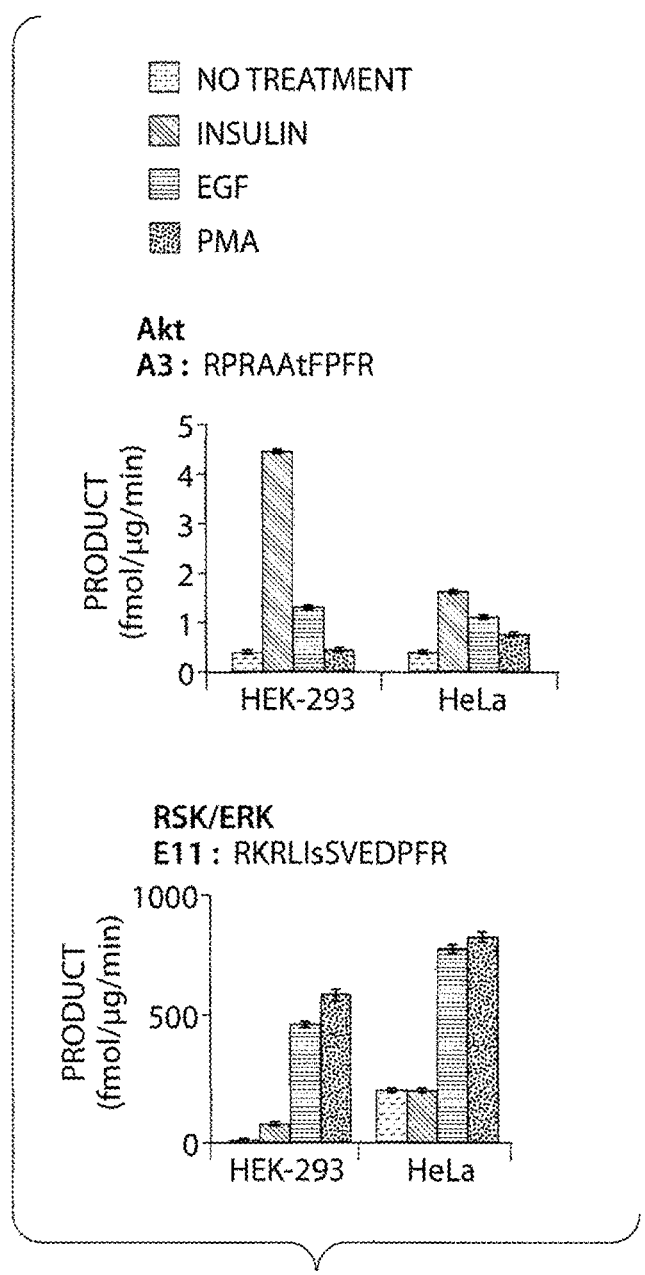
Figure 17C:
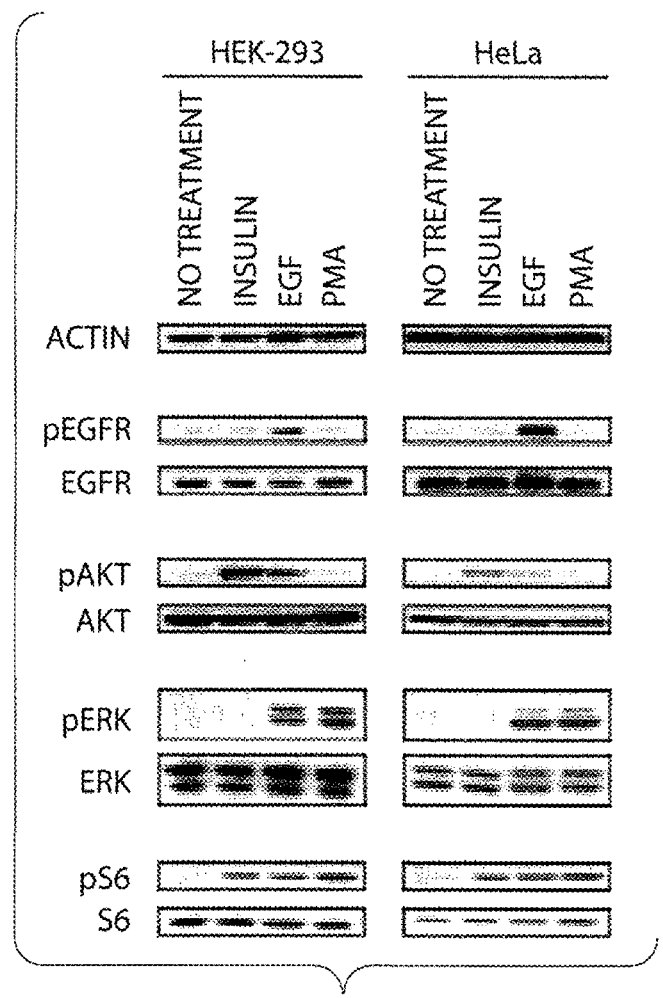

FIGS. 17A-17C are a heat map, a set of bar graphs and a set of photographs of immunoblots showing, induced core pathway phosphorylation changes in human cell lines faithfully reported by KAYAK profiling.

FIG. 17A is a heat map of triplicate KAYAK activity data. Kinase activities using lysates (20 μg) from HEK293 cells and HeLa cells untreated or treated with insulin, EGF or PMA were measured utilizing 90 peptides. The phosphorylation rates for the 68 observed peptides were normalized by that of the highest phosphorylated sample and analyzed by Pearson coefficient hierarchical clustering, which groups similar responders together. Each row represents the phosphorylation rate of a different peptide normalized to the highest value in the row.

FIG. 17B is a set of bar graphs showing examples of peptides (A3, SEQ ID NO: 1; and E11, SEQ ID NO: 57) in 17A. The data are shown as average ±s.d. (n=3). Candidate kinases are listed based on phosphorylation using purified kinases shown in FIGS. 14A and 14B.

FIG. 17C is a set of photographs showing Western blotting analysis of the lysates using antibodies as indicated.

Figure 18:
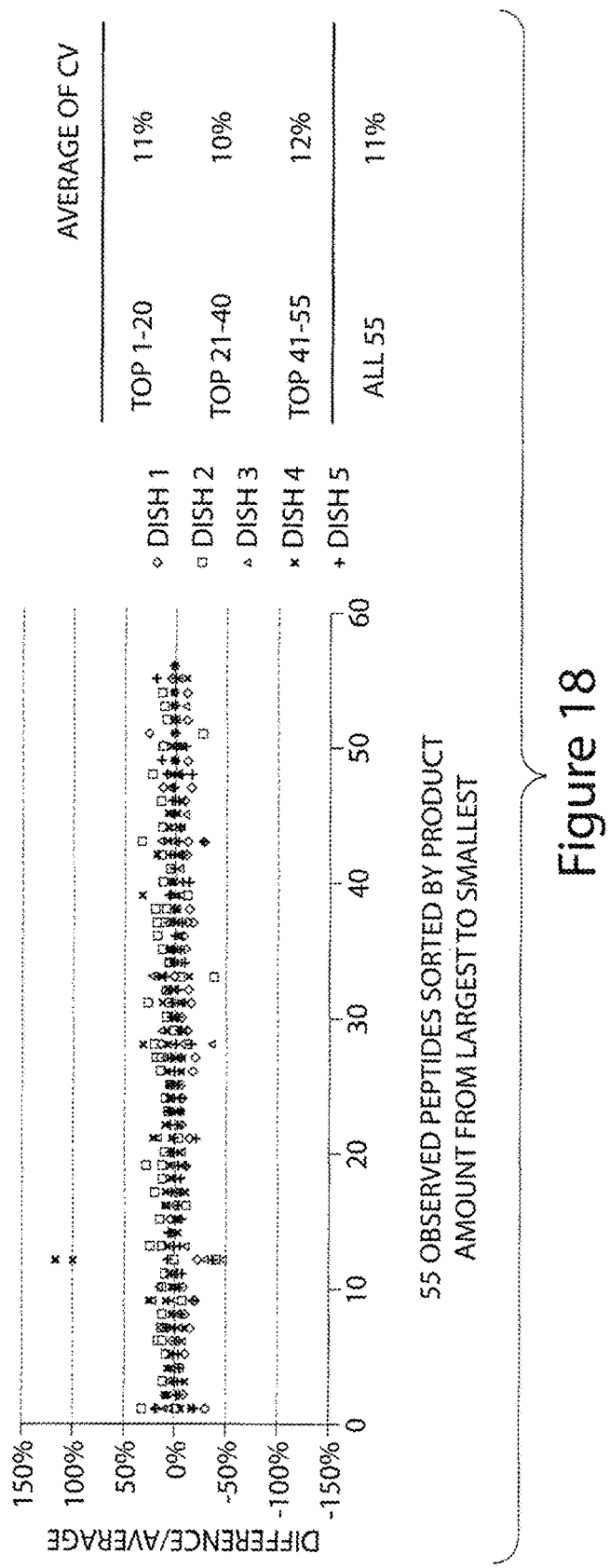

FIG. 18 is a fold-change plot and a table showing reproducibility of the KAYAK measurements. HEK293 cells were cultured in five separate dishes, independently lysed, and 20 μg of the lysate were subjected to duplicate KAYAK analyses utilizing all 90 peptides. Using all 10 measurements (duplicates x 5 dishes), 55 peptides were observed. Ordering each peptide by product amount resulted in average coefficients of variation of less than 12% regardless of product amount.

Figure 19A:
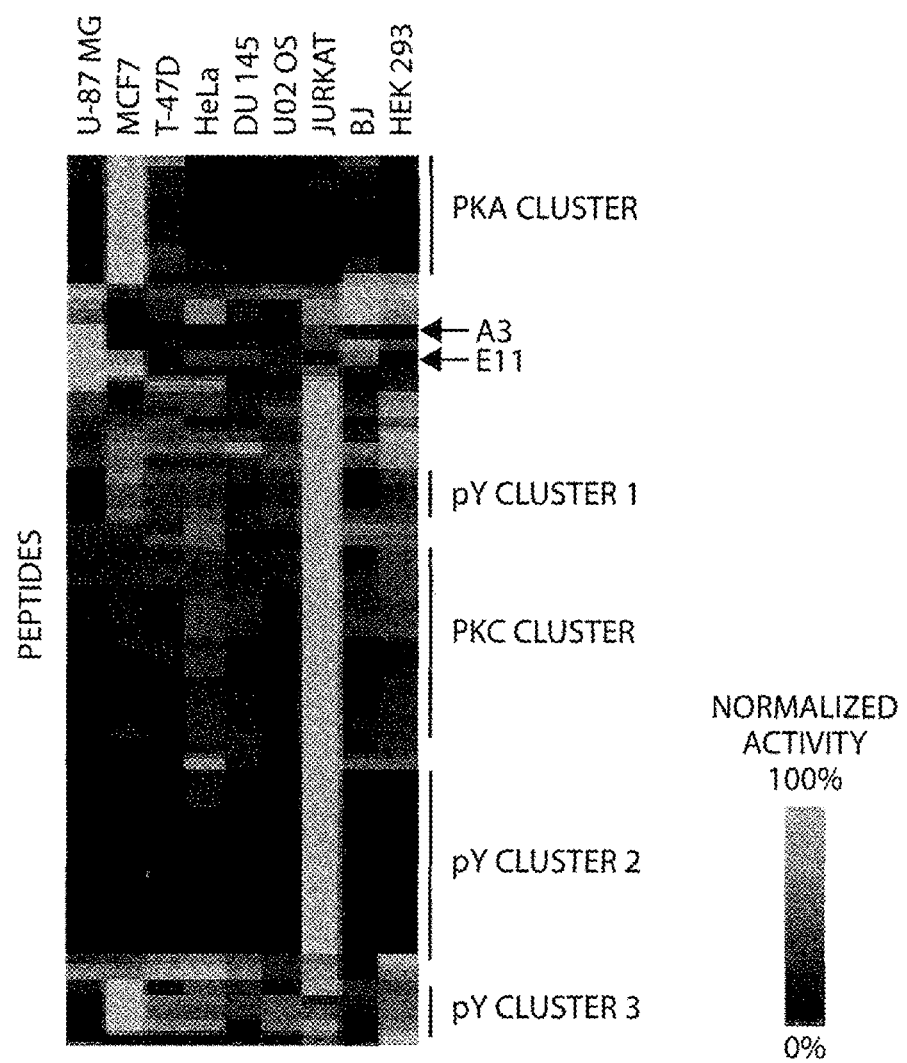
Figure 19B:
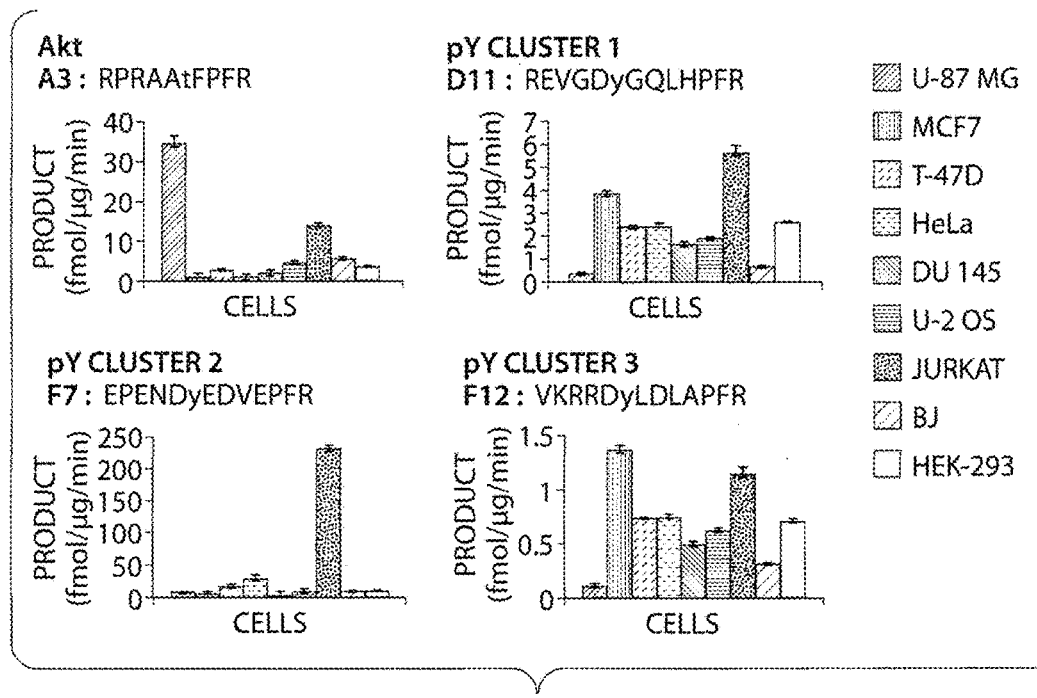
Figure 19C:
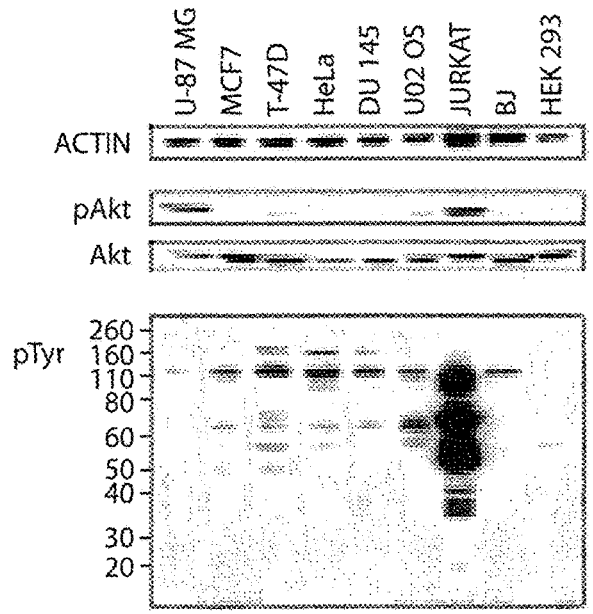

FIGS. 19A-19C are a heat map, a set of bar graphs and a set of photographs of immunoblots showing KAYAK profiling of nine human cell lines that demonstrates heterogeneity in basal kinase activities and core pathway activation state.

FIG. 19A is a heat map of kinase activities. The nine cell lines included U-87 MG (glioblastoma), MCF7 (breast), T-47D (breast), HeLa (cervical), DU 145 (prostate), U-2 OS (osteosarcoma), Jurkat (T lymphocyte), BJ (foreskin fibroblast) and HEK293 (embryonic kidney). Each was cultured under ATCC recommended conditions and lysed. Lysates (20 μg) were subjected to KAYAK profiling. Using 68 peptides with observable pbosphorylation, activities were normalized to the highest value in each row, followed by hierarchical cluster analysis which groups peptides with similar responses together.

FIG. 19B is a set of bar graphs showing examples of several peptides (A3, SEQ ID NO: 1: D11, SEQ ID NO: 45; F7, SEQ ID NO: 65; F12, SEQ ID NO: 70) from FIG. 19A. The data are shown as the mean from duplicate analyses with minimum and maximum values as error bars.

FIG. 19C is a set of photographs showing Western blotting analysis of the lysates using antibodies as indicated.

Figure 20:
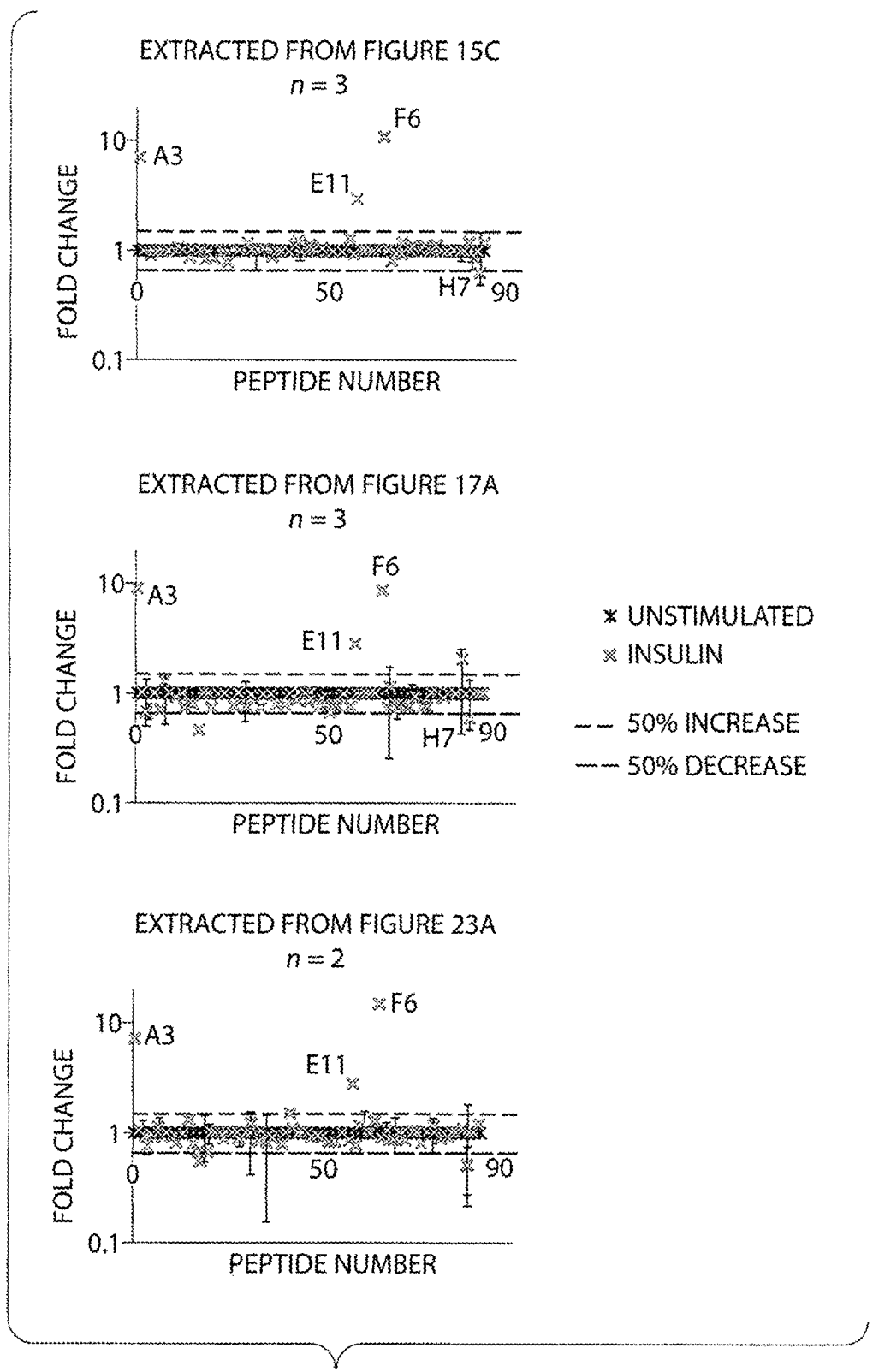
Figure 23A:
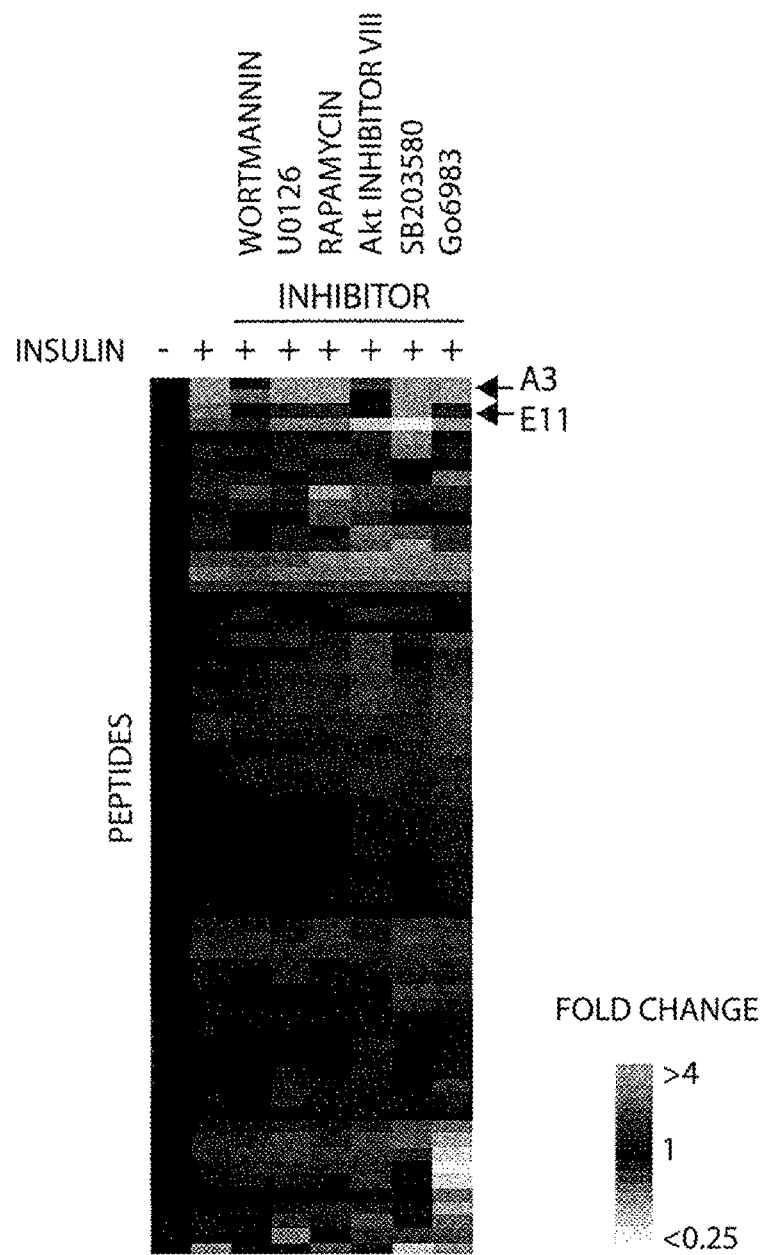
Figure 23B:
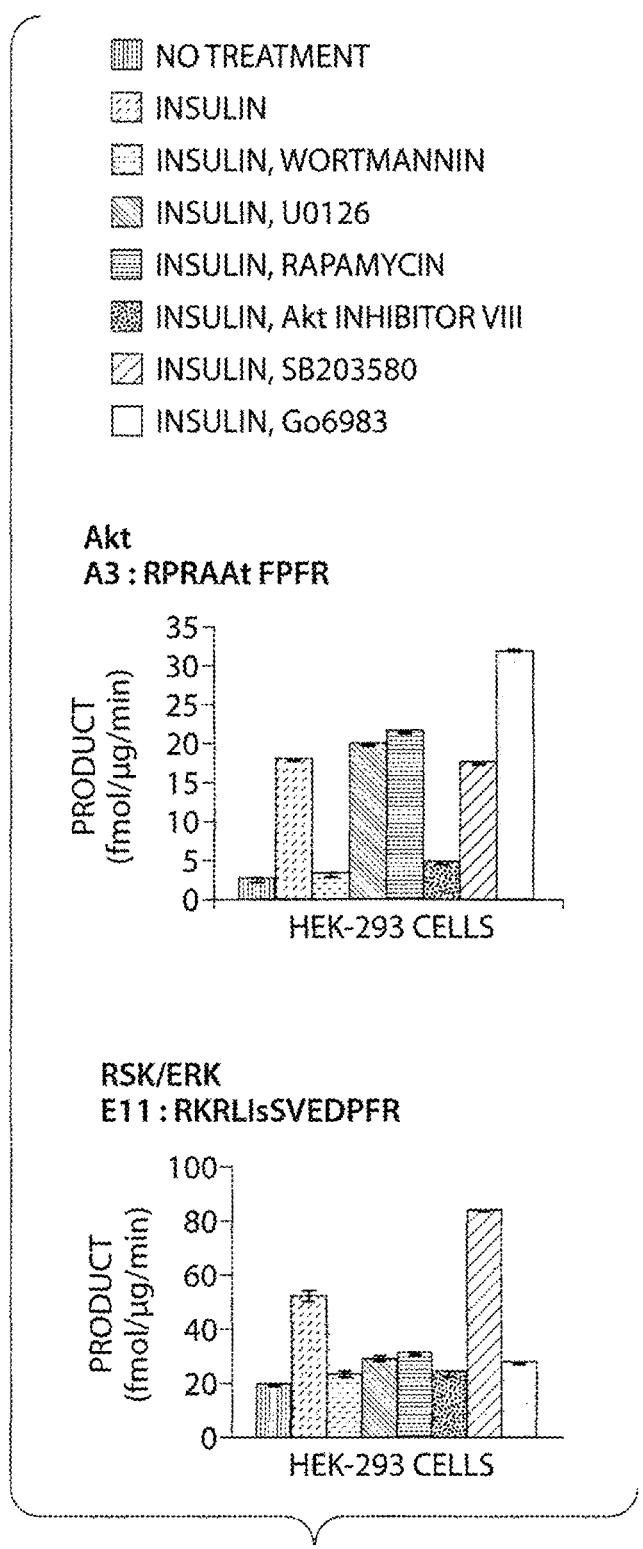
Figure 23C:
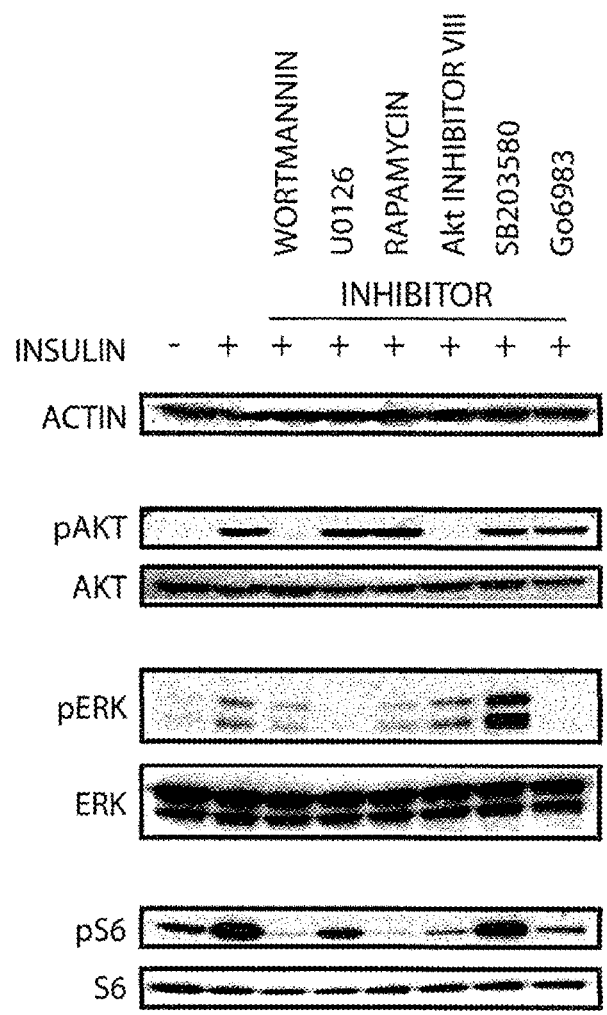

FIG. 20 is a set of fold-change plots showing reproducibility of fold-change measurements in HEK293 cells with (X) or without (vertically marked X) insulin stimulation in three examples. Each example included separate culture on different days, insulin stimulation, protein isolation, and duplicate KAYAK profiling. Only three peptides were consistently upregulated in their phosphorylation rates (A3, F6 and E11), Peptides A3 and F6 derived from known substrates of PI3K/Akt. The parent protein for peptide E11 is reported to be a RSK substrate. Full spectrum insulin-dependent phosphorylation pathways for each peptide are shown in FIGS. 23A-23C. Based on stimulating with insulin in the presence of various pathways inhibitors, peptide E11 is highly specific for the MAP kinase pathways (RSK), and its phosphorylation is increased in an insulin, Akt, and MAP kinase-dependent fashion in HEK293 cells.

Figure 21A:
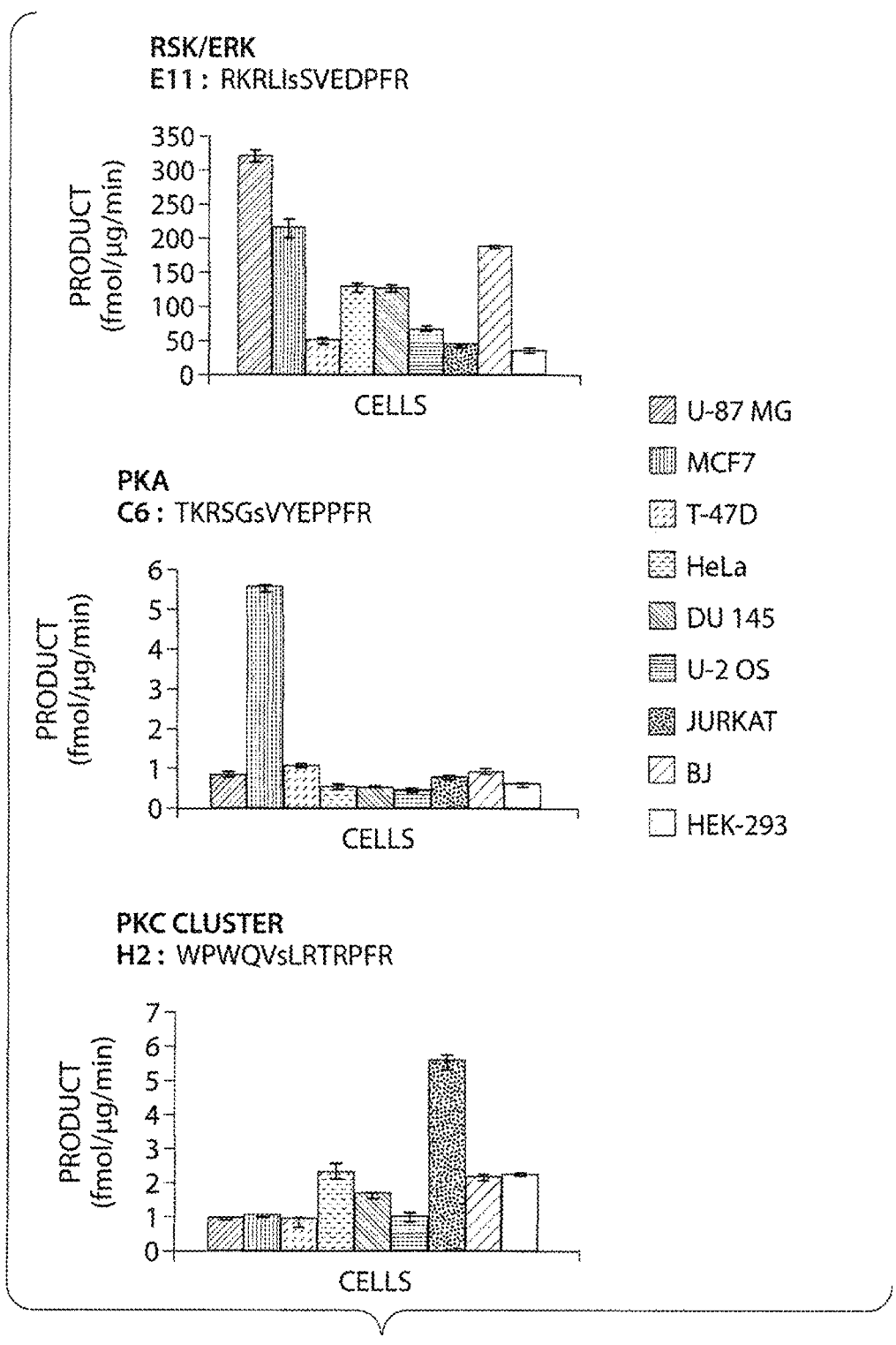
Figure 21B:
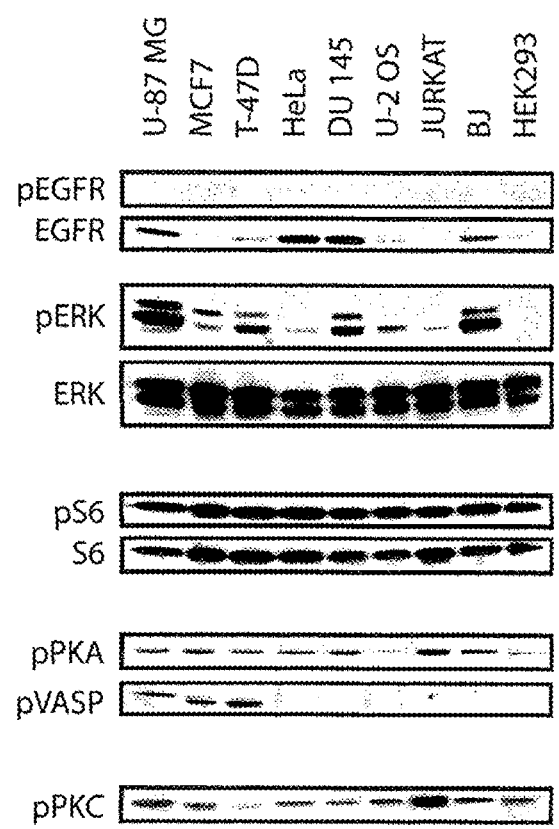

FIGS. 21A and 21B are a set of bar graphs and a set of photographs of immunoblots showing additional KAYAK peptides (based on data for cell lines in FIGS. 19A-19C).

FIG. 21A is a set of bar graphs showing core pathway activation differences in additional KAYAK peptide, profiles (from top: SEQ NOs: 57, 28, 84), The data are shown as the mean from duplicate analyses with minimum and maximum values as error bars. Potential kinases are assigned based on phosphorylation with purified kinases shown in FIGS. 14A and 14B.

FIG. 21B is a set of photographs showing Western blotting of the lysates using the indicated antibodies.

FIGS. 22A-22F are a heat map, a set of bar graphs, a UV-chromatogram, a set of line graphs and a fold-change plot showing identification of Cdc2/Cyclin B1 complex as an activated kinase in mitosis.

Figure 22A:
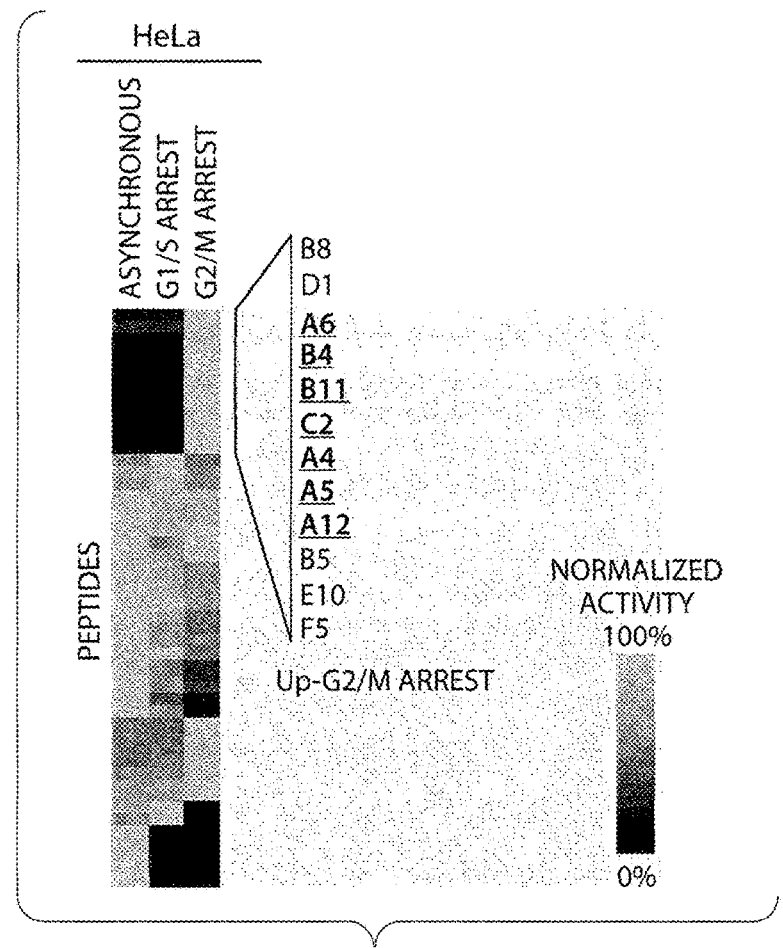

FIG. 22A is a heat map of kinase activities from cell cycle lysates. HeLa cells were cultured under standard conditions (asynchronous), or synchronized in either G1/S or G2/M phase of the cell cycle. Kinase activities using lysate (20 μg) were analyzed by KAYAK profiling. Phosphorylation rates were normalized and clustered as in FIGS. 17A-17C.

Figure 22B:
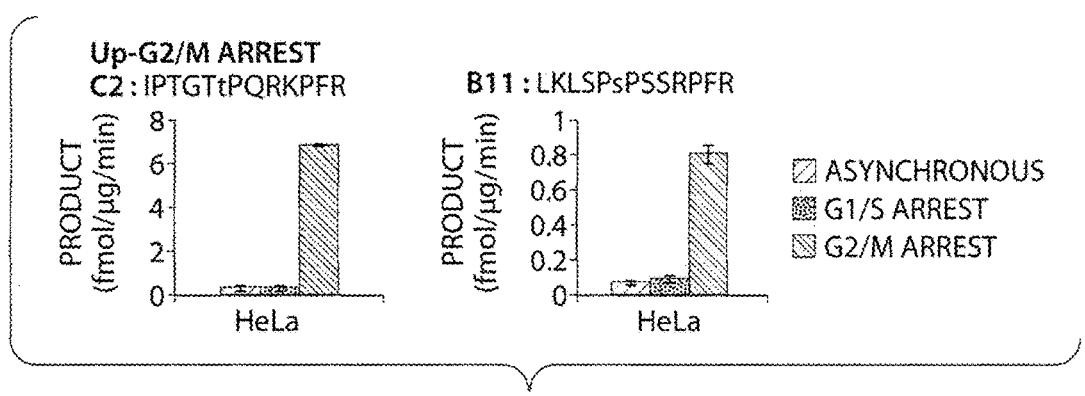

FIG. 22B is a set of bar graphs showing exemplary peptides C2 (SEQ ID NO: 24) and B11 (SEQ ID NO: 21) chosen for correlation profiling to identify the mitotic kinase.

Figure 22C:
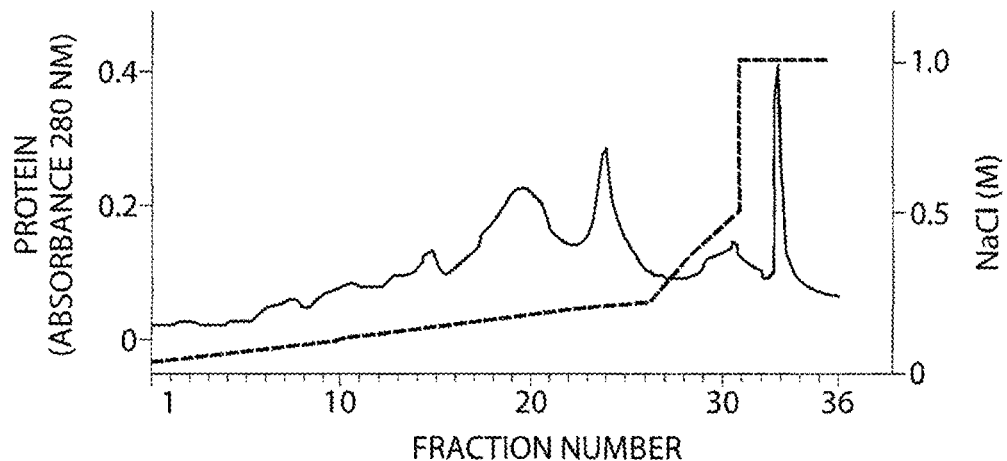

FIG. 22C is a UV-chromatogram of protein elution, into 36 fractions from the anion exchange column using G2/M phase cell lysate.

Figure 22D:
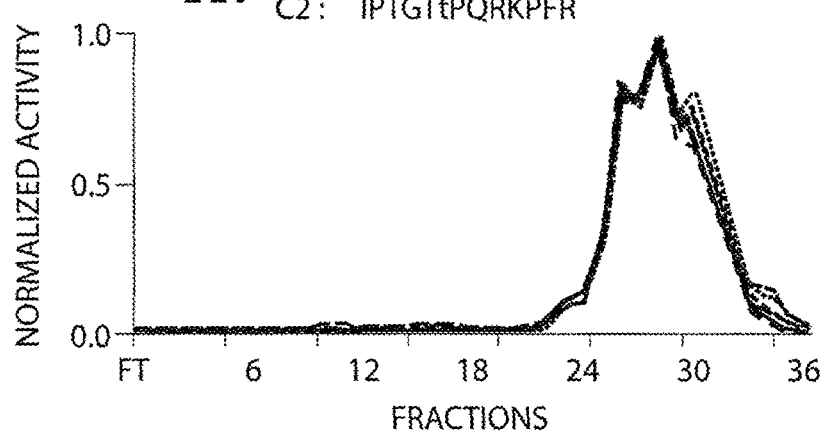

FIG. 22D is a line graph showing kinase activity profile normalized to the highest value using seven up-regulated peptides (from top: SEQ ID NOs: 2.,3.4, 10, 14. 21, 24) and the fractions in FIG. 22C.

Figure 22E:
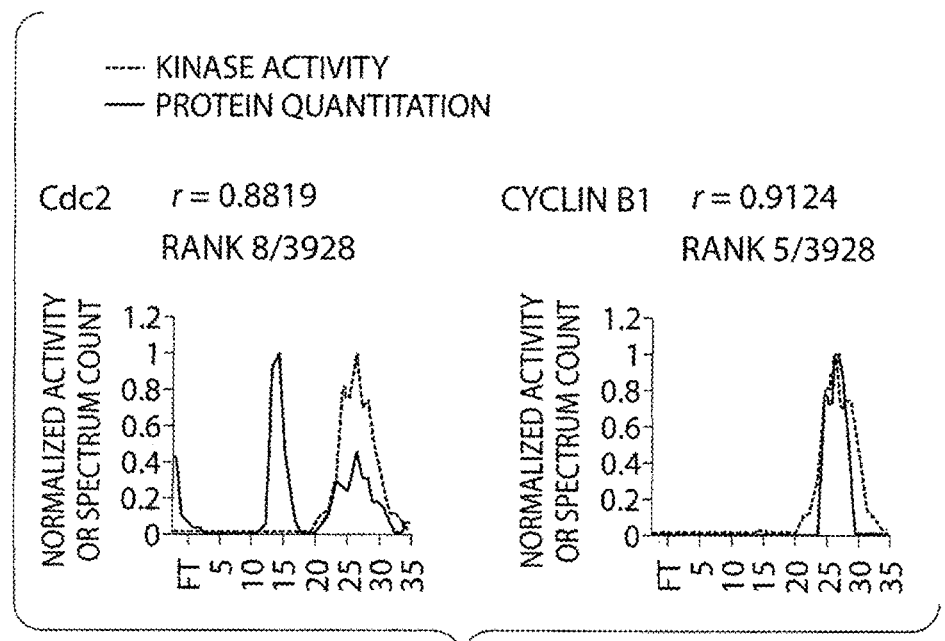

FIG. 22E is a set of line graphs showing correlation profiles of kinase activity (light gray line) and protein quantitation (dark gray line). From flow-through and 36 fractions, 3,928 proteins (116 kinases) were identified by "shotgun" LC-MS/MS analysis. Protein amount was estimated based on peptide identifications (see Examples) and normalized to the highest value. Correlation profiling ranked Cdc2 as the most likely kinase (1/116) and eighth best ranked protein overall (8/3928). In addition, the amount of Cyclin B1 was highly correlated. r-values represent Pearson product-moment correlation coefficients between peak kinase activity and protein abundance in active fractions.

Figure 22F:
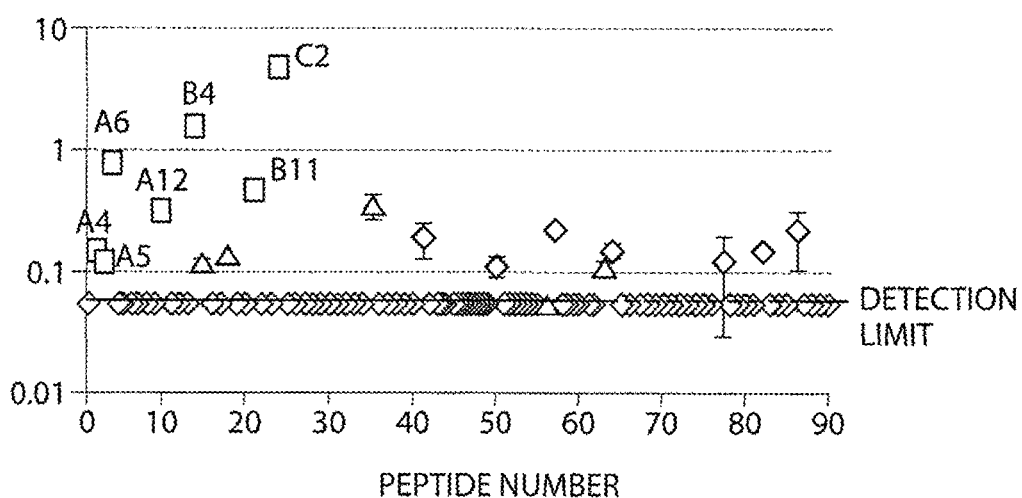

FIG. 22F is a fold-change plot showing KAYAK profiling of 90 peptides using purified Cdc2/Cyclin B1. The product amounts for the 7 peptides in FIG. 15D are shown as gray squares.

FIGS. 23A-23C are a heat map, a set of bar graphs and a set of photographs of immunoblots showing, that kinase inhibitors affect activity measurements in expected and unexpected ways.

FIG. 23A is a heat map of kinase activities. HEK293 cells were left untreated or treated with Wortmannin (PI3K inhibitor), U0126 (MEK inhibitor), Raparnycin (mTORC1 inhibitor), Akt inhibitor VIII, SB203580 (p38 MAPK inhibitor) or Go6983 (PKC inhibitor), followed by insulin stimulation. Lysates (20 μg) from each condition were analyzed by KAYAK profiling using 90 peptides. Each product amount of the observed 55 peptides was normalized by that of untreated and unstimulated lysate, followed by hierarchical clustering.

FIG. 23B is a set of bar graphs showing examples of two peptides (A3, SEQ ID NO: 1; and E11, SEQ ID NO: 57) from FIG. 23A. The data are shown as average ±s.d. (n=3). Potential identification of the kinases is made based on phosphorylation with purified kinases shown in FIGS. 14A and 14B.

FIG. 23C is a set of photographs showing Western blotting of the lysates using the indicated antibodies.

Figure 24A:
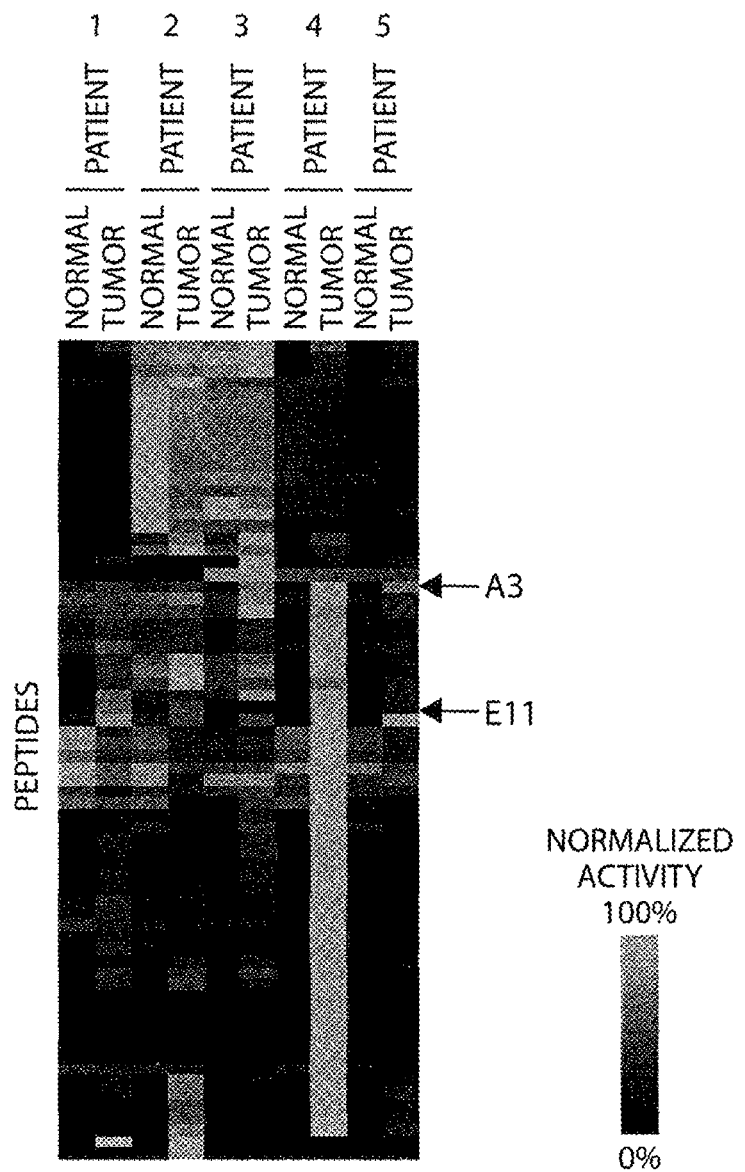

FIGS. 24A and 24 B are a heat map, a set of bar graphs and photographs of immunoblots showing,kinase activities of human renal carcinoma.

FIG. 24A is a heat map of kinase activities comparing tumor and normal tissue specimens harvested immediately after radical nephrectomy. Small pieces of normal and tumor parts from the same patients were homogenized and homogenates (20 μg) were analyzed by KAYAK using 90 peptides. Each product amount of the observed 68 peptides was normalized to the highest value for that peptide followed by hierarchical cluster analysis.

Figure 24B:
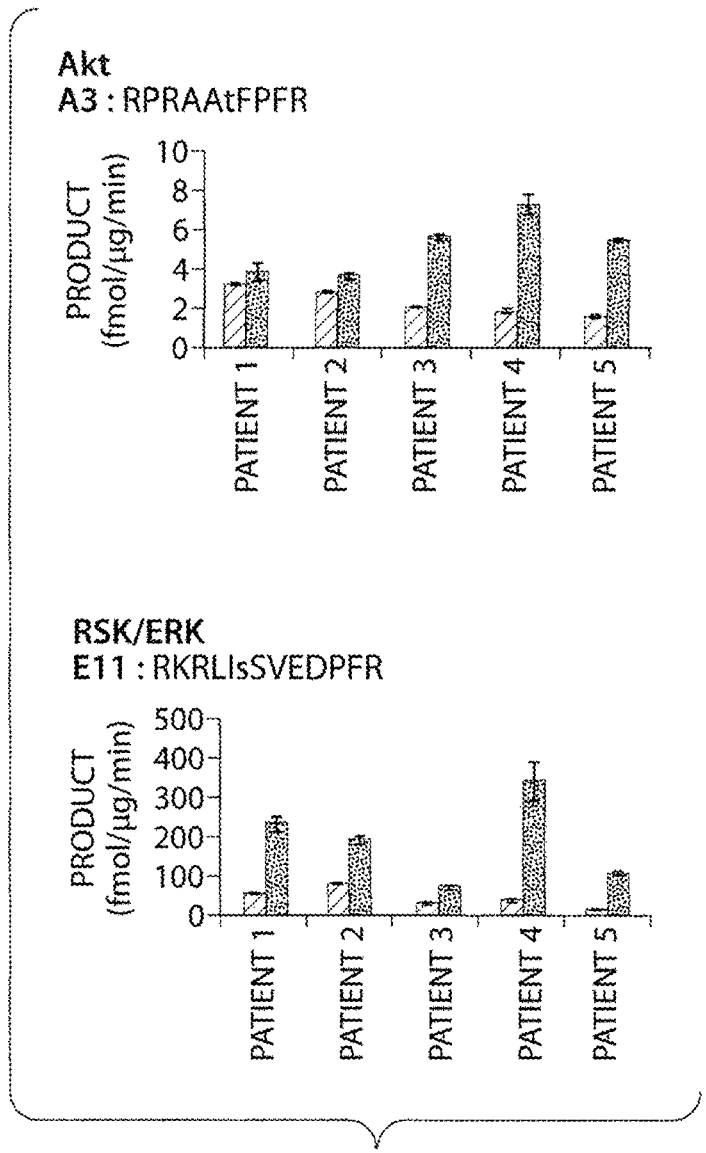

FIG. 24B is a set of bar graphs showing examples of two peptides (A3, SEQ ID NO: 1; and E11, SEQ ID NO: 57) from FIG. 24A. The data are shown as the mean of duplicate analyses with error bars at minimum and maximum values. Potential identification of the kinases is made based on phosphorylation with purified kinases shown in FIGS. 14A and 14B.

Figure 25:
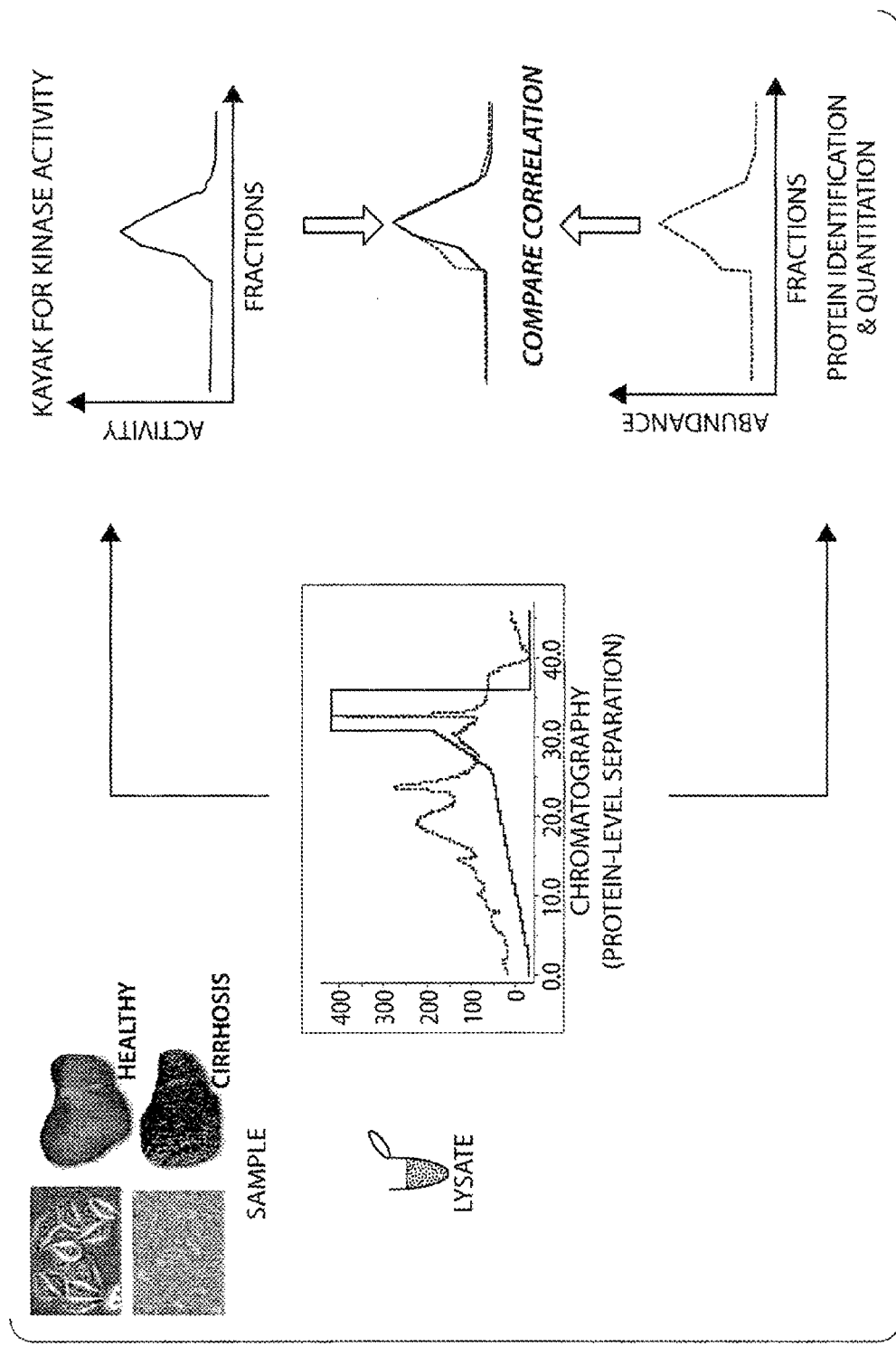

FIG. 25 is a set of photographs and line graphs showing strategy to identify the kinase for a given substrate activity. The sample of interest is fractionated by a column chromatography at protein-level. All fractions are subjected to KAYAK profiling using selected peptides of intriguing behavior to obtain kinase activity profiles over all fractions. In parallel, all fractions are digested in solution and introduced to LC-MS/MS analysis with "shotgun" sequencing to identify and quantify proteins, providing a measure of each protein's abundance in each fraction. It is expected that the protein abundance profile of the responsible kinase will correlate with the KAYAK activity profile. By calculating the observed correlation between profiles of kinase activity and protein amount across fractionated lysates, the kinase can be identified.

Figure 26A:
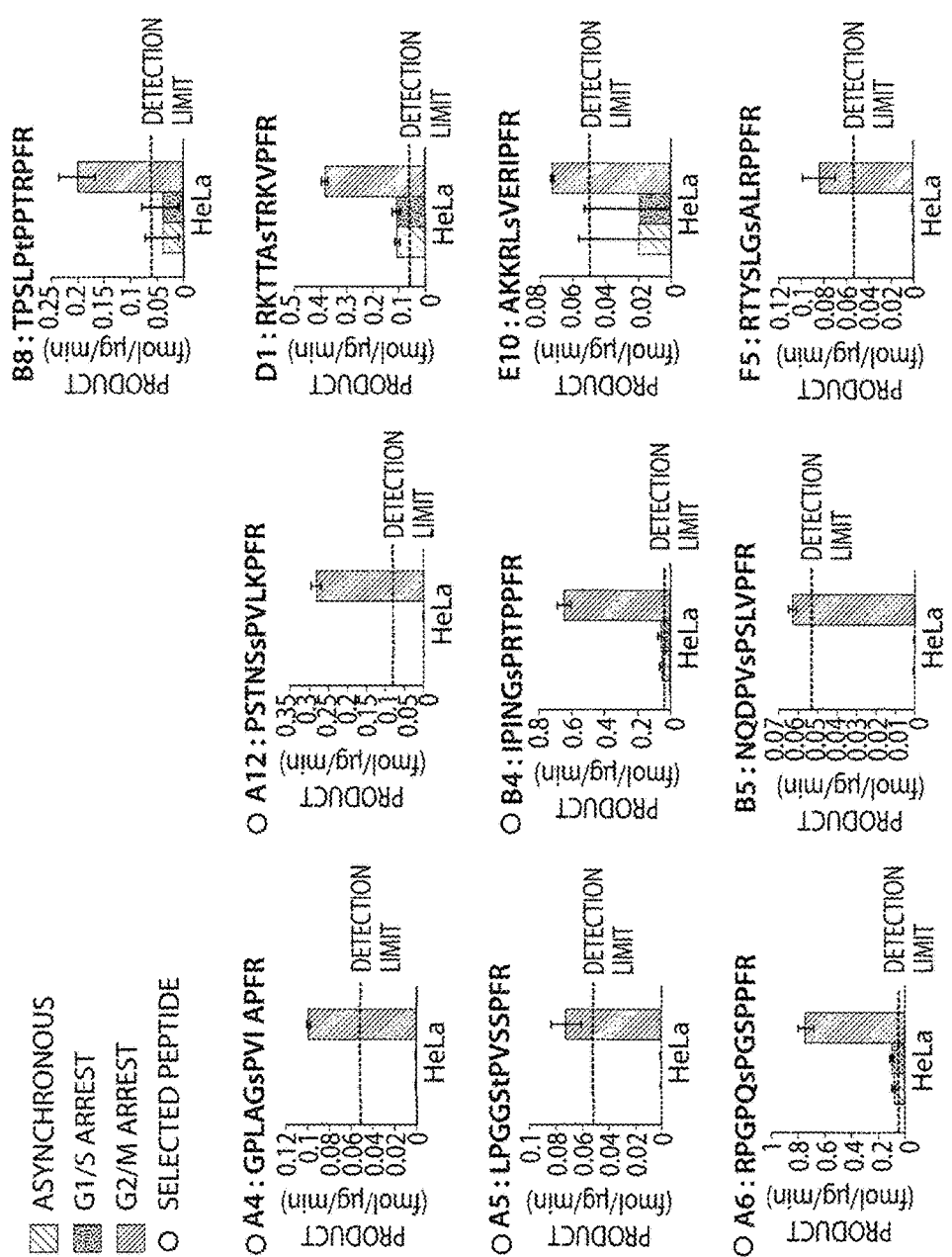
Figures 26B, 26C:
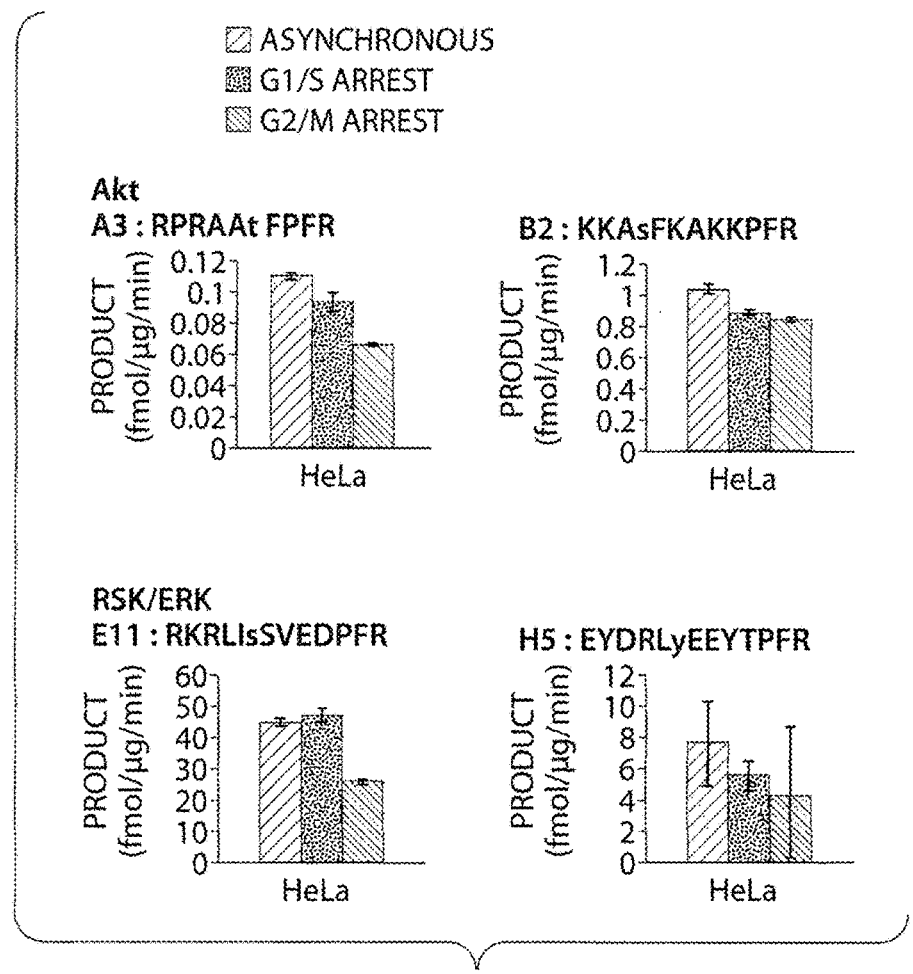

FIGS. 26A-26C is a set of bar graphs and a table showing KAYAK profiles of cell cycle analysis.

FIG. 26A is a set of bar graphs showing additional KAYAK peptide profiles (A4, A5, A6, A12, B4, B5, B8, D1, E10, F5; SEQ ID NOs: 2, 3, 4, 10, 14, 15, 18,35, 56, 63, respectively) in the upregulated cluster.

FIG. 26B is a set of bar graphs showing additional KAYAK peptide profiles (A3, B2, E11, H5; SEQ ID NOs: 1, 12, 57, 87, respectively) not in the upregulated cluster. Potential kinases are assigned based on phosphorylation with purified kinases shown in FIGS. 14A and 14B.

FIG. 26C is a table showing an overview of protein identification results for 37 fractions of separated mitotic lysate by mass spectrometry.

Figure 27A:
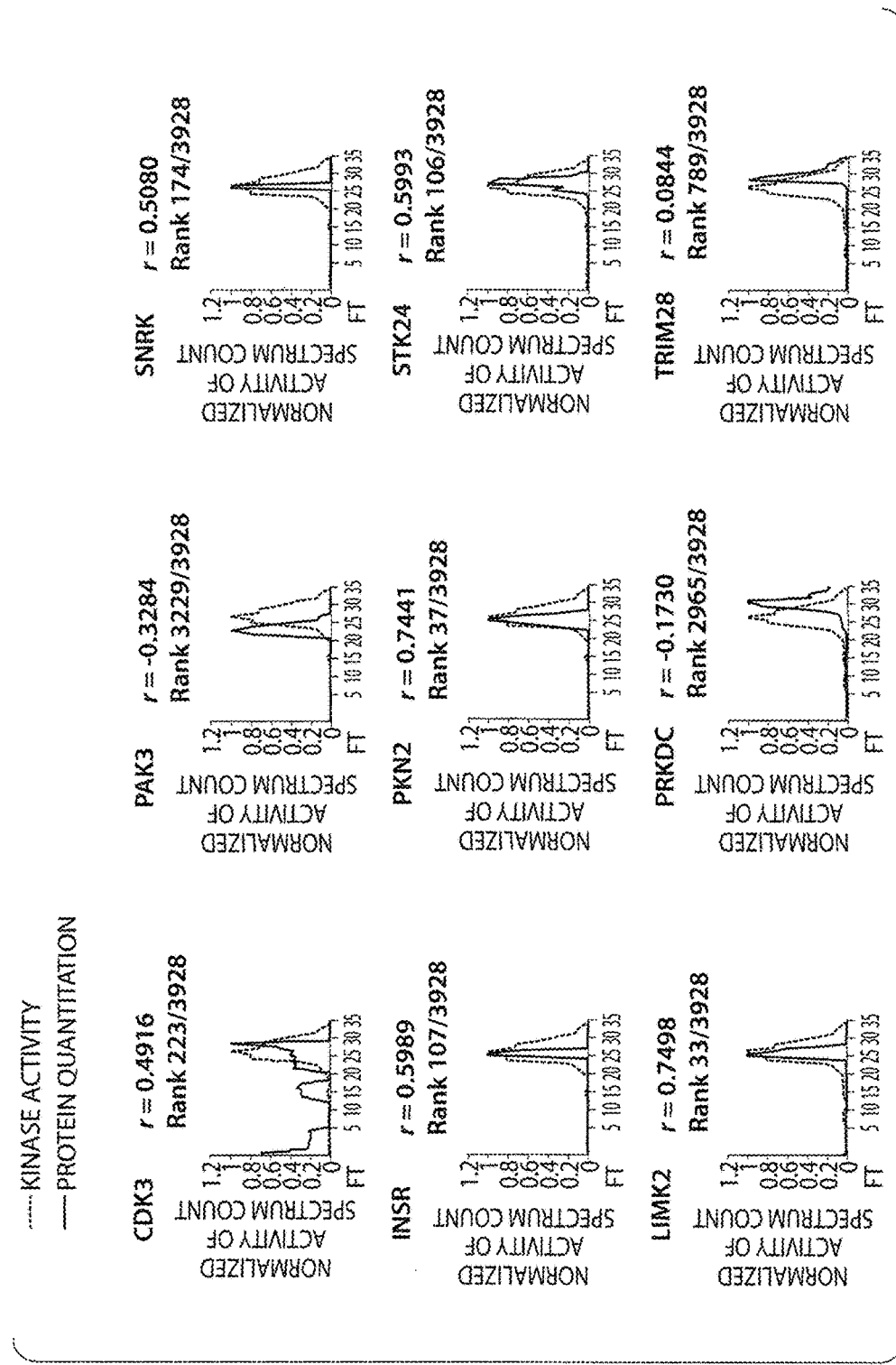
Figure 27B:
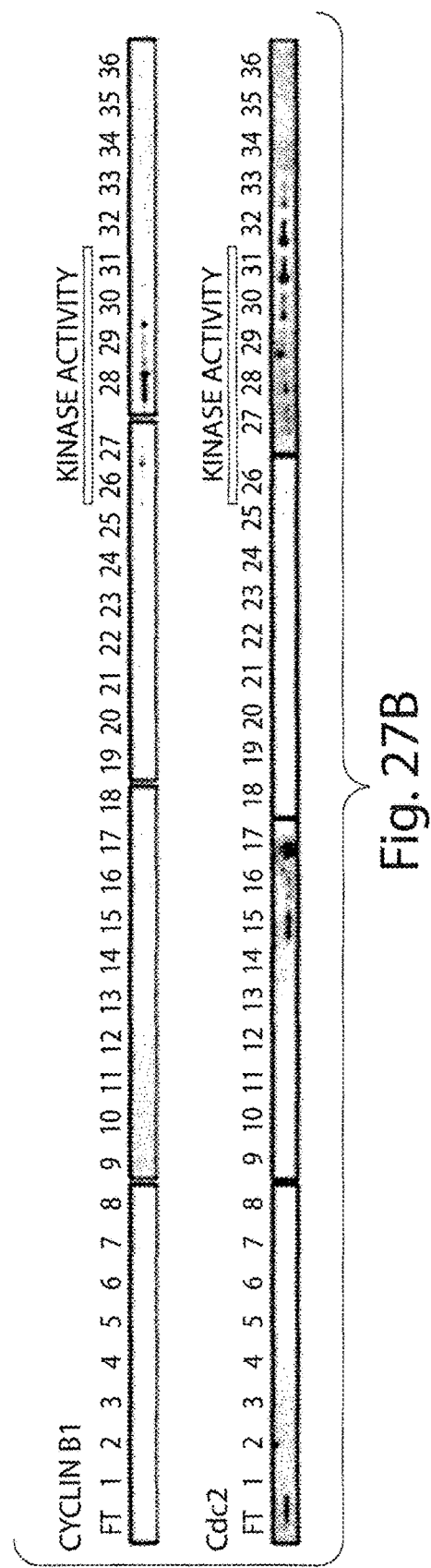

FIGS. 27A and 27B are a set of ion chromatograms and photographs of immunoblots showing KAYAK cell cycle analysis.

FIG. 27A is a set of chromatogr tivity and protein quantification. In the most active fraction (number 28) ten kinases were identified including Cdc2. The profiles of another nine kinases are shown. r-values represent Pearson product-moment correlation coefficients between peak kinase activity and protein abundance in the active fractions.

FIG. 27B is a set of photographs showing Western blotting of the anion exchange chromatography fractions using the indicated antibodies. Kinase activity peaked in fraction 28 and adjacent fractions.

DETAILED DESCRIPTION OF EMBODIMENTS

The response of kinase pathway to an external perturbation strongly depends on the internal structure of the network (Irish et al. 2004 *Cell* 118: 217-228). Therefore, inhibitor profiling is an important task. Rational information learned from kinase pathway responses to challenging with inhibitors may lead to design principles facilitating emergence of a new generation of protein kinase drugs and dosing plans targeting multiple key nodal kinases.

Strategies to measure kinase activities include the monitoring of activating phosphorylation events present on protein kinases or their substrates using phospho-specific antibodies. While these methods may serve as surrogates for kinase activation state, they are indirect measurements and are often viewed as qualitative or semi-quantitative at best. On the other hand, several strategies which do measure direct phosphorylation rates have been proposed including arrays of approximately 1000 peptides on glass slides (Diks et al. 2004 *J Biol Chem* 279: 49206-49213; Houseman et al. 2002 *Nat Biotechnol* 20: 270-274), a multiplexed kinase assay to simultaneously measure four kinase activities (Janes et al. 2003 *Mol Cell Proteomics* 2: 463-473), and a solution-phase phosphorylation reaction with 900 peptide-oligonucleotide substrates (Shults et al. 2007 *ChemBioChem* 8: 933-942). Importantly, most array-based approaches are unable to establish the actual site of phosphorylation on substrates which is important for minimizing off-target events. In addition, they do not use purified peptides, reducing the confidence in quantification accuracy. Despite the breadth of techniques available, highly quantitative and direct measurement methods are still needed to address the diverse clinical manifestations of signaling in cancer and in choosing optimal treatment options.

Chemically-synthesized peptides of optimized sequence have been utilized for more than 30 years as in vitro phosphorylation substrates using both purified kinases and cell lysates (Daile et al. 1975 *Nature* 257: 416-418; Daile et al. 1974 *Biochem Biophys Res Commun* 61: 852-858; Kemp et al. 1991 *Methods Enzymol* 200: 121-134; Kuenzel et al. 1985 *Proc Natl Acad Sci USA* 82: 737-741; Yasuda et al. 1990 *Biochem Biophys Res Commun* 166: 1220-1227). These reactions are exceptionally robust, producing femtomoles to picomoles of phosphorylated substrate from sub-ng amounts of kinases techniques (Diks et al. 2004 *J Biol Chem* 279: 49206-49213; Shults et al. 2005 *Nat Methods* 2: 277-283).

Due to its specificity and precise quantitative nature, mass spectrometry (MS) represents an ideal platform to quantify products formed from enzymatic reactions (Gao et al. 2003 *J Am Soc Mass Spectrom* 14: 173-181; Pi et al. 2002 *Biochemistry* 41: 13283-13288). Indeed, Cuttilas and coworkers elegantly demonstrated the mass-spectrometry-based quantification of Akt activity using a highly selective substrate peptide termed Aktide (RPRAATF, SEQ ID NO:1; see Table 2; Bozinovski et al. 2002 *Anal Biochem* 305: 32-39; Cuttillas et al. 2006 *Proc Natl Acad Sci USA* 103: 8959-8964).

The ability of a kinase to phosphorylate a substrate depends on many factors including substrate availability to the kinase, the physical location of both molecules and the kinase's activity state (Kemp et al. 1994 *Trends Biochem Sci* 19: 440-444). Another critical factor for kinase-substrate recognition is the linear sequence surrounding the phospho-acceptor site. Moreover, short peptide sequences derived from protein substrates often bind correctly to activated kinases resulting in phosphate transfer (Kemp et al. 1990 *Trends Biochem Sci* 15: 342-346; Pearson et al. 1991 *Methods Enzymol* 200: 62-81). Studies in the 1970s and 1980s identified several excellent peptide substrates with $K_m$ values of 1 to 5 µM for protein kinase A (PKA) and a few other kinases (Kemp et al. 1991 *Methods Enzymol* 200: 121-134). Insight into kinase substrate sequence preferences leaped forward with the advent of peptide library approaches (Songyang et al. 1994 *Curr Biol* 4: 973-982; Yaffe et al. 2001 *Nat Biotechnol* 19: 348-353) resulting in the determination of the consensus sequences for more than a hundred kinases and concomitant prediction of physiological substrates (Yaffe et al. 2001 *Nat Biotechnol* 19: 348-353; Obenauer et al. 2003 *Nucleic Acids Res* 31: 3635-3641).

An embodiment of the invention provided herein is an integrated method termed KAYAK (Kinase Activity Assay for Kinome Profiling) for multiplexed, large-scale kinase activity profiling. Quantitatively measured site-specific phosphorylation activites towards 90 different peptides using high resolution mass spectrometry was performed herein. Substrate peptides were chosen from optimized targets or from uncharacterized sites on interesting proteins to encompass diverse signaling pathways as shown in Yu et al. 2009 *Proc Natl Acad Sci USA* 106: 11606-11611, hereby incorporated by reference herein in its entirety. Peptides were in-vitro phosphorylated individually in a 96-well plate format and then stable-isotope-labeled phosphopeptides of identical sequence and known phosphorylation site were added, providing absolute quantification. The KAYAK approach was successfully applied to purified kinases, cancer cell lysates after activating or inhibiting specific pathways, and tumor samples from kidney cancer patients. Surprisingly, activities not only accurately reflected the responsible pathways, but in many cases results obtained using peptide substrates mirrored the activity at the in vivo site on the corresponding protein, showing that a collection of these peptide activities provided herein serves as an easily tractable marker of functional protein phosphorylation.

KAYAK profiling exclusively used purified peptides resulting in absolute quantification of activities which were highly linear over several logs of lysate amounts.

Because the KAYAK assay provides absolute and not relative activity measurements, basal phosphorylation levels can be directly compared from, for example, widely differing tumor and normal tissues, established cell lines, or even from specific regions of a developing mouse brain to report pathway activation state. In addition, the approach improved the kinase specificity problem inevitable from peptide-based measurements. Altered activity levels after pharmacological, environmental, or physiological pathway activation reveal tumor- or tissue-specific signaling networks, facilitating both diagnosis and personalized treatment options. In embodiments, kinase activities were measured in both tissues and cell lines with and without altered pathway activation. In every case, activation of specific pathways as measured by KAYAK peptides accurately reflected the known cell biology and Western-based findings.

Based on the many cellular settings investigated, the assay appears to faithfully report the core activation state for many pathways simultaneously including those most altered in cancer (i.e., PI3K and MAPK).

A related embodiment provided herein is a method to gain higher throughput and multiplicity by assessing phosphorylation rates for all 90 peptides in a single reaction. This strategy faithfully reports the activation of cellular signaling pathways in response to genetic and pharmacological manipulations. Moreover, in conjunction with deep protein sequencing and correlation profiling of separated lysates, a KAYAK-based strategy was used to identify direct kinase-substrate pairs and even their associated complexes. The strategy is compatible with sub-µg lysate starting amount, and faithfully reports the signatures of signaling pathways from a variety of cellular settings including cancer cell lines and tumor tissue. Hierarchal clustering of activities from related experiments grouped peptides phosphorylated by similar kinases together and, when combined with pathway alteration using pharmacological inhibitors, readily distinguished underlying differences in potency, off-target effects, and genetic backgrounds. A strategy and method to identify the kinase, and even associated complex members, responsible for a phosphorylation event of interest in our assay are shown herein.

While initially protein kinases were considered non-druggable enzymes (Cohen 1999 *Curr Opin Chem Biol* 3: 459-465), currently more than 200 kinase inhibitor candidates are at some stage of clinical development including six approved drugs for altered signal transduction therapies of cancer-relevant kinases (Margutti et al. 2007 *ChemMedChem* 2: 1116-1140). The EGFR inhibitor gefitinib has been approved for treatment of non-small cell lung cancer. However, growth and proliferation of many breast cancer cell lines are resistant to EGFR inhibition (Ferrer-Soler et al. 2007 *Int J Mol Med* 20: 3-10). Breast cancer is highly heterogeneous, often having mutation and/or overexpression of different signaling molecules within several key pathways.

The KAYAK approach in an embodiment was used to investigate the ways by which major kinase pathways may be altered as a result of the drug treatment. Overexpression of ErbB2 and RasV12 within MCF10A cells increased PI3K and MAPK activities. Although EGFR is usually coupled with PI3K pathway (Baserga 2000 *Oncogene* 19: 5574-5581), overexpression resulted in increased activities of both PI3K and MAPK pathways. In two cases (MDA-MB231 and MCF10A/RasV12), Ras mutations were found to lead to strong activation of the MAPK pathway and its insensitivity to upstream EGFR inhibition. However, the MAPK pathway in Sum159 cells showed only minor sensitivity. Activities of peptides specific for MAPK and Akt pathways in MCF7 cells, although low under basal conditions, showed decreases after gefitinib treatment Phosphorylation is the driving force behind the cell cycle (Sullivan et al. 2007 *Nat Rev Mol Cell Biol* 8: 894-903). The KAYAK assay identified a novel mitosis-specific activity for Src family kinases toward PI 3-kinase regulatory subunit p55. A KAYAK substrate peptide derived from Tyr-199 of this protein demonstrated cell-cycle-dependent phosphorylation (FIG. 7A). The site's mitosis-specific nature in vivo on p55 was confirmed (FIG. 7B). Although not immediately appreciated, PI3 kinase activity was first discovered through its co-purification with v-Src (Sugimoto et al. 1984 *Proc Natl Acad Sci USA* 81: 2117-2121). Crystallography studies of the PI 3-kinase p110α/p85α complex show that Tyr-467/p85α (homologous to Tyr-199/p55γ) is localized at the interface between the inter-SH2 domain of p85α and the C2 domain of p110α (Huang et al. 2007 *Science* 318: 1744-1748). Specifically, Tyr-467 is 2.7 Ångstroms away from His-450 of the catalytic subunit, within the distance for potential hydrogen bond formation (FIG. 12D). This interaction and even the interface will likely be disrupted by phosphorylation of Tyr-467. The monomeric form of the regulatory subunit is unstable in cells (Brachmann 2005 *Mol Cell Biol* 25: 1595-1607; Zhao et al. 2006 *Proc Natl Acad Sci USA* 103: 16296-16300). This could explain finding that p55γ was degraded after prolonged Src activation. Since Tyr-467 is buried in the interface and the PI 3-kinase has shown to be a stable complex (Geering et al 2007 *Proc Natl Acad Sci USA* 104: 7809-7814), it is possible that phosphorylation of this site regulates the interaction between the newly synthesized subunits. Many cancer mutations of PI 3-kinase have been mapped to this inter-domain region, including N345K (p110α), E453Q (p110α), C420R (p110α), E439del (p85Ξ) and KS459de1N (p85α; Huang et al. 2007 *Science* 318: 1744-1748; McLendon et al. 2008 *Nature* 455: 1061-1068). These mutations probably change the interaction between the two subunits, resulting in constitutively elevated PI 3-kinase activity. Moreover, transfection of p110α harboring these mutations lead to both Akt activation and transformation of chicken embryo fibroblasts (Gymnopoulos et al. 2007 *Proc Natl Acad Sci USA* 104: 5569-5574). Therefore, phosphorylation of Tyr-199 on the regulatory subunit could also be a mechanism for SFK (Src family kinases)-dependent regulation of PI 3-kinase activity.

The renal cell carcinoma tissue results have exceptional promise in the field of clinical proteomics. Samples in this discipline are often obtained from biopsies, laser-capture-microdissect ion, or cell sorting experiments. The number of cells available in these sample types often falls far short of what has been used for direct profiling of phosphorylation events ($10^7$-$10^9$ cells; Dephoure et al. 2008 *Proc Natl Acad Sci USA* 105. 10762-10767; Matsouka et al. 2007 *Science* 316: 1160-1166). Kinase activity measurements overcome sensitivity pitfalls through a highly amplified process where zeptomole amounts of enzyme can produce mass-spectrometry-amenable levels (>1 fmol). For this reason, activity measurements have been described as analogous to polymerase chain reaction for protein (Cutillas et al. 2006 *Proc Natl Acad Sci USA* 103: 8959-8964). The reported KAYAK activities directly reflected pathway activation state as measured by antibody-based methods.

An unexpected finding from this work was that peptide substrate activity measurements sometimes accurately reflect the phosphorylation status of the analogous protein as, for example, demonstrated for H5 peptide derived from PI3K regulatory subunit p55. Another peptide E11 (RKRL-IsSVEDPFR; SEQ ID NO: 57; Roux et al. 2004 *Proc Natl Acad Sci USA* 101: 13489-13494) was derived from a tuberin site phosphorylated in vivo by both Akt and RSK with preferential phosphorylation by RSK. This peptide showed upregulated phosphorylation after both insulin and EGF stimulation, with higher phosphorylation levels detected for EGF. Likewise, several peptides from known CDK substrates were modified by mitotic extracts including A12, B4, B11, C2 and D10. While not true for all substrate peptides, it may be that a majority of substrates are phosphorylated in ways that mimic their protein counterparts. Indeed, these same protein counterparts are often present in the lysates and may introduce additional context to allow phosphorylation. Important exceptions were peptides derived from autophosphorylation sites on EGFR. These tyrosine-containing peptides were not observed to be phosphorylated, requiring a context which includes receptor dimerization and transphosphorylation (Hackel 1999 *Curr Opin Cell Biol* 11: 184-189). In any event, these results strongly suggest that kinase substrates that are biochemically difficult or impossible to study in a signaling context either because of solubility, extreme size, or abundance levels, now may be approached through these methods, uncovering clues to the responsible kinase and even the site's functional significance.

The strategy behind the KAYAK approach is applicable to additional enzyme classes. Specifically, mass-spectrometry-determined protease activities from plasma samples may act as accessible disease biomarkers. In addition, histone de-acetylases and tyrosine phosphatases would have obvious value given their importance as drug targets. Multiplexed peptide-based activity assays, exploiting high resolution mass spectrometry, may become a mainstay of clinical diagnosis, rational drug design, and disease prognosis.

While in vitro phosphorylation using purified kinases (FIGS. 14A and 14B) catalogued likely kinase candidates for most phosphorylation events, identification of the responsible kinase directly from cell lysates provides certainty. However, developing a general methodology to identify a kinase responsible for a specific phosphorylation event is challenging (Parang et al. 2002 *FEBS Lett* 520: 156-160; Shen et al. 2003 *J Am Chem Soc* 125: 16172-16173; Linding et al. 2007 *Cell* 129: 1415-1426; Johnson et al. 2005 *Nat Methods* 2: 17-25). In contrast, identifying a phosphorylation event using a specific kinase is straight-forward via several practical methodologies (Manning et al. 2002 *Sci STKE* 2002: PE49). For instance, a series of chemical reagents which can cross-link a kinase and a substrate showed promising results. Nevertheless, the reagents have not been shown to work in complex situations such as assays of crude cell lysates (Maly et al. 2004 *J Am Chem Soc* 126: 9160-9161; Statsuk et al. 2008 *J Am Chem Soc* 130: 17568-17574). Traditionally, identification of a responsible enzyme for a specific activity has been accomplished by comparing enzymatic activity and a protein band after SDS-PAGE gel separation. The correlation of a protein band with an activity requires, however, multiple purification steps. Owing to the advancement of protein quantification by mass spectrometry (Domon et al. 2006 *Science* 312: 212-217), correlation profiles have been used to determine protein localization by mass spectrometry (Andersen et al. 2003 *Nature* 426: 570-574; Andersen et al. 2005 *Nature* 433: 77-83; Foster et al. 2006 *Cell* 125: 187-199). Thus, the classic concept of comparing enzyme activity and protein profiles can be renewed using modern quantitative proteomics technology. The strategy reported here is a general methodology to decipher kinase-substrate relationships starting with a phosphorylated peptide substrate and a simply fractionated lysate.

Phosphoproteomics projects have delivered atlases of experimentally mapped phosphorylation sites (Beausoleil et al. 2004 *Proc Natl Acad Sci USA* 101: 12130-12135; Villen et al. 2007 *Proc Natl Acad Sci USA* 104: 1488-1493; Rikova et al. 2007 *Cell* 131: 1190-1203; Wilson-Grady et al. 2008

*J Proteome Res* 7:1088-1097; Zhai et al. 2008 *J Proteome Res* 7: 1675-1682; Dephoure et al. 2008 *Proc Natl Acad Sci USA* 105: 10762-10767; Olsen et al. 2006 *Cell* 127: 635-648). However, many phosphorylation sites/motifs have not yet been associated with a kinase, and may be referred to as "orphan" (Statsuk et al. 2008 *J Am Chem Soc* 130: 17568-17574). Indeed, one unpredicted peptide was found herein to be phosphorylated by Cdc2/Cyclin B1 complex in a specific cellular context. Although a fraction of these sites may be phosphorylated in the context of the appropriate three-dimensional protein fold, most would be expected to be phosphorylated with a high degree of specificity due to primary sequence determinants. The combination of activity profiles and protein correlation profiling bridges the gap between large scale phosphoproteomics work to characterize phosphorylation events, their focused biological context, and their function.

A portion of this work was published in a paper entitled "A site-specific, multiplexed kinase activity assay using stable-isotope dilution and high-resolution mass spectrometry" by Yonghao Yu, Rana Anjum, Kazuishi Kubota, John Rush, Judit Villen, and Steven P. Gygi 2009 *Proc Natl Acad Sci USA* 106: 11606-11611, which is hereby incorporated herein by reference in its entirety.

The invention having been fully described, the following examples and claims are exemplary and are not intended to be further limiting. The contents of all references cited are hereby incorporated herein by reference.

EXAMPLES

Example 1

Materials

Peptides were synthesized in a 96-well format using a MultiPep from Intavis Bioanalytical Instruments AG. Preloaded NovaSyn Tentagel resins and fluorenylmethoxycarbonyl-derivatized phosphoamino acid monomers from Novabiochem. Heavy-isotope phosphopeptides were synthesized at 2-μmol scale and contained one residue of L-Pro-N-Fmoc (U-13C5, 97-99%; 15N, 97-99%; CNLM-4347; Cambridge Isotope Laboratories). Normal-isotope peptides were made at 5-μmol scale. Amino acids activated in situ with 1-H-benzotriazolium, 1-[bis(dimethylamino) methylene]-hexafluoro-phosphate (1),3-oxide:hydroxybenzotriazole hydrate and 4-methylmorpholine were coupled at a 5-fold molar excess over peptide. Each coupling cycle was followed by capping with acetic anhydride to avoid accumulation of 1-residue deletion peptide byproducts. After synthesis, peptide-resins were treated with a standard scavenger-containing trifluoroacetic acid-water cleavage solution, and the peptides were precipitated by addition to cold ether. Peptides were purifid by semipreparative HPLC separation and quantified with 2,4,6-trinitrobezenesulphonic acid (Fields 1971 *Biochem J* 124:581-590).

Purified human active kinases of Akt1 (full length), extracellular signal-regulated kinase 1 (ERK1, 1-379), mitogen-activated protein kinase kinase 1 (MEK1, 1-393), 90 kDa ribosomal S6 kinases 1 (RSK1, 1-735), cAMP-dependent protein kinase (PKA) catalytic subunit-α (PKA Cα, 1-351), protein kinase Cα (PKCα, full length), epidermal growth factor (EGF) receptor (EGFR, 672-1210), platelet-derived growth factor (PDGF) receptor α (PDGFRα, 550-1090), vascular endothelial growth factor (VEGF) receptor 1 (VEGFR1 784-1338), Src (full length), casein kinase 2 (CK2, full length), Aurora A (1-403), AMP-activated protein kinase α1β1γ1 (AMPK α1β1γ1, full length), glycogen synthase kinase-3α (GSK-3α, 1-483) and MAP/microtubule affinity-regulating kinase 1 (MARK 1, full length) were obtained from Cell Signaling Technology (Danvers, Mass.). Cdc2/cyclin B1 (full length) and insulin-like growth factor (IGF)-I receptor (IGFIR, 959-1367) were obtained from Upstate (Temecula, Calif.).

Antibodies specific for the following proteins were used for Western blot analysis: phospho-RSK (Thr-359/Ser-363), RSK, Akt, phospho-Akt (Ser-473), ERK1/2, phospho-S6 (Ser-235/236), phospho-PI3K regulatory subunit p85(Tyr-467)/p55(Tyr-199), actin, histone H3, Src, phospho-Src (Tyr-416), phospho-retinoblastoma protein (Ser-780), phospho-tyrosine(p-Tyr-100), phospho-threonione-proline (p-Thr-Pro-101; Cell Signaling Technology), phospho-ERK1/2 (Thr-202/Tyr-204; Sigma) and PI3 kinase regulatory subunit p55γ (Santa Cruz Biotechnology). U0126 and Wortmannin were obtained from Sigma and SU6656 was purchased from Calbiochem. Gefitinib was purchased from LC laboratories (Woburn, Mass.).

Antibodies specific for the following proteins: phospho-tyrosine (P-Tyr-100), EGF receptor, phospho-EGF receptor (Y1086), Akt, phospho-Akt (S473), Erk1/2, phospho-ERK1/2 (T202/Y204), S6 ribosomal protein, phospho-S6 ribosomal protein (S235/S236), actin, cyclin B1, Cdc2, Src, IGF-I receptor β, Mst3, phospho PKC (βII S660), phospho VASP (S157) and phospho-PKA C (T197) were obtained from Cell Signaling Technology. Horse radish peroxidase (HRP)-linked antibodies specific for rabbit and mouse IgG were obtained from GE Healthcare (Uppsala, Sweden).

Example 2

Mammalian Cell Culture, Transfection and Lysis

HEK293 (embryonic kidney), HeLa (cervical cancer), U-87 MG (glioma), DU 145 (prostate cancer), LNCaP (prostate cancer), BJ (foreskin fibroblast), and A2780 (ovarian cancer) cells were maintained in Dulbecco's modified Eagle's medium (DMEM) supplemented with 10% fetal bovine serum (FBS). T-47D (breast cancer) cells were maintained in RPMI-1640 medium with 10% FBS and 0.2 U/ml bovine insulin. PC-3 (prostate cancer) cells were maintained in F-12K medium with 10% FBS. U-2 OS (osteocarcinoma) cells were maintained in McCoy's 5a medium with 10% FBS. Jurkat (human T lymphocyte) cells were maintained in RPMI1640 medium with 10% FBS.

MCF7 and MBA-MB231 cells were maintained in DMEM supplemented with 10% FBS. Sum159 cells were maintained in Ham's F12 media supplemented with 5% FBS, 5μg/ml hydrocortisone. MCF10A, MCF10A, ErbB2, MCF10A/IGFR, and MCF10A/H-Ras$^{G12V}$ cells were generously provided by J. Brugge (Debnath et al. 2002 *Cell* 111: 29-40; Irie et al. 2005 *J Cell Biol* 171: 1023-1034; Reginato et al. 2003 *Nat Cell Biol* 5: 733-740) and were maintained in 50/50 DMEM/F12 media supplemented with 5% horse serum, 20 ng/ml EGF, 100 ng/ml cholera toxin, 10 μg/ml insulin, and 500 ng/ml hydrocortisone. Breast cancer cells were treated also with 1 μM of gefitinib (LC laboratories) for 24 h before lysis and KAYAK analysis. The mutation data was obtained from Wellcome Trust Sanger Institute Cancer Genome Project Web site (Hollestele et al. 2007 *Mol Cancer Res* 5:195-201).

For stimulation of HEK293 cells or HeLa lines, cells were treated with insulin (100 nM; 10-30 min) EGF (50 ng/ml; 10 min) or phorbol 12-myristate 13-acetate (PMA; 50 or 100 ng/ml; 10 -30 min) at 37° C. for the indicated times after overnight serum-starvation.

For inhibitor experiments, HEK293 cells were treated with 100 nM Wortmannin (PI3K inhibitor), 5 µM U0126 (MEK inhibitor), 25 nM rapamycin (mTORC1inhibitor), 1 µM Akt inhibitor VIII, 10 µM SB 203580 (p38 MAPK inhibitor) or 1 µM Go6983 (PKC inhibitor) for 30 min after overnight serum-starvation, and stimulated with 100 nM insulin for 30 min.

For drug inhibition studies, cells were pretreated with U0126 (5 µM) or Wortmannin (100 nM) for 1 hr prior to hormone stimulation.

For small interfering RNA (si-RNA) studies, 21 nucleotide complementary RNA with symmetrical 2 nucleotide overhangs were obtained from Qiagen. The DNA sequences used to prepare double-stranded RNAs for RSK1 and RSK2 were created CCC AAC ATC ATC ACT CTG AAA (SEQ ID NO: 91) and AGC GCT GAG AAT GGA CAG CAA (SEQ ID NO: 92), respectively. HEK293 cells were transfected by the calcium-phosphate procedure using 1 to 2 µg each A per 100-mm dishes. Transfection efficiency was determined to be greater than 95% using a fluorescently labeled mock siRNA. Twenty-four hours following transfection, cells were serum-starved for 16 to 18 h, stimulated with EGF, and then harvested. The lysates were centrifuged for 10 min at 4° C., and were immunoblotted.

For cell cycle examples, HeLa cells were synchronized by double thymidine block for G1/S-arrest and by 0.2 µg/ml nocodazole for G2/M-arrest as described (Dephoure et al. 2008 *Proc Natl Acad Sci USA* 105: 10762-10767). Synchronization was confirmed by flow cytometry.

For cell lysis, the media were removed, and cells were washed with ice-cold phosphate-buffered saline (PBS) and lysed with ice-cold lysis buffer (10 mM $K_2HPO_4$ pH 7.5, 1 mM EDTA, 10 mM $MgCl_2$, 50 mM β-glycerophosphate, 5 mM EGTA, 0.5% Nonidet P-40, 0.1% Brij 35, 0.1% deoxycholic acid, 1mM sodium orthovanadate, 1mM phenylmethyl-sulfonyl fluoride, 5 µg/ml leupeptin and 5 µg/ml pepstatin A). Lysates were centrifuged at 10,000 rpm for 10 min to remove cell debris, and clear supernatant was used for immunoblotting and in vitro kinase assays. Protein concentration was determined by Bradford assay (Biorad, Hercules, Calif.).

Alternatively, cells were washed with PBS once and lysed with ice-cold lysis buffer, 10 mM potassium phosphate, pH 7.0, containing 0.5% NP-40, 0.1% Brij 35, 0.1% deoxycholic acid, 1 mM ethylenediaminetetraacetic acid (EDTA), 5 mM ethylene glycol tetraacetic acid (EGTA), 10 mM $MgCl_2$, 50 mM β-glycerophosphate, 1 mM $Na_3VO_4$, 2 mM dithiothreitol (DTT) and protease inhibitor cocktail (Complete, Roche Applied Science, Indianapolis, Ind.). Homogenates were centrifuged at 10,000 rpm for 15 min at 4° C., and the supernatant was used as lysate. Protein concentration was quantified by a modified Bradford assay (Pierce).

Example 3

Anion Exchange Chromatography

Purification steps were conducted at 4° C. Eight milligrams of the HeLa cell lysate from cells arrested in G2/M phase were dialyzed against AEX buffer (20 mM HEPES, pH 7.5, containing 0.5% NP-40, 0.1% Brij 35, 0.1% deoxycholic acid, 1 mM EGTA, 5 mM $MgCl_2$, 5 mM β-glycerophosphate, 0.1 mM $Na_3VO_4$, 0.1 mM DTT, protease inhibitor cocktail and 20% glycerol). The dialyzed sample was centrifuged, the supernatant was loaded onto an anion exchange column (Mono Q 5/50 GL, GE Healthcare), and proteins were eluted into 36 fractions (1 ml each) with a gradient of 0-1 M NaCl in AEX buffer. Thirty microliters from the flow through and 36 fractions were subjected to KAYAK profiling using a subset of the 90 peptides. An aliquot (200 µl) of each fraction was also reserved for LC-MS/MS analyses (protein identification and quantitation).

Example 4

KAYAK

Peptides were synthesized, purified and quantified as described in Yu et al. 2009 *Proc Natl Acad Sci USA* 106: 11606-11611, hereby incorporated by reference herein in its entirety. Each substrate peptide (250 pmol) was mixed to a final concentration of 5 µM in the 50 µL reaction mixture. Alternatively, reactions were performed using 6 µg cell lysate aliquotes mixed to a final volume of 20 µl. Cell lysate or other kinase source was added to the substrate mixture in 25 mM Tris-Cl, pH 7.5, containing 5 mM ATP, 7.5 mM $MgCl_2$, 0.2 mM EGTA, 7.5 mM β-glycerophosphate, 0.1 mM $Na_3VO4$, and 0.1 mM DTT. The reaction was incubated at 25° C. for 60 min and then terminated by the addition of 100 µl of 1% trifluoroacetic acid (TFA) containing a known amount of an internal standard (typically 20 pmol). Alternatively, the reaction was incubated at 20° C. for 45 min before termination with TFA.

Forty-five individual in vitro kinase reaction mixtures were combined and desalted by using Sep-Pak C18 cartridge (Waters, Milford, Mass.). Phosphopeptides were enriched by immobilized metal ion chromatography (IMAC) with 20 µl of beads (Phos-Select iron affinity gel; Sigma, St. Louis, Mo.) and subsequently desalted by using Empore C18 solid phase extraction disks (3M, St. Paul, Minn.) as described previously.

Internal standard heavy peptides (5 pmol each) were added as a mixture to the terminated reactions followed by desalting with a solid phase extraction cartridge (SepPak tC18 (50 mg), Waters, Milford, Mass.). Phosphopeptides were enriched as described (Villen et al. 2008 *Nat Protoc* 3: 1630-1638). In brief, desalted peptide mixtures were dried down in a centrifuge evaporator and mixed with 15 µl of immobilized metal chelating chromatography (IMAC) resin (PHOS-Select, Sigma, St. Louis, Mo.) pre-equilibrated with 25 mM formic acid (FA) containing 40% acetonitrile (ACN). After incubating at 20° C. for 1 hour, the suspension was transferred to the top of a StageTip (Rappsilber et al. 2007 *Nat Protoc* 2: 1896-1906) packed with Empore disk C18. The resin was washed twice with 25 mM FA containing 40% ACN and once with 0.1% TFA, and bound phosphopeptides were eluted from the resin to the Empore disk with three washes of 500 mM potassium phosphate, pH 7.0. The Empore disk was washed once with 0.1% TFA and 1% FA. Purified phosphopeptides were eluted with 1% acetic acid containing 50% ACN.

Example 5

Solution Digestion of Protein in AEX Fractions

Proteins contained in 200 µl of each fraction were precipitated with methanol/chloroform (Wessel et al. 1984 *Anal Biochem* 138: 141-143) after adding 500 fmol BSA as an internal standard. Precipitates were washed with ice-cold acetone and dissolved in 50 mM Tris-Cl, pH 7.5, containing 8 M urea, 50 mM EDTA and 0.005% n-dodecyl β-D-maltoside (DM). Proteins were reduced with 10 mM DTT at 37° C. for 20 min and alkylated with 20 mM iodoacetamide at 20° C. for 20 min in the dark. After diluting urea concentration to 1 M with 50 mM Tris-Cl, pH 7.5, containing 0.005% DM, trypsin was added to a final concentration of 5 ng/μl, and proteins were digested in solution at 37° C. for 12 hour. Reaction was stopped with FA, and the resultant peptides were desalted with StageTips (Rappsilber et al. 2007 Nat Protoc 2: 1896-1906).

Example 6

LC-MS and LC-MS/MS

Samples were analyzed with an LTQ-FT or LTQ-orbitrap mass spectrometer (ThermoFisher, San Jose, Calif.) using LC-MS conditions described previously (Villen et al. 2007 Proc Natl Acad Sci USA 104: 1488-1493). Briefly, peptides were separated on a hand-pulled fused silica microcapillary (125 μM×15 cm, packed with Magic C18AQ, Michrom Bioresources, Auburn, Calif.) using a 45 min linear gradient ranging from 10% to 37% ACN in 0.1% FA. For each cycle, one full, high-resolution MS scan was acquired ($10^6$ ion AGC setting), followed by two MS/MS scans in the linear ion trap.

Quantitation of the target peptide-internal standard ratios was performed by first constructing the extracted ion chromatogram for the most abundant charge state for each peptide using a ±10 ppm window. Chromatograms were integrated using Qual/Quan browser (Xcalibur 2.0.5, Thermo Fisher, San Jose, Calif.). Since the phosphorylated peptides generated from the in vitro kinase reactions were chemically identical to the internal standards, they were assumed to have the same ionization efficiency. Therefore, the amount of each phosphorylated peptide was calculated by direct ratio to the internal standard level.

For KAYAK analyses, phosphopeptides were dissolved in 5% FA and injected onto a 125-μm-internal diameter fused silica column packed with Magic C18 AQ material (Michrom Bioresources, Auburn, Calif.). Peptides were separated using a two-solvent system: solvent A (0.125% FA and 3% ACN in $H_2O$), solvent B (0.125% FA in ACN) over 32 min gradient, and eluting peptides were directly analyzed using an LTQ-Orbitrap mass spectrometer (Thermo Scientific, San Jose, Calif.) equipped with the electron transfer dissociation option. Data were collected such that one survey scan in Orbitrap (400-900 m/z full MS; 60,000 resolution setting; AGC setting of $10^6$; ion fill time maximum of 1 s). If localization of phosphorylation site was uncertain, MS/MS scans in the liner ion trap using collision-induced dissociation and/or electron transfer dissociation were collected. Precursor ions were chosen for sequencing based on mass lists containing predicted m/z values for each light and heavy phosphopeptide (tolerance of ±5 ppm). Following analysis, extracted ion chromatograms were drawn from the high resolution survey scan with ±10 ppm mass accuracy, and the product amount was quantified from the ratio of the areas under the curve of the light-to-heavy phosphopeptide. Heavy and light pairs were required to perfectly co-elute. Measurements where the peak height was less than $10^4$ counts or peak areas less than 1% of the internal standard (50 fmol) were regarded as not detected.

For shotgun sequencing experiments of digested AEX fractions, peptides were re-dissolved with 5% FA containing 5% ACN. Liquid chromatography conditions were the same as described except a 50-min gradient was used. The LTQ-Orbitrap was operated in the data-dependent mode with dynamic exclusion (30 s), where the high resolution survey scan was followed by ten MS/MS scans collected in the linear ion trap on the 10 most abundant precursor ions, as described previously (Haas et al. 2006 Mol Cell Proteomics 5: 1326-1337). The obtained MS/MS data were searched against the IPI human database (Kersey et al. 2004 Proteomics 4: 1985-1988) using the SEQUEST algorithm (Eng et al. 1994 J Am Soc Mass Spectrom 5: 976-989). Peptides were filtered using Xcorr, ΔCorr, mass accuracy and peptide length with in-house software to a false discovery rate of <1% at the peptide level by the target-decoy approach (Elias et al. 2007 Nat Methods 4: 207-214). Protein amounts in each fraction were estimated by spectral counting normalized by the count of internal standard (BSA) peptides. A Pearson product-moment correlation coefficient was calculated for each protein comparing a given kinase activity and protein abundance estimate across all fractions containing at least 5% of the kinase activity in the most active fraction. Gene symbols of kinases were adopted from the updated gene symbol lists (http://kinase.com) assembled by Manning and colleagues (Manning et al. 2002 Science 298: 1912-1934).

Example 7

Western Blot

Lysates were resolved on 4 to 12% SDS/PAGE, transferred onto Potran membranes (Whatman), blocked with 3% milk in TBST (Tris Buffered Saline Tween-20), incubated with 1:1,000 dilution of primary antibody at 4° C. overnight, washed, and incubated with a 1:5,000 dilution of second antibody (HRP-conjugated) with 3% milk in TBST for 1 h at room temperature. Bands were visualized with ECL solution (Roux et al. 2004 Proc Natl Acad Sci USA 101: 13489-113494).

Example 8

The KAYAK Strategy for Parallel Measurement of Kinase Pathway States

For substrates, 90 peptides and an additional 90 same-sequence reference "heavy" phosphopeptides (Table 2) were synthesized based on either their ability to be selectively phosphorylated or from uncharacterized sites found in our previous large-scale in vivo phosphoproteomics studies (Ballif et al. 2004 Mol Cell Proteomics 3: 1093-1101; Villen et al. 2007 Proc Natl Acad Sci USA 104: 1488-1493; Dephoure et al. 2008 Proc Natl Acad Sci USA 105: 10762-10767). Each peptide contained an additional C-terminal extension tripeptide, the tripeptide Pro-Phe-Arg, or in one letter amino acid terminology, PFR to incorporate same-position (proline) heavy isotope during synthesis in a plate format, enhance chromatographic retention/UV absorption for purification (phenylalanine), and facilitate ionization and fragmentation by MS/MS. No difference was observed in phosphorylation rates for known peptide substrates with or without the additional C-terminal tripeptide.

To test substrate suitability in a multiplexed assay, the phosphorylation activities were measured using 100 μM of each substrate peptide, 6 μg lysate, and 5 mM ATP in a plate format. Reactions proceeded for 60 minutes followed by acidification and the addition of isotope-labeled reference peptides. After pooling 45 samples, phosphopeptide enrichment was followed by liquid-chromatography (LC) separation and on-line peptide detection by high-resolution mass spectrometry.

Figure 1A:
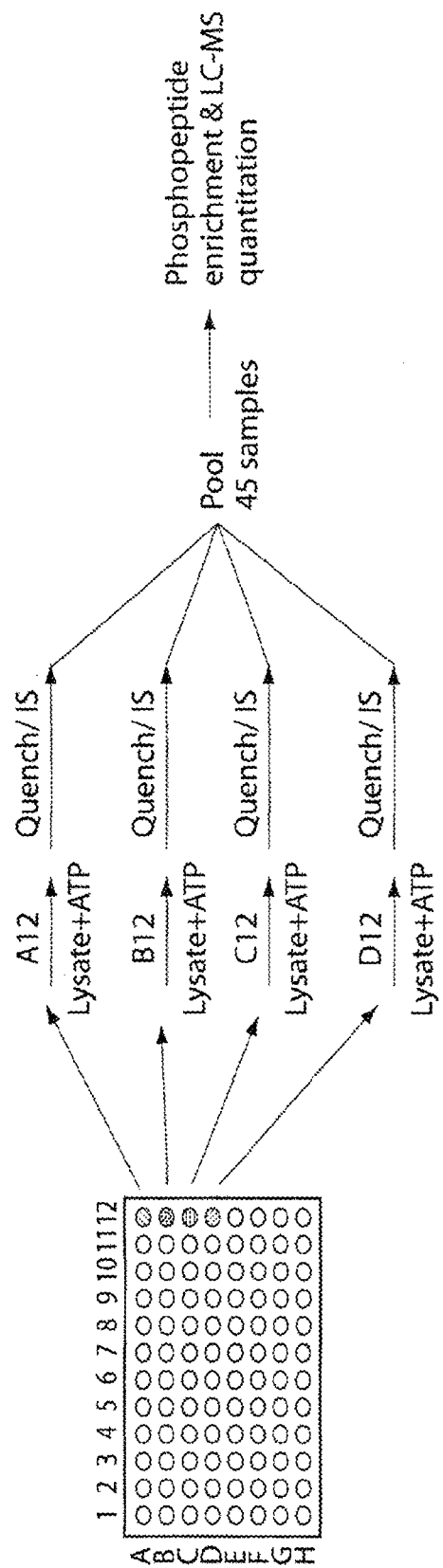
FIGS. 1A-1F are a set of drawings, photographs, an MS printout, a heat-map, a bar graph and a line graph showing a general scheme of the KAYAK strategy.
Figure 1B:
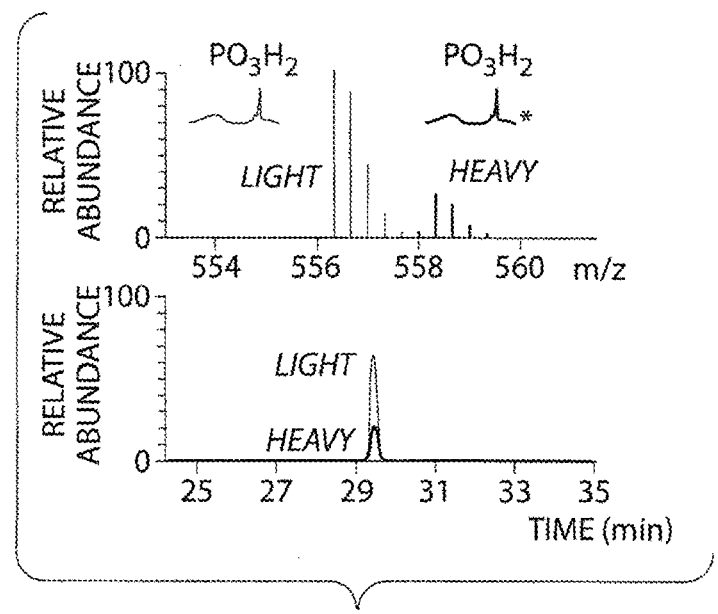
Figure 1C:
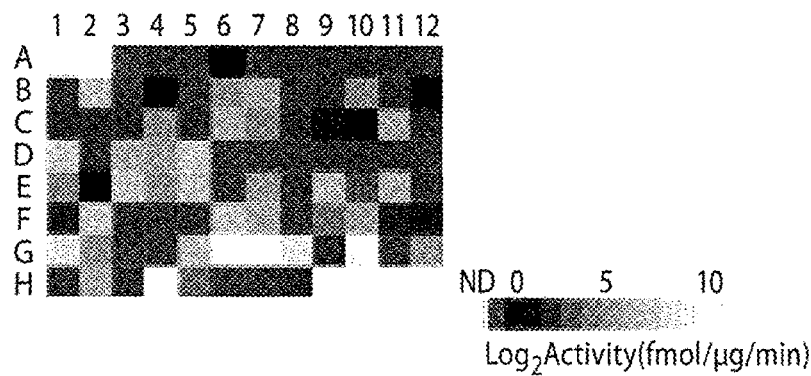

Many peptides derived from known phosphorylation sites contain additional Ser, Thr, and Tyr residues in their flanking sequences, sometimes leading to formation of additional phosphorylation position isomers. However, these site isomers were generally resolved by HPLC, and the phosphorylation site was subsequently confirmed by MS/MS analysis. Only two LC-MS runs were required to analyze the entire plate (FIG. 1A). Each phosphopeptide and identical-sequence reference peptide co-eluted, facilitating quantification by direct ratio to the reference peptide abundance (FIG. 1B). As a demonstration of their usefulness, more than half of the substrate peptides (49 out of 90) showed robust phosphorylation activities of at least 1 fmol/μg lysate/min (FIG. 1C) using serum-starved HEK293 lysate. The peptide showing the highest phosphorylation activity (position G10 in the 96 well plate, KKKRFsFKKSPFR, SEQ ID NO: 80) corresponded to myristoylated alanine-rich c-kinase substrate, residue 153-162. Lower case s/t/y in peptide sequences herein indicates that the phosphorylation site corresponded to conversion of only 18% of the substrate, showing that the reaction scheme resided within the linear portion of the kinase reaction. The activity measurements encompassed a range of more than 3 orders of magnitude. This wide dynamic range allows variations in kinase activities to be easily distinguishable, providing a tractable index of kinase mediated-cellular networks and pathways.

Example 9

Figure 1D:
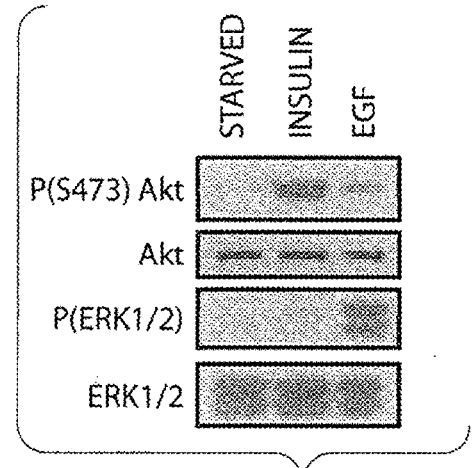
Figure 1E:
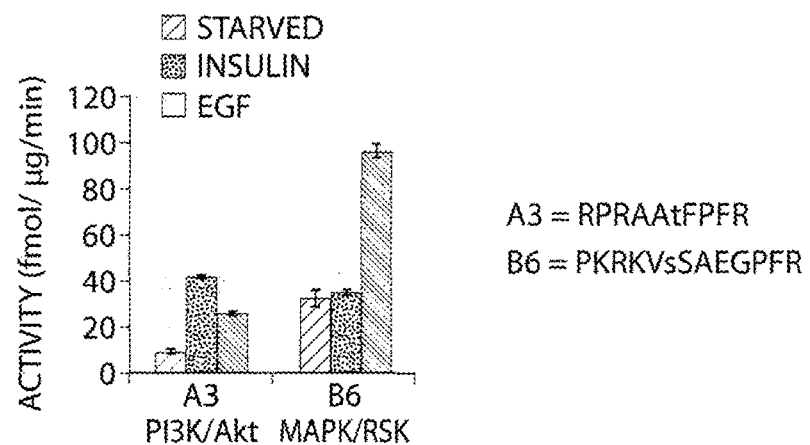
Figure 1F:
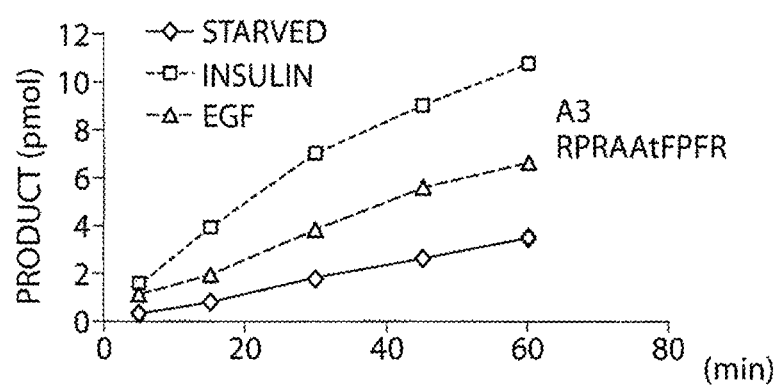

Profiling the Activities of Kinase Mediated-signaling Networks after Mitogen Stimulation The ability of the peptides to report specific changes in kinase activation after pathway stimulation was examined herein. Lysates from HEK293 cells were collected after insulin or EGF treatment and were compared to their activities in the serum-starved state using the KAYAK approach. Western blot analysis of lysates from cells in which the PI3K and MAPK pathways were activated, as indicated by elevated phospho-Akt and phospho-ERK1/2 levels, respectively, is shown in FIG. 1D. Phosphorylation of a derivative of a known Akt substrate peptide, Aktide (Cutillas et al. 2006 *Proc Natl Acad Sci USA* 103: 8959-8964; plate position A3, RPRAAtFPRF, SEQ ID NO: 1) was in good agreement with immunoblot results for Akt activation, showing a strong increase in phosphorylation after a 10-min insulin treatment (4.6-fold) and a weaker but substantial increase (2.9-fold) after EGF stimulation for 5 min (FIG. 1E). In contrast, peptide B6 reported increased phosphorylation activity after EGF (3-fold) but not insulin treatment of the cells. Peptide B6 corresponds to PKRKVsSAEGPFR, SEQ ID NO: 16, which was derived from sequences spanning Ser-6 of nonhistone chromosomal protein HMG-14. This site has been shown to be phosphorylated in vivo as a result of stimulation by MAPK downstream effectors RSK and MSK (Lim et al. 2004 *Mol Cell* 15: 573-584). Linearity of the product formation in a time-course experiment for the Akt peptide substrate, A3, was also observed (FIG. 1F). These assays were extremely sensitive; kinase activities toward several peptides were measured using as little as 50 ng of crude lysate per reaction (FIGS. 2A-2C). The average measured activities for triplicate analyses of all 90 peptides are shown in FIG. 3A for serum-starved, insulin- and EGF-stimulated lysates. Due to the large range of values in absolute activity measurements among peptides, log-transformed values were used.

Peptides were organized into several categories based on known kinase family sequence preferences including basophilic sites (e.g. Akt, Rsk, PKA and PKC), acidic (e.g. casein-kinase-II-like), proline-directed, or tyrosine-specific (Table1). Under serum-starved conditions, most peptides containing basophilic sites were still phosphorylated. While these same peptides were generally phosphorylated by serum-starved, insulin-treated and EGF-stimulated lysates, surprising differences were observed in the absolute activity levels for many peptides (Table 2, FIGS. 4A-4D). For example, a peptide derived from the tuberous sclerosis complex 2 gene product tuberin (E11, RKRLIsSVEDPFR, SEQ ID NO: 57, lower case s corresponds to Ser1798) showed upregulated phosphorylation after both insulin (1.7 fold) and EGF (2.3 fold) stimulation. Previously, this site was reported to be phosphorylated in vivo upon activation of either PI3K or MAPK pathways, with it being preferentially phosphorylated by the MAPK downstream kinase, RSK1 (Roux et al. 2004 *Proc Natl Acad Sci USA* 101: 13489-13494).

TABLE 2

Examples of substrate peptide specificity for different cell states.

| ID | Sequence | Protein (Phosphorylation site) | I* | E | G1/S ** | G2/M | Potential kinases | SEQ ID |
|---|---|---|---|---|---|---|---|---|
| A3 | RPRAAtFPFR | Aktide | ++ | + | | | Akt | 1 |
| A12 | PSTNSsPVLKPFR | separase (Ser1126) | | | | + | CDK | 10 |
| B4 | IPINGsPRTPPFR | retinoblastoma-associated protein (Ser249) | | + | | ++ | CDK | 14 |
| B5 | NQDPVsPSLVPFR | muscarinic acetylcholine receptor m2 (Ser232) | | | -- | - | MAPK | 15 |
| B6 | PKRKVsSAEGPFR | nonhistone chromosomal protein hmg-14 (Ser6) | | + | | - | RSK | 16 |
| B7 | VKRQSsTPSAPFR | phosphorylase b kinase regulatory subunit b (Ser 700) | | | -- | -- | PKA | 17 |
| B11 | LKLSPsPSSRPFR | lamin-b1 (Ser392) | | | + | ++ | CDK | 21 |

TABLE 2-continued

Examples of substrate peptide specificity for different cell states.

| ID | Sequence | Protein (Phosphorylation site) | I* | E | G1/S ** | G2/M | Potential kinases | SEQ ID |
|---|---|---|---|---|---|---|---|---|
| C2 | IPTGTtPQRKPFR | kinesin-like protein kif11 (Thr927) | | | | ++ | CDK | 24 |
| C6 | TKRSGsVYEPPFR | phosphorylase b kinase regulatory subunit b (Ser26) | | + | | − | RSK | 28 |
| C11 | NKRRGsVPILPFR | erythrocyte membrane protein band 4.2 (Ser247) | | + | | | RSK | 33 |
| D7 | NLLPLsPEEFPFR | STAT1 (Ser727) | | | −− | −− | MAPK | 41 |
| D10 | FKNIVtPRTPPFR | myelin basic protein (Thr229) | | | | ++ | CDK | 44 |
| E11 | RKRLIsSVEDPFR | tuberin (Ser1798) | | + | | − | Akt, RSK | 57 |
| F6 | RIRTQsFSLQPFR | nitric-oxide synthase, endothelial (Ser1176) | + | ++ | | | Akt, RSK | 64 |
| G5 | SKRRNsEFEIPER | tryptophan 5-hydroxylase 1 (Ser58) | | + | | | RSK | 75 |
| H5 | EYDRLyEEYTPER | PI3-kinase p85/p55 subunit (Tyr467/Tyr199) | | | | ++ | Src | 87 |

\* Peptides with changed phosphorylation in insulin (I) and EGF (E) stimulated conditions compared to starved HEK293 cells.
\*\* Peptides with changed phosphorylation during G1/S and G2/M phases compared to asynchronously growing HeLa cells. A change of more than +2 fold and −2 fold is indicated by "+" and "−", respectively. A change of more than +4 and −4 fold is indicated by "++" and "−−", respectively.

In contrast, phosphorylation of peptides B6, C6, C11 and G5 was observed to be increased only in EGF-stimulated but not insulin-treated conditions. Although the substrate library used herein contained several EGFR-derived peptides known to be phosphorylated after receptor activation in vivo, phosphorylation of these peptides in the EGF-stimulated (or any other) cell lysate was not observed, indicating that a correct context was critical for these sites to be phosphorylated. Nevertheless, the KAYAK method provided herein showed that at least seven peptides (Table 2, FIGS. 4A-4D) were capable of distinguishing quiescent from activated PI3K and MAPK signaling pathways.

Example 10

Profiling the Activities of Kinase-mediated Signaling Networks During Cell Cycle In order to examine target peptides with cell-cycle-dependent phosphorylation, kinase activities in asynchronously growing HeLa cells were profiled and the profiles were compared with those of cells synchronized in G1/S and G2/M phase using a double-thymidine block and nocodazole arrest, respectively (FIG. 3B).

Phosphorylation of many peptides containing Pro at the +1 position of S/T was now observed dramatically increased in G2/M phase (Table 2, FIGS. 4A-4D). Proline-directed kinases such as the cyclin-dependent kinases (CDK) are mitotically activated (Sullivan et al. 2007 *Nat Rev Mol Cell Biol* 8: 894-903). For example, peptide C2 (IPTGTtPQRK-PFR, derived from kinesin-like protein kif1, t corresponds to Thr-927, SEQ ID NO: 24) showed a 19-fold increase in phosphorylation during G2/M phase compared with asynchronously growing or G1/S cells. In a previous quantitative phosphoproteomics study the same site showed upregulated mitotic phosphorylation by 48 fold (Dephoure et al. 2008 *Proc Natl Acad Sci USA* 105: 10762-10767). This site has previously been shown to be phosphorylated by Cdc2 in vitro and is specifically phosphorylated during mitosis to regulate the association of kif1 with the spindle apparatus (Blangy et al. 1995 *Cell* 83: 1159-1169).

In another example, phosphorylation of peptide A12 (PSTNSsPVLKPFR, derived from separase, lower case s corresponds to Ser-1126; SEQ ID NO: 10) showed a ratio of 1.0:1.2:3.0 using the lysates of asynchronous growing cells. During G2/M phase, 91% of separase Ser-1126 is phosphorylated in vivo whereas the level of phosphorylation drops to 35% during S-phase, agreeing well with the phosphorylation level measured herein by the KAYAK peptide and method (Gerber et al. 2003 *Proc Natl Acad Sci USA* 100: 6940-6945).

Although tyrosine-specific phosphorylation was detected on several target peptides, their levels were here observed to remain largely unchanged or decreased after nocodazole arrest (compare FIG. 3B to immunoblotting analysis of the lysates using antibody specific for phosphotyrosines, FIG. 4C). An exception was rate of phosphorylation of peptide H5 (EYDRLyEEYTPFR; SEQ ID NO: 87) derived from phosphoinositide 3-kinase (PI3K) regulatory subunit p85α(Tyr-467)/p55γ (Tyr-199). Surprisingly, H5 showed a dramatic increase in phosphorylation (13 fold) in a lysate of nocodazole-arrested cells. Retention time comparisons and tandem MS experiments using both CID (collision-induced dissociation) and ETD (electron transfer dissociation) was used to confirm that the indicated Tyr rather than the C-terminal TP motif was phosphorylated (FIGS. 6A and 6B).

Several peptides including B5 (NQDPVsPSLVPFR, derived from muscarinic acetylcholine receptor m2, s corresponds to Ser-232; SEQ ID NO: 5) and D7 (NLLPL-sPEEFPFR, derived from signal transducer and activator of transcription 1, s corresponds to Ser-727; SEQ ID NO: 41) contained known MAPK phosphorylation motif of PxSP.

These peptides showed greatly decreased phosphorylation in G1/S and G2/M lysates compared with those in asynchronously growing cells, indicating they could be substrates of MAP kinases and not CDKs (FIG. 4D). However, phosphorylation of these peptides was below confidence threshold in EGF stimulated and starved HEK293 cells, preventing further assessment of their specificity in a different context.

Example 11

KAYAK Peptides as Reporters of Pathway Inhibition

The KAYAK method was applied to measure the effect of pharmacological inhibitors or siRNA-mediated knockdown of kinase pathways after mitogen stimulation (see FIGS. 5A-5D and 8 for data obtained by immunoblotting analysis of cell lysates). Insulin was observed to induce phosphorylation of peptide A3, an effect which was blocked by prior treatment of cells with the PI3K inhibitor Wortmannin. EGF stimulated cell lysates strongly phosphorylated peptides B6, C6, C11 and G5 and these effects were blocked by pretreating cells with the MEK-specific inhibitor U0126.

In contrast, phosphorylation levels of these peptides were not changed as a result of insulin stimulation. Peptides B6, C11, and G5 were observed to be specific targets of RSK by siRNA-mediated knockdown of RSK1/2 (see FIGS. 5A-5D) and purified kinase (FIGS. 10A and 10B). Lysates of PMA stimulated cells also were observed to strongly phosphorylate these peptides. PMA activates the MAPK pathway by activating the upstream kinase, PKC (Blenis et al. 1993 *Proc Natl Acad Sci USA* 90: 5889-5892). Because the observed increase in phosphorylation was reversed by prior treatment of cells with U0126, it was concluded that these peptides were not PKC substrates. Rather they were likely phosphorylated by kinases downstream of the MAPK pathway.

These four peptides were designed to contain basic residues at a location N-terminal to the phosphorylation site. Specifically, B6, C11 and G5 contain a serine residue with Arg or Lys at the -2 and -3 positions. This motif is preferentially phosphorylated by the ERK-activated kinase, RSK, compared with other AGC kinases including S6K and Akt (Leighton et al. 1995 *FEBS Lett* 375: 289-293). Six different RSK isoforms exist, and determination of phosphorylation by specific RSK by siRNA-mediated knockdown of RSK1/2 was investigated.

It was observed that basal phosphorylation of these peptides was not affected by knockdown and likely was the result of remaining RSK isoforms or other basophilic kinases (FIG. 5C). In contrast, EGF-induced phosphorylation was inhibited by RSK1/2 knockdown, demonstrating that activated RSK was involved in phosphorylating these peptides. It was thus determined that recombinant RSK1 could robustly phosphorylate peptides B6, C6, C11 and G5 in vitro. For example, using peptide C6 as substrate, it was found that 1 μg EGF-stimulated lysate contained the equivalent of approximately 0.6 ng recombinant RSK while the lysates of cells pretreated with U0126 then stimulated with EGF had an activity of 0.2 ng RSK/μg lysate (FIGS. 10A and 10B). As a control, peptide C6 was similarly tested, and it was observed that this peptide was not significantly phosphorylated by Akt. These data show that these peptides are specifically phosphorylated by activated RSK, and serve as markers for activation of the MAPK pathway.

To demonstrate the dynamic range of these peptides in measuring RSK activities, a series of examples used starved cells that were stimulated with EGF as a function of time. Prolonged EGF treatment leads to receptor internalization and desensitization of cells to the ligand. The results of the KAYAK method using peptide substrates B6, C6, and G5 demonstrated an excellent correlation with immunoblotting experiments for activated (phosphorylated) RSK and ERK (FIG. 5D).

Example 12

PI3 Kinase Regulatory Subunit p55 Shows Src-dependent Tyrosine Phosphorylation During Mitosis Cell-cycle-dependent phosphorylation was identified, including a novel mitosis-specific activity for Src family kinases toward PI 3-kinase regulatory subunit p55 (FIG. 7A). Immunoblotting methods were used to investigate the KAYAK results of the cell cycle lysates. A surprisingly large increase in mitotic phosphorylation of the peptide H5 (EY-DRLyEEYTPFR; SEQ ID NO: 87) was observed herein (FIG. 7A). This peptide contains a tyrosine residue which is conserved among various members of the PI3 kinase regulatory subunit (i.e. Tyr-197 of p55α, Tyr-199 of p55γ, Tyr-467 of p85α and Tyr-464 of p85β; FIG. 6A). Using a phospho-specific antibody specific for this site, the level of phosphorylation in vivo at this site on p55 also was observed to dramatically increase during G2/M phase (FIG. 7B). Increased phosphorylation was not detected at 85kDa. As the relative contribution of p55α and p55γ can not be differentiated, Tyr-199 of p55 is used herein to designate this phosphorylation site.

To examine the possibility that this mitotic phosphorylation was an artifact of nocodazole treatment, HeLa cells in early S-phase were synchronized using a double thymidine block. At various time points following removal of thymidine, progression through the cell cycle was followed by immunoblotting for phospho-p55 (Tyr-199) and a mitotic marker, phospho-retinoblastoma protein-1 at Ser-780 (FIG. 7C). These two phosphorylation events showed good correlation, indicating that phospho-PI3K regulatory subunit p55 (Tyr-199) increased during cell progression from G1/S through G2/M.

In order to identify the kinase that phosphorylates p55 (Tyr-199) lysates of serum-starved HEK293 cells were used for insulin, IGF and EGF stimulation. It was observed that phosphorylation of this tyrosine was not altered, showing independence of activation of insulin receptor, IGF receptor or EGFR (FIG. 7B). The activity of cell lysates with this peptide was not changed by any other perturbation used in these examples including serum starvation, insulin- or EGF-treatment. The soluble tyrosine kinase is transiently activated during mitosis (Zheng et al. 2001 *EMBO J* 20: 607-6049). Whether increased phospho-p55 was due to activated Src during mitosis was therefore examined. Indeed, Src activating phosphorylation (Tyr-416) was observed dramatically increase during G2/M (FIG. 7B), correlating well with elevated phospho-p55 (Tyr-199). In addition, in vitro kinase reactions of H5 peptide were observed to cause robust phosphorylation by Src but not EGFR (FIG. 7D).

To further investigate whether this is a Src-dependent site in vivo, asynchronously growing HEK293 cells were treated with the specific Src family kinase inhibitor, Su6656. The levels of both phospho-Src (Tyr-416) and phospho-p55 (Tyr-199) were observed to have diminished by the treatment (FIG. 7E). Further, MCF10A cells expressing v-Src:estrogen receptor (Reginato et al. 2005 *Mol Cell Biol* 25: 4591-4601) were treated with 1 μM 4-hydroxytamoxifen (4-HT) to activate v-Src as a function of time (FIG. 7F). Increased phosphorylation of p55 at Tyr199 was observed within 4 hrs and persisted whenever v-Src was activated. This result was determined not to have been an artifact of 4-HT treatment because MCF10A cells incubated with 1 µM 4-HT failed to show increased phosphorylation at this site (FIG. 7F). These results showed that p55 (Tyr-199) is a general Src-dependent phosphorylation site in vivo. Surprisingly, the protein level of p55γ was observed to have decreased after prolonged Src activation (FIGS. 7B and 7F), which was accompanied by an increase in p85 level (FIG. 7F). These findings demonstrate that even without prior knowledge of a kinase, its kinetics, or specificity, use of the methods herein to analyze in vitro peptide phosphorylation can lead to the discovery of both the responsible kinase in vivo and even the site's biological context.

Although poorly understood, PI 3-kinase activity was first discovered through its purification with v-src. Recent crystal structure of the PI3 kinasep110α/p85α complex shows that Tyr-467/p85α (correspondent of Tyr-199/p55γ) is localized within the interface between the inter-SH2 domain of p85α and the C2 domain of p110α. Specifically, Tyr-467 is 2.7 Ångstroms away from His450 of the catalytic subunit, within the distance for potential hydrogen bond formation. This interaction and even the interface will likely be disrupted by phosphorylation of Tyr-467. The monomeric form of the regulatory subunit is unstable in cells. This could potentially explain the fact that p55γ was degraded after prolonged Src activation. Many cancer mutations of p110α have also been mapped to this inter-domain region, including Asn-345Lys and Glu-453Gln. These mutations have been suggested to change the interaction between the two subunits which resulted in an elevated PI3 kinase activity. In addition, transfection of p110α harboring these mutations lead to both Akt activation and transformation of the cells. Therefore, it is also interesting to speculate whether phosphorylation of this tyrosine on the regulatory subunit would be a mechanism for Src to modulate the PI3 kinase activity. Additional studies to unravel the role of SFK in regulation of PI 3-kinase activity are ongoing.

Example 13

KAYAK Profiling of Kinome Activities in Cancer Cell Lines

In tumors, activating mutations are often found in core signaling pathways (McLendon et al. 2008 Nature 455: 1061-1068). To assess the ability of the KAYAK method to accurately identify differences in signaling pathway activation, the basal activity of seven asynchronously growing cancer cell lines was compared before and after being treated with an EGFR inhibitor, gefitinib (FIGS. 9A-9C). The cell lines were chosen to represent the highly heterogeneous nature of breast cancer.

A summary of the mutations in the PI3K and MAPK pathways for these cell lines is shown in FIG. 9A (Ferrer-Soler 2007 Int J Mol Med 20: 3-10). For example, MDA-MB231 is a cell line that is both ER and E-cadherin negative and is highly invasive and tumorigenic (Zheng et al. 2001 EMBO J 20: 6037-6049). This cell line contains the mutant form of K-Ras (G13D) and B-Raf (G464V; Thompson et al. 1992 J Cell Physiol 150: 534-544). Sum159 cell line also contains a mutation within the MAPK pathway (H-Ras$^{G12D}$; Hollestelle et al. 2007 Mol Cancer Res 5: 195-201). MCF7 cells, on the other hand, are both ER and E-cadherin positive and are less invasive. MCF7 cells also have lower EGFR expression level compared to MDA-MB231 cells (Campiglio et al. 2004 J Cell Physiol 198: 259-268). MCF10A cells, which are non-tumorigenic epithelial cells, and MCF10A cells overexpressing ErbB2, IGFR and RasV12, were also included.

The KAYAK results showed that there are significant differences in the basal kinase activities among these cell lines (FIG. 9B). For example, two breast cancer cell lines, MDA-MB231 and Sum159, displayed substantially higher MAPK activities (indicated by results using peptides B6, C6 and G5) compared with other cell lines, MCF7 and MCF10A (See Table 2). In addition, overexpression of ErbB2, IGFR and RasV12 in MCF10A cells resulted in significantly higher basal activities in the PI3K/Akt (indicated by peptide A3) and MAPK pathways. These results also showed good agreement with data obtained from Western blotting analysis (FIG. 9C).

The cell lines displayed diverse responses to gefitinib treatment. PI3K and MAPK activity in normal MCF10A cells and MCF10A/ErbB2, MCF10A/IGFR were strongly inhibited after gefitinib treatment. In contrast, MAPK activity of MCF10A cells overexpressing RasV12 showed gefitinib-resistance. Since Ras lies between EGFR and MAPK, this shows that mutant forms of Ras could lead to disengagement of MAPK from EGFR. However, whether a Ras mutation can convey resistance of MAPK activity to EGFR inhibition is cellular context-dependant.

Although both MDA-MB231 and Sum159 cells contain a Ras mutation, MAPK activity in MDA-MB231 cells was completely refractory to EGFR inhibition. In addition, overexpression of ErbB2, IGFR and H-Ras$^{G12V}$ in MCF10A cells led to higher basal activities in both the PI3K/Akt and MAPK pathways. Growth of MDA-MB231 cells is resistant to gefitinib treatment, with an IC$_{50}$ of 18 µM (gefitinib; Giocanti et al. 2004 Br J Cancer 91: 195-201). Growth of HeLa cells is resistant to gefitinib (IC$_{50=8}$ µM) and activation of MAPK in these cells was found not to be affected by 1 µM gefitinib treatment. MCF10A cells and MCF10A/ErbB2, MCF10A/IGFR were strongly inhibited after 1 µM gefitinib treatment. MAPK activity in Sum159 cells showed some sensitivity towards gefitinib treatment. Another breast cancer cell line, MCF7, with high IC$_{50}$ (21 µM; Ferrer-Soler et al. 2007 Int J Mol Med 20:3-10) showed decreased activity in both PI3K and MAPK pathway. In contrast, MCF10A cells are sensitive to gefitinib, with a cell growth IC$_{50}$ of 0.13 µM (Normanno et al. 2006 J Cell Physiol 207: 420-427).

A differential response of Src activity toward gefitinib treatment was also observed as reported by H5 peptide and corroborated by Western blot. Src was inhibited in MCF7, Sum 159, MCF10A/IGFR, and MCF10A/H-Ras$^{G12V}$ cells, whereas Src activity in HeLa and MCF10A cells was resistant to gefitinib inhibition. Overall, phosphorylation activity measures data obtained herein using KAYAK approach correlated with the activating mutations within the pathways in diverse cell lines.

Example 14

KAYAK Profiling Kinome Activities of Renal Cell Carcinoma Tissues of Cancer Patients The tumor and normal kidney samples from five cancer patients (RCC, renal cell carcinoma) were obtained after radical nephrectomy and were examined. PI3K and MAPK activities showed consistent elevation in cancerous compared to normal tissues (FIG. 11B).

Immunohistochemical data further showed that pAKT and pERK1/2 were higher in the cancerous parts of the tissues (FIG. 11C). However, the Src activity indicator, phospho-p55 (Tyr-199) level, varied among these tissue samples. Phospho-p55 level was observed to be heterogeneous among the samples, being higher in cancerous tissues and endothelial region of the normal tissues. The specificity of these peptides was confirmed by pharmacological inhibition and siRNA-directed knockdown experiments.

Example 15

Development and Validation of a Single-reaction, Solution-phase 90-substrate Kinase Assay A scheme for obtaining 90 simultaneous activity measurements is illustrated in FIG. 13. Substrate peptides were chosen to include a number of core signaling pathways as well as sites identified by large scale phosphoproteomics studies (Beausoleil et al. 2004 *Proc Natl Acad Sci USA* 10: 12130-12135; Villen et al. 2007 *Proc Natl Acad Sci USA* 104: 1488-1493) with no associated kinase (Table 1). Peptides were synthesized and purified individually as 10-15 mers. Peptides included five residues upstream of the phospho-acceptor site, four downstream residues, and a C-terminal tripeptide of Pro-Phe-Arg to facilitate quantification and stable isotope incorporation (Yu et al. 2009 *Proc Natl Acad Sci USA* 106: 11606-11611). In vitro kinase assays were performed in a single 50 μl reaction containing the kinase source (for example a cell lysate in a kinase assay buffer), ATP, and the mixture of 90 KAYAK peptides (5 μM each). Substrate phosphorylation typically proceeded for 45 minutes following by quenching with acid, and 90 additional stable-isotope-labeled internal standard phosphopeptides were added. Phosphorylated peptides were enriched via immobilized metal-ion affinity chromatography (IMAC) and then analyzed by LC-MS. Each KAYAK phosphopeptide perfectly co-eluted with its heavier internal standard peptide of identical sequence. Because a minimum of 180 different peptides of similar m/z must be resolved, high resolution mass spectra were collected. In addition, the sequence and site localization of each phosphopeptide was verified by tandem mass spectrometry (MS/MS) fragmentation if necessary. Since a known amount of each heavy phosphopeptide was added, the ratio of light to heavy phosphopeptide provided a measure of absolute amount of each product formed during the reaction. To facilitate analyses, the limit of detection for each phosphorylated substrate peptide was conservatively set at 1% of the internal standard response although often manual integration of response differences up to 4 orders of magnitude was possible.

A major difference from prior examples herein (Yu et al. 2009 *Proc Natl Acad Sci USA* 106:11606-11611, incorporated herein by reference in its entirety) is that substrate peptides were reacted as a mixture, which gave remarkably higher-throughput and 90-fold less sample consumption.

To reduce cross-phosphorylation of peptides by different kinases, the concentration of each peptide was reduced from 100 μM to 5 μM. For instance, peptides were reacted at 20-fold reduced concentrations (5 μM), and competition effects improved kinase monospecificity (FIG. 15C). For example, six of the 90 peptides were found to be excellent RSK substrates at 100 μM with no competition. However, when reacted together at 5 μM, a single highly specific RSK substrate remained, peptide E11 derived from a known RSK substrate. Another example is peptide F6, derived from a known Akt target site on nitric oxide synthase. At 100 μM and individually reacted, both RSK and Akt demonstrated strong phosphorylation. With competition effects and reduced substrate concentrations, this peptide is an excellent Akt substrate.

To assess candidate kinases for each peptide, the 90 peptides were profiled using commercially available 18 purified kinases (FIGS. 14A and 14B). Although kinases are known to show more promiscuity in their purified forms (Manning et al. 2007 *Cell* 129: 1261-1274), these data allow for a first look at potential kinases and some assessment of the degree of monospecificity for each peptide.

Assay performance was benchmarked using lysate from a transformed human epithelial cell line (HEK293) after insulin stimulation (FIG. 15A). The sensitivity of each peptide was assessed using lysates amounts varying from 1 ng to 20 μg. Phosphorylation of at least half of the library was measured with site-specific phosphorylation of greater than 50 fmol using 10 or 20 μg of lysate. Eight peptides were phosphorylated from the equivalent of about 20-cell sensitivity (10 ng lysate), and two exceptional peptides were phosphorylated using only one ng lysate (FIG. 16B). Surprisingly, the vast majority of peptides (88%, 43 peptides among 49 peptides detected in more than one concentration) demonstrated a linear response to lysate amount (r>0.9), suggesting that lysate amount (or sample dilution) is not a factor in kinase activity measurements (FIG. 15B and FIG. 16A). The assay showed exceptional reproducibility (FIGS. 18 and 20, and Example 16).

The KAYAK strategy described here was compared to performing 90 individual kinase reactions in a plate format under identical conditions. Lysates from cells before and after insulin stimulation were used and excellent agreement between the same-reaction or individual kinase reactions was found (FIG. 15C and FIG. 20). Three peptides (A3, E11 and F6) showed reproducibly increased phosphorylation in response to insulin stimulation. Performing the assay in a single reaction resulted in more robust changes for each of these three phosphorylated peptides compared to the individual reaction method, likely because competitive effects widen the gap between the best and other substrates in the kinase reaction (Ubersax et al. 2007 *Nat Rev Mol Cell Biol* 8: 530-541).

Example 16

Validation of a Single-reaction, Solution-phase 90-substrate Kinase Assay

A few peptides in FIGS. 15A-15C including peptide C11 (derived from a known PKA target) demonstrated a linear response only at the lower end of lysate amounts. Because these peptides appear all to be PKA substrates (based on phosphorylation with purified kinases shown in FIGS. 14A and 14B), the phenomenon was attributed to unmasking of the active kinase when association of PKA with inhibitory regulatory domain of PKA or A-kinase anchoring protein was removed by dilution.

To assess assay reproducibility, duplicate KAYAK profiling analyses on lysates from five different dishes of HEK293 cells were performed herein (FIG. 18). Using 55 peptides with measureable phosphorylation, the average coefficient of variation of 10 measurements was outstanding at 11%. Moreover, for peptides where product formation was close to the detection limit, the assay still demonstrated excellent reproducibility and precision.

Example 17

Insulin and EGF Stimulation of Cells Results in Distinct Kinase Activity Profiles as Measured in a Single-reaction Assay To distinguish basal cellular kinase activity from stimulated states, kinase activities from serum starved HeLa and from HEK293 cells treated with insulin, epidermal growth factor (EGF) or phorbol 12-myristate 13-acetate (PMA) were compared using a single-reaction 90-substrate assay (FIGS. 17A-17C). After hierarchical clustering of the normalized activities, peptides preferentially phosphorylated by a particular kinase in an in vitro assay using purified enzyme (FIGS. 14A and 14B) clustered together. Compared to HeLa cells, HEK293 cells were 2-fold more responsive to insulin stimulation as measured by the A3 peptide (FIG. 17B), which is a highly selective substrate of Akt (Alessi et al. 1996 *FEBS Lett* 399: 333-338). Similalar results were obtained with Western blotting data probed with antibody specific for phospho-Akt (FIG. 17C). In addition, the E11 peptide, which has a 90 kDa ribosomal S6 kinase (RSK) phosphorylation motif (Anjum et al. 2008 *Nat Rev Mol Cell Biol.* 9: 747-758) and is preferably phosphorylated by purified RSK1 enzyme (FIGS. 14A and 14B) displayed increased phosphorylation after activation of Ras/MAPK pathway by EGF or PMA treatment (FIG. 17B) consistent with the Western blotting data (FIG. 17C).

Since the KAYAK methodology measures the absolute amount of phosphorylated peptides formed by the kinase reaction, the observed difference in basal kinase activities between HEK293 and HeLa cells with respect to the E11 peptide may reflect differences in kinase activity states as seen on Western blots. Overall, while basal levels and fold-changes in kinase activities were not necessarily identical in these two cell lines, the direction of change for each peptide in response to each stimulus was consistent (FIGS. 17A-17C), highlighting conserved signaling pathways.

Example 18

KAYAK Profiling of a Panel of Human Cell Lines Reveals Major Differences in Basal Kinase Activity States in a Single-reaction Assay Baseline profiling of kinase activation state can lead to the identification of aberrantly activated pathways and cellular processes. With a goal of identifying unique signatures in each cell line, kinase activities from nine human cell lines grown under standard recommended conditions were profiled in a single-reaction, solution-phase 90 substrate kinase assay (FIGS. 19A and 19B). Peptides with similar activity profiles across the cell lines were grouped by hierarchical clustering (FIG. 19A). Surprising differences in core pathway activation states were identified. The MCF7 breast cancer cell line, for example, demonstrated uniquely high levels of PKA activity, consistent with the previous report which showed a comparison between normal (MCF10A) and the tumor (MCF7) cell lines (Sigoillot et al. 2004 *Int J Cancer* 109: 491-498). The U-87 MG glioblastoma cell line had between 3- and 20-fold higher basal phosphorylation of the Akt-selective peptide, A3, compared to any other cell line in the panel. U-87 MG is known to have a frameshift mutation in PTEN (Chou et al. 2005 *J Biol Chem* 280: 15356-15361) which leads to elevated phosphatidylinositol 3,4,5-triphosphate ($PIP_3$) levels and hyperactivation of Akt. The PTEN deficient Jurkat T lymphocyte cell line (Astoul et al. 2001 *Trends Immunol* 22: 490-496) also showed high A3 phosphorylation, which was confirmed by Western blotting (FIG. 19C). Moreover, Jurkat cells displayed upregulated Tyr kinase and PKC activities, which reflect high basal activities of Lck/Abl and protein kinase C (PKC)/extracellular signal-regulated kinase (ERK) pathways (Roose et al. 2003 *P LoS Bio* 1: E53).

Tyrosine-phosphorylated peptides clustered into at least three different groups (FIGS. 19A and 19B), demonstrating the detection of multiple activated tyrosine kinase pathways. In these nine cell lines, KAYAK profiling clearly demonstrated phosphorylation events specific to each cell line. Although only a general biological association for each cluster is known, the unique kinase activity signature for individual cell lines reflects key differences in either pathway activation and/or regulation.

Example 19

Profiling Elevated Activities of Akt and RSK in Human Renal Carcinoma Assessed in a Single-reaction Assay The KAYAK single-reaction assay was used to analyze clinical samples and tissue from renal carcinoma patients. Renal cell carcinoma and normal kidney specimens were obtained from an Institutional Review Board approved genitourinary oncology tumor bank at Massachusetts General Hospital, samples were prepared as described in Example 14 and subjected to KAYAK profiling using 90 peptides (FIG. 24A). As expected, Akt and RSK/ERK pathway activities were elevated in the tumor samples compared to the adjacent normal tissue although the absolute activity levels differed from patient to patient (FIG. 24B). These data agreed with Western blot and immunohistochemistry results (data not shown). Moreover, these findings raise the possibility of using kinase activities as signatures or biomarkers in clinical samples that are casually linked to oncogenic signaling pathways. Ultimately, such an assay could match individual patients with the appropriate cocktail of kinase-directed therapies.

Example 20

The Combination of Protein and KAYAK Profiling of Fractionated Lysates in a Single-reaction Assay Can Associate Kinases and Substrates It is often highly desirable to identify a kinase responsible for a particular phosphorylation event. While purified forms of known kinases provide a starting point (FIGS. 14A and 14B), testing the approximately 500 kinases in human genome (Manning et al. 2002 *Science* 298: 1912-1934) has not theretofore been practical, failing to capture the cellular context of these enzymes.

To address this issue, a novel biochemical strategy was developed to identify the kinase responsible for the phosphorylation of a peptide substrate using KAYAK profiling in a single-reaction, solution-phase 90-substrate assay. A lysate of interest is first fractionated by column chromatography at the protein level (FIG. 25), and each fraction is subjected to KAYAK profiling to determine the activity profile. In parallel, an aliquot of each fraction is trypsin digested and analyzed by LC-MS/MS techniques to identify and assess the abundance of thousands of proteins, providing a protein profile for each fraction. A strategy of correlating the activity and kinase abundance profiles as a function of active fractions was set to identify the responsible kinase.

The methodology was validated by identifying a mitotic kinase activity from HeLa cells. A heat map of the kinase activities from three different HeLa cell lysates: asynchronous, G1/S-phase arrested, or G2/M-phase arrested is shown in FIG. 22A. Hierarchical clustering revealed core pathway differences. Seven peptides sharing a common motif of [S/T]-Pro and clear upregulation by G2/M arrest (FIGS. 22A, 22B, and 26A) were selected for correlation profiling experiments to identify the responsible kinase. Lysate from nocodazole-arrested HeLa cells was separated by high resolution anion exchange chromatography, and the flow-through and 36 fractions were collected (FIG. 22C). The activity profile for each peptide was assessed (FIG. 22D). It was observed that all seven peptides demonstrated the identical pattern of normalized phosphorylation rates, indicating that a single kinase was responsible for their phosphorylation. Trypsin digestion and shotgun sequencing by LC-MS/MS of each fraction identified 3,928 proteins including 116 kinases (FIG. 26C). The correlation profile for each protein and each kinase was assessed based on normalized spectral counting. Calculating the Pearson correlation coefficient between kinase activity and protein amount in the active fractions, it was observed that Cdc2 was the best ranked kinase and 8th overall among 3,928 proteins as seen in FIGS. 22E and 27A. Protein quantitation of Cdc2 showed two major peaks and the second eluting peak of Cdc2 correlated with the kinase activity profile (FIG. 22E). This second peak also showed an excellent correlation profile with Cyclin B1, which ranked fifth overall among all proteins and is required for Cdc2 activity (Nurse 1990 *Nature* 344: 503-508; Pan et al. 1993 *J Biol Chem* 268: 20443-20451).

Western blotting confirmed the mass spectrometry-based results (FIG. 27B). Moreover, purified Cdc2/Cyclin B1 complex phosphorylated all 7 peptides along with 4 other up-regulated peptides (FIG. 22F). These data identified Cdc2 as the most likely kinase and Cyclin B1 as a complex member for the phosphorylation of these seven peptides including one peptide (A6) which was predicted to be an ERK and p38 MAPK target using Scansite (Obenauer et al. 2003 *Nucleic Acids Res* 31: 3635-3641).

Example 21

Effect of Commonly used Kinase Inhibitors on Signaling Pathways Assessed in a Single-reaction Assay It is difficult to predict the cellular effects of a kinase inhibitor despite design efforts to achieve selective inhibition of a single target (Sebolt-Leopold et al. 2006 *Nature* 441: 457-462; Bain et al. 2007 *Biochem J* 408: 297-315). To evaluate the activity profile of commonly used kinase inhibitors, HEK293 cells were treated with various reference compounds followed by insulin stimulation and KAYAK analysis using a single-reaction, solution-phase 90-substrate assay (FIGS. 23A-23C).

Consistent with previous observations (FIG. 15C), insulin stimulation upregulated the phosphorylation of only three peptides (FIG. 20). Wortmannin, a PI3K inhibitor, and Akt inhibitor VIII decreased the phosphorylation rate of the A3 peptide (FIG. 23B) in accordance with Western blotting (FIG. 23C). Peptide E11 showed unexpected results. This peptide is derived from a reported RSK substrate, but its phosphorylation rate increased by more than 2 fold with insulin. These increases were blocked by Wortmannin, confirming the PI3K pathway, but were also blocked by the MEK inhibitor, suggesting that the results seen are indeed due to RSK activation through the MAP kinase pathway. It appears that in HEK293 cells, insulin stimulation can also activate to some extent the MAPK pathway. The use of a panel of inhibitors allowed the conclusion that E11 phosphorylation after insulin stimulation is due to direct phosphorylation by MAPK/RSK and not by PI3K/Akt. Surprisingly, the p38 MAPK inhibitor, SB203580, lead to a paradoxical upregulation of the RSK/ERK pathway peptide E11 (FIG. 23B). This result indicates possible off-target effects of the compound and/or compensatory mechanism within the cell. Indeed, compensatory feedback loops induced by pharmacological agents that target the MAPK and PI3K pathway is a recurring theme and has been well-documented for inhibitors of mammalian target of rapamycin (mTOR) and RSK (Carracedo et al. 2008 *J Clin Invest* 118: 3065-3074; Sapkota et al. 2007 *Biochem J* 401: 29-38).

Example 22

KAYAK Approach Improves the Kinase Specificity Problem Using Peptides as Substrates Kinase specificity presents a challenge to peptide-based measurements of kinase activities. The lack of monospecificity at best complicates the interpretation of activity measurements, and at worst it may entirely mask changes in signaling pathways. The KAYAK approach described here addresses the kinase specificity problem in three important ways. First, the assay provides site-specific measurements by using site-specific internal standards. In this way, kinases recognizing and phosphorylating alternative residues in a peptide do not affect the measurement (Yu et al. 2009 *Proc Natl Acad Sci USA* 106: 11606-11611, incorporated herein by reference in its entirety). Second, the use of low peptide concentrations (5 μM) ensures that only high affinity substrates are phosphorylated. Third, competition effects are predicted to have an overall beneficial effect on kinase assays, adding specificity where better substrates are preferentially phosphorylated (Ubersax et al. 2007 *Nat Rev Mol Cell Biol* 8: 530-541). Indeed, larger measured insulin-dependent changes with competition were observed (FIG. 15C). Each advance results in a reduction of off-target effects, increasing pathway confidence and the degree of monospecificity for kinase-substrate pairs. Even without considering known kinase specificities, the signature pattern of phosphorylation rates could distinguish differences in kinase inhibitor potency and cell-line-specific effects.

Example 23

Advantages of the KAYAK Strategy

Compared to other strategies, the KAYAK strategy has several advantages. Measuring the activity of a kinase characterizes its activation status by directly monitoring kinase enzymatic activities, and an activity-indicating antibody is not necessary. Traditional methods, e.g. Western blot and SH2 domain binding assay, are indirect, and do not take into the account other modifications and protein-protein interactions that might affect the enzyme activity. Although commonly used, phosphorylation-activity relationships are known to be far from ideal. Moreover, activation-state phospho-antibodies are not available for many kinases.

The KAYAK measures the intrinsic activity of multiple kinases reflecting the complex cellular context. High-throughput kinase assays using large kinase panels (Goldstein et al. 2008 *Nat Rev Drug Discov* 7: 391-397) use truncated or recombinant purified enzymes, which may not reflect the actual conformational or kinase activity state as they appear in cells.

The KAYAK has high sensitivity owing to the signal amplifying nature of enzymatic reactions. Two KAYAK peptides showed detectable phosphorylation from as little as 1 ng of cell lysate which corresponds to near single cell levels (FIG. 15A and FIGS. 16A and 16B). This sensitivity allows for low sample consumption. Practically 10-20 µg of cell lysate is sufficient to have reliable signals for about 50 simultaneously peptide reactions (FIG. 15A).

The KAYAK measures site-specific phosphorylation rates. Commonly phosphorylation sites have additional phosphorylatable residues nearby (Schwartz et al. 2005 *Nat Biotechnol* 23: 1391-1398). Since the internal standard peptides are synthesized with phosphorylation at known positions, the co-elution of lysate-phosphorylated peptides and the standard phosphopeptides in conjunction with fragmentation sequencing ensures that site-specific phosphorylation is measured. When combining with MS/MS experiments, the KAYAK method accurately determines the kinase activity towards a specific site. This is not accomplished by any alternative methods, over which the KAYAK method represents a significant improvement. This is due to the site-specific nature of the detection, determination of absolute activity values (i.e., fmol/µg/min), and the ability to measure many different activities from the same lysate. One meritorious approach similarly uses peptide substrates which are spotted on a glass slide and incubated with cell lysates and $^{33}$P-labeled ATP. Phosphorylation of target peptides in these arrays has been used to profile LPS-stimulated monocytes and identified Lck and Fyn kinases as early targets of glucocorticoids (Diks et al. 2004 *J Biol Chem* 279: 49206-49213; Lowenberg et al.2005 *Blood* 106: 1703-1710). However, these arrays, while high-throughput, only measure site-specific phosphorylation when a single acceptor site is present in the target peptide and may not accurately report activities due to solid-phase immobilization of substrates and radioactivity effects.

The KAYAK is quantitative with exceptional reproducibility (FIGS. 18 and 20). Internal standards of heavy peptides, which are added upon quenching the kinase reaction, cancel any downstream sample manipulate and measurement variations and provide the basis for absolute activity measurements (i.e., fmol phosphorylation/µg lysate/minute). Western blotting cannot offer a similar level of quantitative quality.

The assay and protocol can be applied across a wide range of cellular settings including: recombinant purified enzymes (FIGS. 14A and 14B), cell line lysates (FIGS. 17A-17C and 19A-19C) and clinical human tissues (FIGS. 24A and 24B).

This KAYAK is radio-isotope free method.

KAYAK provides a sensitivity level of a few cells. The renal carcinoma tissue results have exceptional promise in the field of clinical proteomics. Samples in this discipline are often from biopsies, laser-capture-microdissection, or cell sorting experiments. The number of cells available in these sample types often falls far short of what has been used for direct profiling of phosphorylation events ($10^7$-$10^9$ cells). Kinase activity measurements overcome sensitivity pitfalls through a highly amplified process where zeptomole amounts of enzyme easily produce mass-spectrometry-amenable levels (>1 fmol). For this reason, activity measurements have been described as analogous to polymerase chain reaction (PCR) for protein.

Sample workup is minimal. KAYAK can be performed using crude cell lysates without first immunoprecipitating the target kinase, which allows a rapid and reproducible quantitation.

When characterizing the kinase pathways in a targeted fashion, KAYAK offers an exceptional throughput. KAYAK can be performed simultaneously to characterize tens of kinase pathways within potentially hundreds of samples, whereas only a few samples can be analyzed at a time by other quantitative proteomics methods (SILAC, iTRAQ, etc). KAYAK can be used casually to deal with a large number of samples. For example, it does not seem to be practical to use peptide array technology for monitoring 37 fractions to identify a responsible kinase.

Peptide optimization can identify a "golden" set of specific and sensitive substrates tuned to the most appropriate substrate assay concentration. However, for some applications including biomarker identification, current kinase activity signatures provide sufficient information to match disease and appropriate pathway-directed therapy. Such applications are especially relevant to the treatment of cancer.

What is claimed is:

1. A kit for a kinase activity assay for kinome profiling (KAYAK), the kit comprising:
   (i) at least two oligopeptides substrates said at least two oligopeptide substrates each comprising a kinase substrate selected from SEQ ID NO: 1-90 and an end terminal modification for isolation and for mass spectrometry;
   (ii) at least two oligopeptide internal standards, the at least two oligopeptide internal standards each comprising an oligopeptide substrate of (i) and an end terminal amino acid labeled with a heavy isotope.

2. The kit according to claim 1, wherein the end terminal modification comprises at least one hydrophobic amino acid located at the carboxy terminal end.

3. The kit according to claim 1, further comprising instructions for use with biological samples.

4. The kit according to claim 1, comprising the at least two oligopeptides substrates provided in a single container.

5. The kit according to claim 1, comprising the at least two oligopeptides substrates in separate containers.

6. The kit according to claim 5, wherein the at least two oligopeptides substrates in the separate containers are in a 96-well format.

* * * * *

UNITED STATES PATENT AND TRADEMARK OFFICE
CERTIFICATE OF CORRECTION

PATENT NO. : 10,407,712 B2  
APPLICATION NO. : 15/784734  
DATED : September 10, 2019  
INVENTOR(S) : Gygi et al.

Page 1 of 1

It is certified that error appears in the above-identified patent and that said Letters Patent is hereby corrected as shown below:

In the Specification

Delete the paragraph beginning at Column 1, Line number 19 and replace it with the following paragraph:
This invention was made with government support under HG003456 awarded by the National Institutes of Health. The government has certain rights in the invention.

Signed and Sealed this  
Twenty-eighth Day of January, 2025

Coke Morgan Stewart  
*Acting Director of the United States Patent and Trademark Office*

SEQUENCE LISTING

```
<160> NUMBER OF SEQ ID NOS: 96

<210> SEQ ID NO 1
<211> LENGTH: 10
<212> TYPE: PRT
<213> ORGANISM: Artificial Sequence
<220> FEATURE:
<223> OTHER INFORMATION: The sequence was designed and synthesized

<400> SEQUENCE: 1

Arg Pro Arg Ala Ala Thr Phe Pro Phe Arg
1               5                   10

<210> SEQ ID NO 2
<211> LENGTH: 13
<212> TYPE: PRT
<213> ORGANISM: Artificial Sequence
<220> FEATURE:
```

```
<223> OTHER INFORMATION: The sequence was designed and synthesized

<400> SEQUENCE: 2

Gly Pro Leu Ala Gly Ser Pro Val Ile Ala Pro Phe Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 3

Leu Pro Gly Gly Ser Thr Pro Val Ser Ser Pro Phe Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 4

Arg Pro Gly Pro Gln Ser Pro Gly Ser Pro Pro Phe Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 5

Val Gly Gly Ala Gly Tyr Lys Pro Gln Leu Pro Phe Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 6

Gly Pro Gly Val Asn Tyr Ser Gly Leu Gln Pro Phe Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 7

Glu Pro Leu Thr Pro Ser Gly Glu Ala Pro Pro Phe Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: The sequence was designed and synthesized
```

<400> SEQUENCE: 8

Thr Pro Pro Ser Ala Tyr Gly Ser Val Lys Pro Phe Arg
1               5                   10

<210> SEQ ID NO 9
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 9

Ala Pro Lys Lys Gly Ser Lys Lys Ala Val Pro Phe Arg
1               5                   10

<210> SEQ ID NO 10
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 10

Pro Ser Thr Asn Ser Ser Pro Val Leu Lys Pro Phe Arg
1               5                   10

<210> SEQ ID NO 11
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 11

Gly Ser Ala Ala Pro Tyr Leu Lys Thr Lys Pro Phe Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: The sequence was designed and synthesized

<400> SEQUENCE: 12

Lys Lys Ala Ser Phe Lys Ala Lys Lys Pro Phe Arg
1               5                   10

<210> SEQ ID NO 13
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 13

Ala Lys Thr Arg Ser Ser Arg Ala Gly Leu Pro Phe Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: The sequence was designed and synthesized

```
<400> SEQUENCE: 14

Ile Pro Ile Asn Gly Ser Pro Arg Thr Pro Pro Phe Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 15

Asn Gln Asp Pro Val Ser Pro Ser Leu Val Pro Phe Arg
1               5                   10

<210> SEQ ID NO 16
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 16

Pro Lys Arg Lys Val Ser Ser Ala Glu Gly Pro Phe Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 17

Val Lys Arg Gln Ser Ser Thr Pro Ser Ala Pro Phe Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 18

Thr Pro Ser Leu Pro Thr Pro Pro Thr Arg Pro Phe Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 19

Arg Thr Pro Lys Asp Ser Pro Gly Ile Pro Pro Phe Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 20
```

Thr Lys Arg Asn Ser Ser Pro Pro Ser Pro Phe Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 21

Leu Lys Leu Ser Pro Ser Pro Ser Ser Arg Pro Phe Arg
1               5                   10

<210> SEQ ID NO 22
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 22

Val Pro Pro Ser Pro Ser Leu Ser Arg His Pro Phe Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 23

Pro Lys Gly Thr Gly Tyr Ile Lys Thr Glu Pro Phe Arg
1               5                   10

<210> SEQ ID NO 24
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 24

Ile Pro Thr Gly Thr Thr Pro Gln Arg Lys Pro Phe Arg
1               5                   10

<210> SEQ ID NO 25
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 25

Gly Leu Pro Lys Ser Tyr Leu Pro Gln Thr Pro Phe Arg
1               5                   10

<210> SEQ ID NO 26
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 26

Asp Ser Ala Arg Val Tyr Glu Asn Val Gly Pro Phe Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 27

Leu Leu Lys Leu Ala Ser Pro Glu Leu Glu Pro Phe Arg
1               5                   10

<210> SEQ ID NO 28
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 28

Thr Lys Arg Ser Gly Ser Val Tyr Glu Pro Pro Phe Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 29

Leu Lys Lys Leu Gly Ser Lys Lys Pro Gln Pro Phe Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: The sequence was designed and synthesized

<400> SEQUENCE: 30

Gly Lys Ala Lys Val Thr Gly Arg Trp Lys Pro Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 31

Lys Lys Ser Lys Ile Ser Ala Ser Arg Lys Pro Phe Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 32

Ala Glu Asn Ala Glu Tyr Leu Arg Val Ala Pro Phe Arg

```
1               5                   10
```

<210> SEQ ID NO 33
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 33

```
Asn Lys Arg Arg Gly Ser Val Pro Ile Leu Pro Phe Arg
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 34

```
His Leu Leu Ala Pro Ser Glu Glu Asp His Pro Phe Arg
1               5                   10
```

<210> SEQ ID NO 35
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 35

```
Arg Lys Thr Thr Ala Ser Thr Arg Lys Val Pro Phe Arg
1               5                   10
```

<210> SEQ ID NO 36
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 36

```
Ala Pro Pro Arg Arg Ser Ser Ile Arg Asn Pro Phe Arg
1               5                   10
```

<210> SEQ ID NO 37
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 37

```
Lys Leu Ser Gly Phe Ser Phe Lys Lys Asn Pro Phe Arg
1               5                   10
```

<210> SEQ ID NO 38
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 38

```
Leu Lys Ile Gln Ala Ser Phe Arg Gly His Pro Phe Arg
1               5                   10
```

```
<210> SEQ ID NO 39
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 39

Ile Lys Arg Phe Gly Ser Lys Ala His Leu Pro Phe Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 40

Ser Pro Gln Pro Glu Tyr Val Asn Gln Pro Pro Phe Arg
1               5                   10

<210> SEQ ID NO 41
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 41

Asn Leu Leu Pro Leu Ser Pro Glu Glu Phe Pro Phe Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 42

Leu Pro Val Pro Glu Tyr Ile Asn Gln Ser Pro Phe Arg
1               5                   10

<210> SEQ ID NO 43
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 43

Val Lys Ser Arg Trp Ser Gly Ser Gln Gln Pro Phe Arg
1               5                   10

<210> SEQ ID NO 44
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 44

Phe Lys Asn Ile Val Thr Pro Arg Thr Pro Pro Phe Arg
1               5                   10
```

```
<210> SEQ ID NO 45
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 45

Arg Glu Val Gly Asp Tyr Gly Gln Leu His Pro Phe Arg
1               5                   10

<210> SEQ ID NO 46
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 46

Arg Pro Gln Arg Ala Thr Ser Asn Val Phe Pro Phe Arg
1               5                   10

<210> SEQ ID NO 47
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 47

Glu Pro Glu Gly Asp Tyr Glu Glu Val Leu Pro Phe Arg
1               5                   10

<210> SEQ ID NO 48
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 48

Phe Asp Asp Pro Ser Tyr Val Asn Val Gln Pro Phe Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 49

Lys Arg Lys Gln Ile Ser Val Arg Gly Leu Pro Phe Arg
1               5                   10

<210> SEQ ID NO 50
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 50

Leu Leu Arg Gly Pro Ser Trp Asp Pro Phe Pro Phe Arg
1               5                   10
```

```
<210> SEQ ID NO 51
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 51

Leu Lys Arg Ser Leu Ser Glu Leu Glu Ile Pro Phe Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 52

Pro Gln Glu Gly Leu Tyr Asn Glu Leu Gln Pro Phe Arg
1               5                   10

<210> SEQ ID NO 53
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 53

Leu Leu Arg Leu Phe Ser Phe Lys Ala Pro Pro Phe Arg
1               5                   10

<210> SEQ ID NO 54
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 54

Val Gln Asn Pro Val Tyr His Asn Gln Pro Pro Phe Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 55

Glu Lys Arg Lys Asn Ser Ile Leu Asn Pro Pro Phe Arg
1               5                   10

<210> SEQ ID NO 56
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 56

Ala Lys Lys Arg Leu Ser Val Glu Arg Ile Pro Phe Arg
1               5                   10

<210> SEQ ID NO 57
```

```
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 57

Arg Lys Arg Leu Ile Ser Ser Val Glu Asp Pro Phe Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 58

Leu Phe Pro Arg Asn Tyr Val Thr Pro Val Pro Phe Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 59

Val Arg Arg Phe Asn Thr Ala Asn Asp Asp Pro Phe Arg
1               5                   10

<210> SEQ ID NO 60
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 60

Lys Lys Gly Gln Glu Ser Phe Lys Lys Gln Pro Phe Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 61

Phe Leu Gln Arg Tyr Ser Ser Asp Pro Thr Pro Phe Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 62

Arg Lys Leu Lys Asp Thr Asp Ser Glu Glu Pro Phe Arg
1               5                   10

<210> SEQ ID NO 63
<211> LENGTH: 14
```

```
<212> TYPE: PRT
<213> ORGANISM: Artificial Sequence
<220> FEATURE:
<223> OTHER INFORMATION: The sequence was designed and synthesized

<400> SEQUENCE: 63

Arg Thr Tyr Ser Leu Gly Ser Ala Leu Arg Pro Pro Phe Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 64

Arg Ile Arg Thr Gln Ser Phe Ser Leu Gln Pro Phe Arg
1               5                   10

<210> SEQ ID NO 65
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 65

Glu Pro Glu Asn Asp Tyr Glu Asp Val Glu Pro Phe Arg
1               5                   10

<210> SEQ ID NO 66
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 66

Lys Pro Lys Asp Ala Ser Gln Arg Arg Arg Pro Phe Arg
1               5                   10

<210> SEQ ID NO 67
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 67

Leu Leu Ser Glu Leu Ser Arg Arg Arg Ile Pro Phe Arg
1               5                   10

<210> SEQ ID NO 68
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 68

Lys Leu Arg Lys Val Ser Lys Gln Glu Glu Pro Phe Arg
1               5                   10

<210> SEQ ID NO 69
<211> LENGTH: 13
<212> TYPE: PRT
```

```
<213> ORGANISM: Artificial Sequence
<220> FEATURE:
<223> OTHER INFORMATION: The sequence was designed and synthesized

<400> SEQUENCE: 69

Arg Lys Gly His Glu Tyr Thr Asn Ile Lys Pro Phe Arg
1               5                   10

<210> SEQ ID NO 70
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 70

Val Lys Arg Arg Asp Tyr Leu Asp Leu Ala Pro Phe Arg
1               5                   10

<210> SEQ ID NO 71
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 71

Val Leu Leu Arg Pro Ser Arg Arg Val Arg Pro Phe Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 72

Glu Leu Gln Asp Asp Tyr Glu Asp Leu Leu Pro Phe Arg
1               5                   10

<210> SEQ ID NO 73
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 73

Leu Asp Asn Pro Asp Tyr Gln Gln Asp Phe Pro Phe Arg
1               5                   10

<210> SEQ ID NO 74
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 74

Thr Asp Lys Glu Tyr Tyr Thr Val Lys Asp Pro Phe Arg
1               5                   10

<210> SEQ ID NO 75
<211> LENGTH: 13
<212> TYPE: PRT
<213> ORGANISM: Artificial Sequence
```

<220> FEATURE:
<223> OTHER INFORMATION: The sequence was designed and synthesized

<400> SEQUENCE: 75

Ser Lys Arg Arg Asn Ser Glu Phe Glu Ile Pro Phe Arg
1               5                   10

<210> SEQ ID NO 76
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 76

Lys Lys Lys Lys Phe Ser Phe Lys Lys Pro Pro Phe Arg
1               5                   10

<210> SEQ ID NO 77
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 77

Arg Lys Arg Arg Ser Ser Ser Tyr His Val Pro Phe Arg
1               5                   10

<210> SEQ ID NO 78
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 78

Phe Lys Arg Arg Arg Ser Ser Lys Asp Thr Pro Phe Arg
1               5                   10

<210> SEQ ID NO 79
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 79

Phe Lys Asn Asp Lys Ser Lys Thr Trp Gln Pro Phe Arg
1               5                   10

<210> SEQ ID NO 80
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 80

Lys Lys Lys Arg Phe Ser Phe Lys Lys Ser Pro Phe Arg
1               5                   10

<210> SEQ ID NO 81
<211> LENGTH: 13
<212> TYPE: PRT
<213> ORGANISM: Artificial Sequence
<220> FEATURE:

<223> OTHER INFORMATION: The sequence was designed and synthesized

<400> SEQUENCE: 81

Lys Lys Arg Lys Arg Ser Arg Lys Glu Ser Pro Phe Arg
1               5                   10

<210> SEQ ID NO 82
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 82

Ile Lys Lys Ser Trp Ser Arg Trp Thr Leu Pro Phe Arg
1               5                   10

<210> SEQ ID NO 83
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 83

His His Ile Asp Tyr Tyr Lys Lys Thr Thr Pro Phe Arg
1               5                   10

<210> SEQ ID NO 84
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 84

Trp Pro Trp Gln Val Ser Leu Arg Thr Arg Pro Phe Arg
1               5                   10

<210> SEQ ID NO 85
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 85

His Leu Glu Lys Lys Tyr Val Arg Arg Asp Pro Phe Arg
1               5                   10

<210> SEQ ID NO 86
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 86

Arg Leu Arg Arg Leu Ser Thr Lys Tyr Arg Pro Phe Arg
1               5                   10

<210> SEQ ID NO 87
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 87

Glu Tyr Asp Arg Leu Tyr Glu Glu Tyr Thr Pro Phe Arg
1               5                   10

<210> SEQ ID NO 88
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 88

His Thr Gly Phe Leu Thr Glu Tyr Val Ala Thr Arg Arg
1               5                   10

<210> SEQ ID NO 89
<211> LENGTH: 14
<212> TYPE: PRT
<213> ORGANISM: Artificial Sequence
<220> FEATURE:
<223> OTHER INFORMATION: The sequence was designed and synthesized

<400> SEQUENCE: 89

Thr Ser Phe Leu Leu Thr Pro Tyr Val Val Thr Arg Pro Arg
1               5                   10

<210> SEQ ID NO 90
<211> LENGTH: 13
<212> TYPE: PRT
<213> ORGANISM: Artificial Sequence
<220> FEATURE:
<223> OTHER INFORMATION: The sequence was designed and synthesized

<400> SEQUENCE: 90

Ile Tyr Lys Asn Asp Tyr Tyr Arg Lys Arg Pro Phe Arg
1               5                   10

<210> SEQ ID NO 91
<211> LENGTH: 21
<212> TYPE: DNA
<213> ORGANISM: Artificial Sequence
<220> FEATURE:
<223> OTHER INFORMATION: The sequence was designed and synthesized

<400> SEQUENCE: 91
cccaacatca tcactctgaa a                                             21

<210> SEQ ID NO 92
<211> LENGTH: 21
<212> TYPE: DNA
<213> ORGANISM: Artificial Sequence
<220> FEATURE:
<223> OTHER INFORMATION: The sequence was designed and synthesized

<400> SEQUENCE: 92
agcgctgaga atggacagca a                                             21

<210> SEQ ID NO 93
<211> LENGTH: 15
<212> TYPE: PRT
<213> ORGANISM: Artificial Sequence
<220> FEATURE:
<223> OTHER INFORMATION: The sequence was designed and synthesized

<400> SEQUENCE: 93

```
Ser Lys Glu Tyr Asp Arg Leu Tyr Glu Glu Tyr Thr Arg Thr Ser
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: The sequence was designed and synthesized

<400> SEQUENCE: 94

Ser Arg Glu Tyr Asp Arg Leu Tyr Glu Glu Tyr Thr Arg Thr Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: The sequence was designed and synthesized

<400> SEQUENCE: 95

Asn Gln Glu Tyr Asp Arg Leu Tyr Glu Asp Tyr Thr Arg Thr Ser
1               5                   10                  15

<210> SEQ ID NO 96
<211> LENGTH: 11
<212> TYPE: PRT
<213> ORGANISM: Artificial Sequence
<220> FEATURE:
<223> OTHER INFORMATION: The sequence was designed and synthesized

<400> SEQUENCE: 96

Pro Glu Arg Arg Tyr Ala Asn Asn Pro Phe Arg
1               5                   10
```